United States Patent
Huizinga et al.

(12) 
(10) Patent No.: US 12,158,468 B2
(45) Date of Patent: Dec. 3, 2024

(54) FAB-LINKED GLYCANS AS BIOMARKER FOR THE TRANSITION FROM A PRE-DISEASE "AT-RISK-PHASE" TO RHEUMATOID ARTHRITIS; AAV OR SJÖGREN SYNDROME

(71) Applicant: Academisch Ziekenhuis Leiden h.o.d.n. LUMC, Leiden (NL)

(72) Inventors: Thomas Willem Johannes Huizinga, Leiden (NL); Reinaldus Everardus Maria Toes, Leiden (NL); Leendert Adrianus Trouw, Sassenheim (NL); Hans Ulrich Scherer, Leiden (NL)

(73) Assignee: Academisch Ziekenhuis Leiden h.o.d.n. LUMC, Leiden (NL)

( * ) Notice: Subject to any disclaimer, the term of this patent is extended or adjusted under 35 U.S.C. 154(b) by 203 days.

(21) Appl. No.: 16/464,651

(22) PCT Filed: Nov. 24, 2017

(86) PCT No.: PCT/NL2017/050773
§ 371 (c)(1),
(2) Date: May 28, 2019

(87) PCT Pub. No.: WO2018/097724
PCT Pub. Date: May 31, 2018

(65) Prior Publication Data
US 2019/0317092 A1    Oct. 17, 2019

(30) Foreign Application Priority Data
Nov. 25, 2016    (EP) .................................... 16200775

(51) Int. Cl.
*G01N 33/564* (2006.01)
*G01N 33/68* (2006.01)

(52) U.S. Cl.
CPC ....... *G01N 33/564* (2013.01); *G01N 33/6893* (2013.01); *G01N 2800/102* (2013.01); *G01N 2800/328* (2013.01)

(58) Field of Classification Search
None
See application file for complete search history.

(56) References Cited

FOREIGN PATENT DOCUMENTS

| EP | 3159694 A1 | 4/2017 |
| WO | 2012/105838 A1 | 8/2012 |
| WO | 2015/194350 A1 | 12/2015 |

OTHER PUBLICATIONS

Kassermann, F., et al. Plos One, 2012:7(6): 1-11.*
Shi et al., "Autoantibodies Recognizing Carbamylated Proteins are Present in Sera of Patients With Rheumatoid Arthritis and Predict Joint Damage," Proceedings of the National Academy of Sciences, vol. 108, (Oct. 18, 2011), pp. 17372-17377.
Scherer et al., "[OP0177] A High Frequency of N-Glycans in the Acpa-Igg Variable Domain Modulates Reactivity to Citrullinated Antigens," Annals of the Rheumatic Diseases, vol. 73, (Suppl 2), 1 page.
Rombouts et al., "Extensive Glycosylation of ACPA-IgG Variable Domains Modulates Binding to Citrullinated Antigens in Rheumatoid Arthritis," Annals of the Rheumatic Diseases, vol. 75, (Jan. 27, 2017), pp. 578-585, 2015.
Kroese et al., "Autoimmunity: Break-Through in the Diagnosis and Treatment of Immune-Mediated Inflammatory Diseases," Immunology Letters, vol. 162, (2014), pp. 150-162.
Holland et al., "Differential Glycosylation of Polyclonal IgG, IgG-Fc and IgG-Fab isolated from the Sera of Patients With ANCA-associated Systemic Vasculitis," Biochimica et Biophysica Acta, vol. 1760, (2006), pp. 669-677.
Hafkenscheid et al., "Structural Analysis of Variable Domain Glycosylation of Anti-Citrullinated Protein Antibodies in Rheumatoid Arthritis Reveals the Presence of Highly Sialylated Glycans," Molecular Cellular Proteomics, vol. 16, (2017), pp. 278-287.
Goulabschand et al., "Impact of Autoantibody Glycosylation in Autoimmune Diseases," Autoimmunity Reviews, vol. 13, (2014), pp. 742-750.
Dekkers et al., "The Role of Anticitrullinated Protein Antibodies in The Early Stages of Rheumatoid Arthritis," Current Opinion in Rheumatology, (Jan. 26, 2017), 7 pages.
Wu et al. "Analysis of Glycan Variation on Glycoproteins from Serum by the Reverse Lectin-Based ELISA Assay" J. Proteome Res., (Feb. 2014), vol. 13, pp. 2197-2204.
Japanese Notice of Reasons for Refusal for Japanese Application No. 2019-528084, dated Apr. 25, 2022, 11 pages with English translation.

* cited by examiner

*Primary Examiner* — Daniel E Kolker
*Assistant Examiner* — Maureen Varina Driscoll
(74) *Attorney, Agent, or Firm* — TraskBritt

(57) ABSTRACT

Means and methods for determining whether an individual that does not have rheumatoid arthritis, AAV or Sjögren syndrome at the moment of sampling is at risk of developing the disease, the method comprising determining whether an antibody-containing sample of the individual comprises an autoantibody associated with the disease that comprises an N-linked glycosylation at one or more positions in a Fab-portion of the antibody, the method further comprising determining the risk of the individual for developing the disease. The disease is preferably rheumatoid arthritis.

9 Claims, 39 Drawing Sheets
Specification includes a Sequence Listing.

| Name | Name in Figures of patent | Structure | UHPLC GP number |
|---|---|---|---|
| H5N2 | | 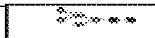 | GPS |
| H3N3F1 | | 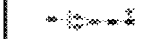 | GP1 |
| H3N4 | | 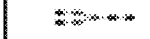 | GP2 |
| H6N2 | | 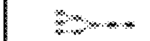 | |
| H3N4F1 | G0F | 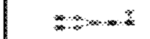 | GP4 |
| H4N4 | G1 | 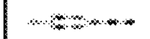 | GP7 |
| H7N2 | | 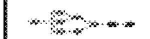 | |
| H3N5 | G0B | 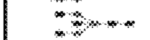 | GP3 |
| H4N3S1 | | 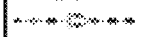 | GP16 |
| HRN4F1 | G1F | 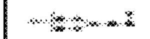 | GP8/9 |
| H5N4 | G2 | 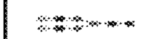 | GP12 |
| H3N5F1 | G0FB | 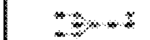 | GP6 |
| H4N5 | G1B | 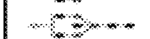 | |
| H4N3F1S1[a] | | 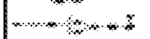 | |
| H8N2 | | 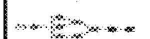 | |
| H4N4S1[a] | | 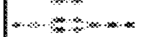 | |
| H5N4F1 | G2F | 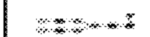 | GP14 |
| H4N5F1 | G1FB | 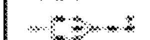 | GP10/11 |
| H5N5 | G2B | 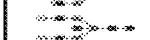 | GP13 |
| H9N2 | | 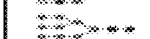 | |
| H4N4F1S1[a] | G1FS1 | 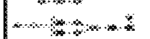 | GP16 |
| H5N4S1[a] | G2S1 | 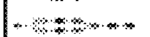 | GP17 |
| H4N5S1[a] | G1S1B | 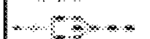 | |
| H5N5F1 | G2FB | 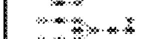 | GP15 |
| H5N4F1S1[a] | G2FS1 | 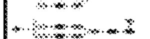 | GP18 |
| H4N5F1S1[a] | G2FS1B | 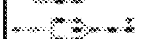 | |
| H5N5S1[a] | G2S1B | 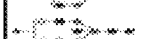 | |
| H5N4S2[a] | G2S2 | 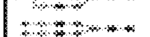 | GP21 |
| H5N5F1S1[a] | G2FS1B | 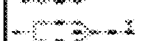 | GP19 |
| H5N4F1S2[a] | G2FS2 | 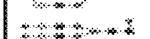 | GP23 |
| H5N5S2[a] | G2S2B | 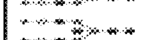 | GP22 |
| H5N5F1S2[a] | G2FS2B | 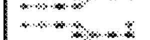 | GP24 |
| H5N4F1E1L1[a,b] | | | |
| H5N5F1E1L1[a,b] | | | |
| H6N5F1S2[a] | | | GPx | a: α2,6 sialic acid, confirmed by EE-glycans in MALDI-TOF-MS
b: α2,3 sialic acid, confirmed by EE-glycans in MALDI-TOF-MS
H: Hexoses
N: N-acetylhexosamine
F: Fucose
B: Bisecting N-acetylglucosamine
S: Sialic acid
E: ethyl esterified α2,6-linked N-acetylneuraminic acid (sialic acid)
L: lactonized α2,3-linked N-acetylneuraminic acid

FIG. 1A

ACPA purification
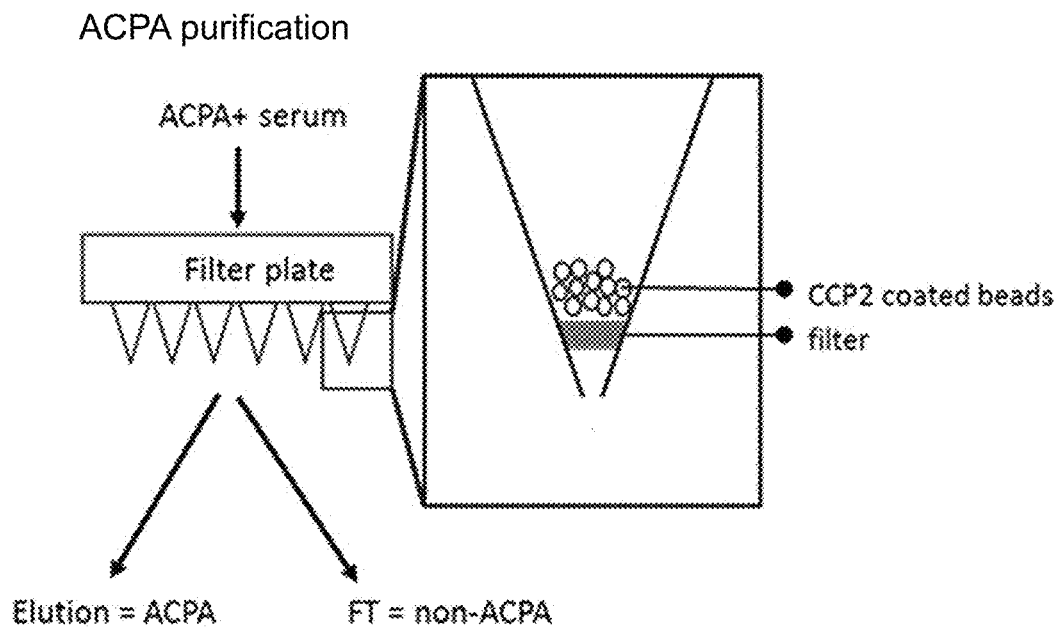
SNA ELISA
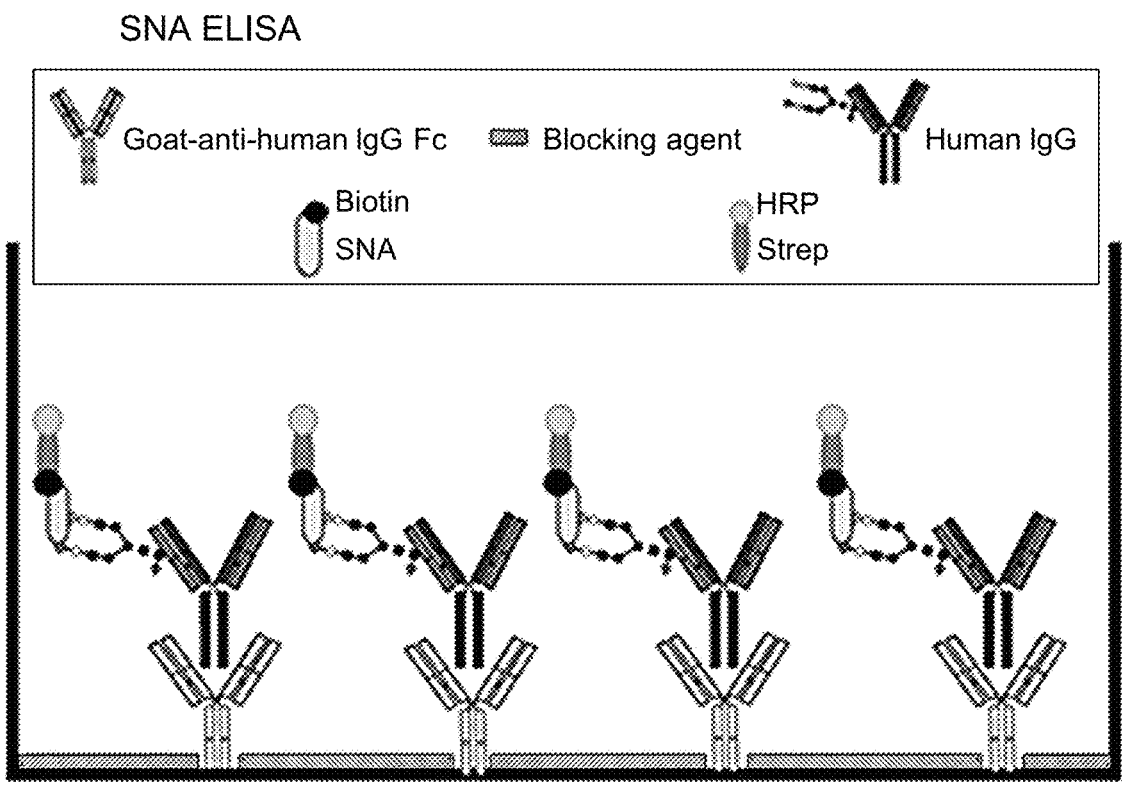
FIG. 3A

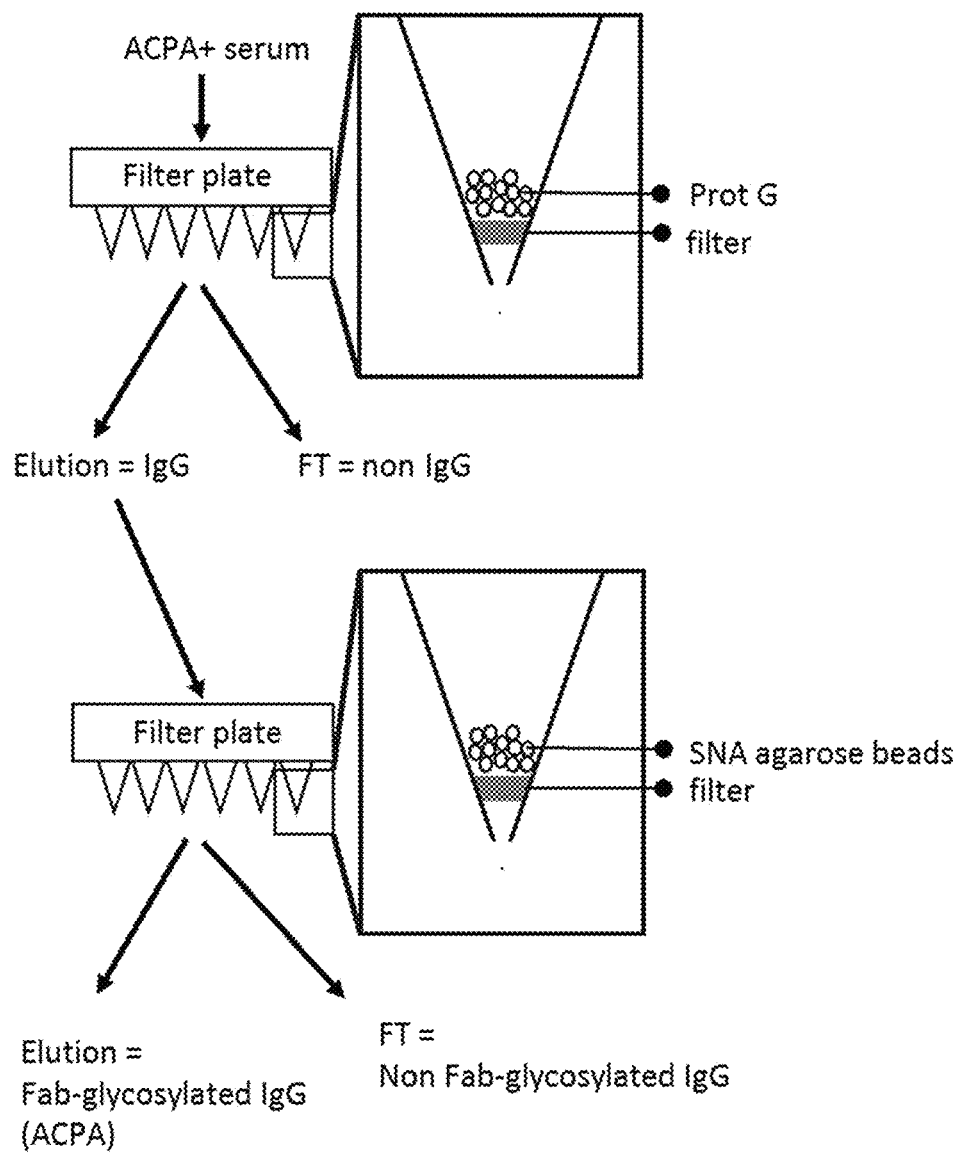
FIG. 4A.1

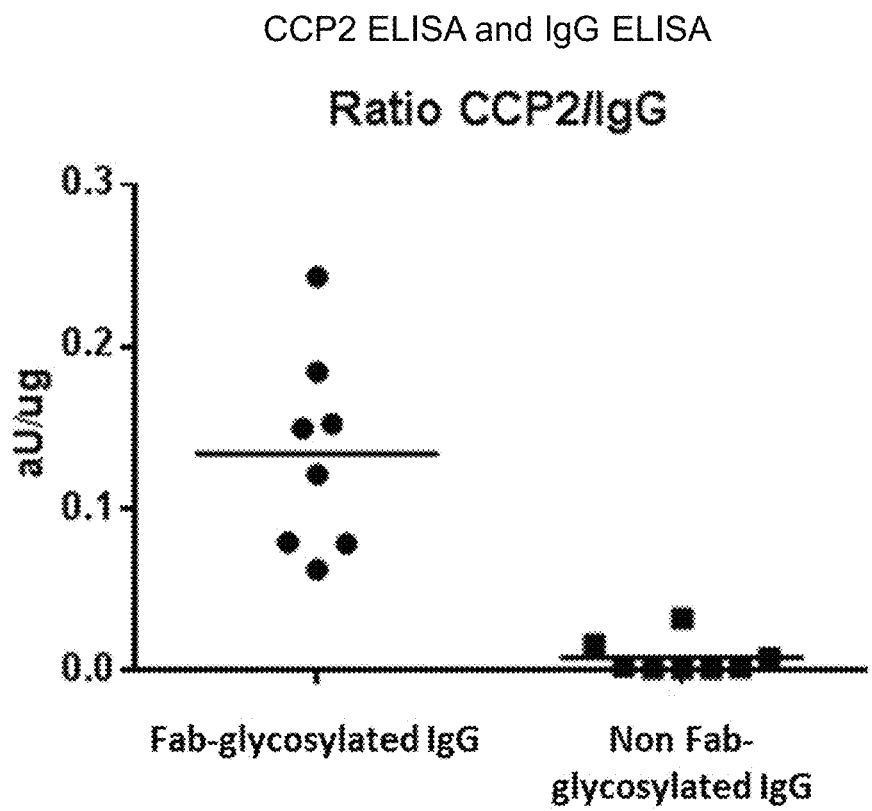
FIG. 4A.2
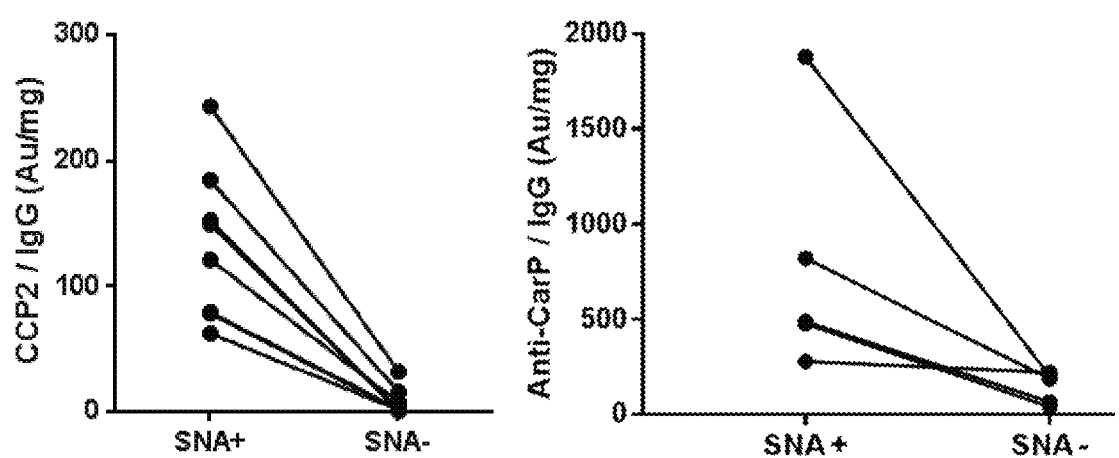
FIG. 4B

FIG. 6
Amino acid sequence of Fibrinogen alpha

```
          10         20         30         40         50         60         70
    MFSMRIVCLV LSVVGTAWTA DSGEGDFLAE GGGVRGPRVV ERHQSACKDS DWPFCSDEDW NYKCPSGCRM
          80         90        100        110        120        130        140
    KGLIDEVNQD FTNRINKLKN SLFEYQKNNK DSHSLTTNIM EILRGDFSSA NNRDNTYNRV SEDLRSRIEV
         150        160        170        180        190        200        210
    LKRKVIEKVQ HIQLLQKNVR AQLVDMKRLE VDIDIKIRSC RGSCSRALAR EVDLKDYEDQ QKQLEQVIAK
         220        230        240        250        260        270        280
    DLLPSRDRQH LPLIKMKPVP DLVPGNFKSQ LQKVPPEWKA LTDMPQMRME LERPGGNEIT RGGSTSYGTG
         290        300        310        320        330        340        350
    SETESPRNPS SAGSWNSGSS GPGSTGNRNP GSSGTGGTAT WKPGSSGPGS TGSWNSGSSG TGSTGNQNPG
         360        370        380        390        400        410        420
    SPRPGSTGTW NPGSSERGSA GHWTSESSVS GSTGQWHSES GSFRPDSPGS GNARPNNPDW GTFEEVSGNV
         430        440        450        460        470        480        490
    SPGTRREYHT EKLVTSKGDK ELRTGKEKVT SGSTTTTRRS CSKTVTKTVI GPDGHKEVTK EVVTSEDGSD
         500        510        520        530        540        550        560
    CPEAMDLGTL SGIGTLDGFR HRHPDEAAFF DTASTGKTFP GFFSPMLGEF VSETESRGSE SGIFTNTKES
         570        580        590        600        610        620        630
    SSHHPGIAEF PSRGKSSSYS KQFTSSTSYN RGDSTFESKS YKMADEAGSE ADHEGTHSTK RGHAKSRPVR
         640        650        660        670        680        690        700
    DCDDVLQTHP SGTQSGIFNI KLPGSSKIFS VYCDQETSLG GWLLIQQRMD GSLNFNRTWQ DYKRGFGSLN
         710        720        730        740        750        760        770
    DEGEGEFWLG NDYLHLLTQR GSVLRVELED WAGNEAYAEY HFRVGSEAEG YALQVSSYEG TAGDALIEGS
         780        790        800        810        820        830        840
    VEEGAEYTSH NNMQFSTFDR DADQWEENCA EVYGGGWWYN NCQAANLNGI YYPGGSYDPR NNSPYEIENG
         850        860
    VVWVSFRGAD YSLRAVRMKI RPLVTQ
```

FIG. 7

Amino acid sequence of Fibrinogen beta

```
         10         20         30         40         50         60
MKRMVSWSFH KLKTMKHLLL LLLCVFLVKS QGVNDNEEGF FSARGHRPLD KKREEAPSLR
         70         80         90        100        110        120
PAPPPISGGG YRARPAKAAA TQKKVERKAP DAGGCLHADP DLGVLCPTGC QLQEALLQQE
        130        140        150        160        170        180
RPIRNSVDEL NNNVEAVSQT SSSSFQYMYL LKDLWQKRQK QVKDNENVVN EYSSELEKHQ
        190        200        210        220        230        240
LYIDETVNSN IPTNLRVLRS ILENLRSKIQ KLESDVSAQM EYCRTPCTVS CNIPVVS
        250        260        270        280        290        300
CEEIIRKGGE TSEMYLIQPD SSVKPYRVYC DMNTENGGWT VIQNRQDGSV DFGRKWDPYK
        310        320        330        340        350        360
QGFGNVATNT DGKNYCGLPG EYWLGNDKIS QLTRMGPTEL LIEMEDWKGD KVKAHYGGFT
        370        380        390        400        410        420
VQNEANKYQI SVNKYRGTAG NALMDGASQL MGENRTMTIH NGMFFSTYDR DNDGWLTSDP
        430        440        450        460        470        480
RKQCSKEDGG GWWYNRCHAA NPNGRYYWGG QYTWDMAKHG TDDGVVWMNW KGSWYSMRKM
        490
SMKIRPFFPQ Q
```

FIG. 8

```
           10          20          30          40          50          60
MSWSLHPRNL ILYFYALLFL SSTCVAYVAT RDNCCILDER FGSYCPTTCG IADFLSTYQT
           70          80          90         100         110         120
KVDKDLQSLE DILHQVENKT SEVKQLIKAI QLTYNPDESS KPNMIDAATL KSRKMLEEIM
          130         140         150         160         170         180
KYEASILTHD SSIRYLQEIY NSNNQKIVNL KEKVAQLEAQ CQEPCKDTVQ IHDITGKDCQ
          190         200         210         220         230         240
DIANKGAKQS GLYFIKPLKA NQQFLVYCEI DGSGNGWTVF QKRLDGSVDF KKNWIQYKEG
          250         260         270         280         290         300
FGHLSPTGTT EFWLGNEKIH LISTQSAIPY ALRVELEDWN GRTSTADYAM FKVGPEADKY
          310         320         330         340         350         360
RLTYAYFAGG DAGDAFDGFD FGDDPSDKFF TSHNGMQFST WDNDNDKFEG NCAEQDGSGW
          370         380         390         400         410         420
WMNKCHAGHL NGVYYQGGTY SKASTPNGYD NGIIWATWKT RWYSMKKTTM KIIPFNRLTI
          430         440         450
GEGQQHHLGG AKQVRPEHPA ETEYDSLYPE DDL
```

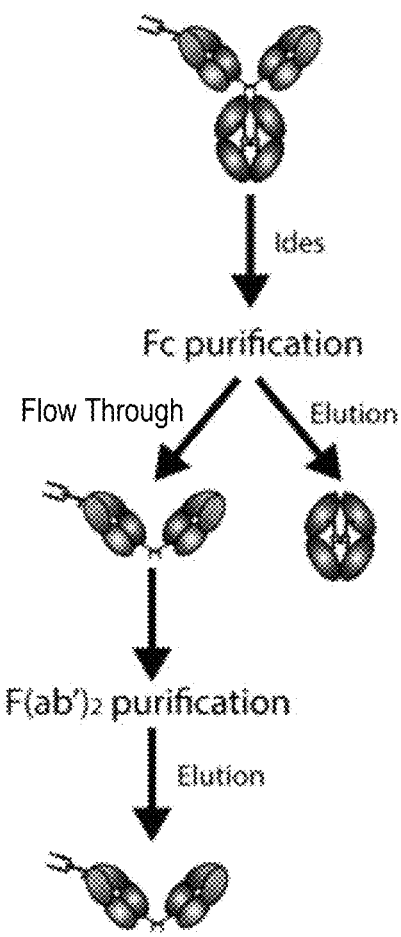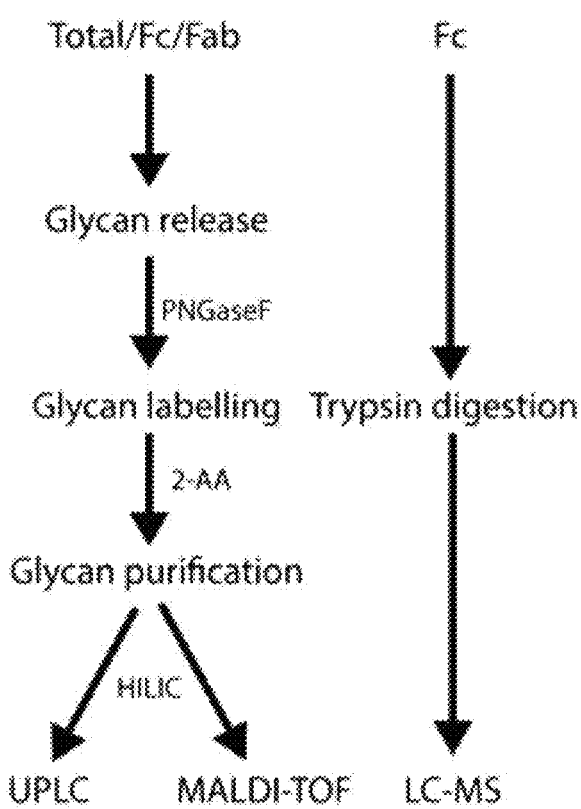
FIG. 9B
FIG. 9C

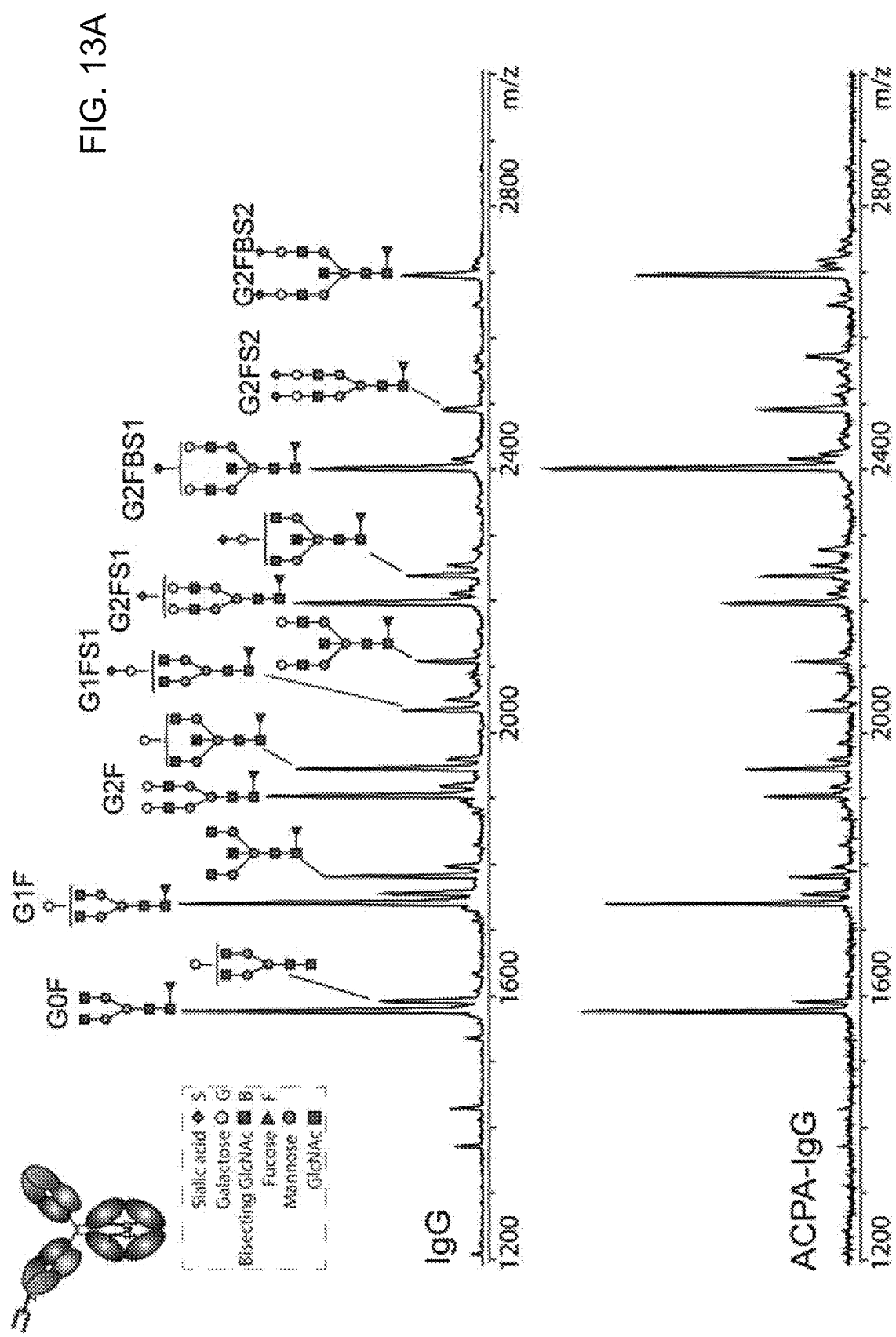

FIG. 14

RL0633-H
*IGHV*
QVQLEESGPGLVRPSETLSLTCSVSGVSLSEISYFWGWVRQPPGKGLEWIGTIHYSARIYY
TPSLQSRVSMSVDTSKNQFSLNVTSVTAADTAVYYCAISYDYGDFFDYWGQGILVTVSS
*IGLV*
IFILAQPHSVSESAGKTVTISCTRSSGSIASTYVQWYQQRPGSSPSTVVFQNDQRPSGVPD
RFSGSIDSSSNSASLTISGLKTEDEADYYCQSYDTANHVLFGGGTKLTVL

RL0676-B
*IGHV*
QVQLQESGPGLVKPSETLSLTCNVSGGSLKSDNFYWSWIRQRPGQGLEFIGYYVYSDITY
FNPSLKSRVNISLDTSKRQLSLQVRSVTAADTGIYYCARGIGLGDVIICEGFDVWGRGTTV
TVSS
*IGLV*
NFLLAQPHSVSESPGKTITLSCTRSSGNVASESVQWYQQRPGSSPTTVILQNNRRPSGVP
DRFSGSIDTSSNSASLTISGLRPEDEADYFCQSFDSSGLIFGGGTKLTVL

RL0758-E
*IGHV*
QVQLVESGGGVVQPGKSLRLSCVASGFTFKNFALHWVRQAPGRGLEWLAVISDDGSESH
YADSVQGRFLISRDNSTNTLVLQMNHLRSDDTAHYYCARDLSKIFPLYYGMDVWGQGTT
VIVSA
*IGLV*
EVVLTQSPGTLSLSPGERATLSCRASRHVSSTYLVWYQHKPGQPPRLLISGASRRATGIPD
RFNGSGSGTDFTLTIASLEPEDFAVYYCHHYGFSPCSFGQGTKLEIK

FIG. 16

MKWVTFISLLFLFSSAYSRGVFRRDAHKSEVAHRFKDLGEENFKALVLIAFAQYLQQCPFEDHVKLVNEVT
EFAKTCVADESAENCDKSLHTLFGDKLCTVATLRETYGEMADCCAKQEPERNECFLQHKDDNPNLPRLVRP
EVDVMCTAFHDNEETFLKKYLYEIARRHPYFYAPELLFFAKRYKAAFTECCQAADKAACLLPKLDELRDEG
KASSAKQGLKCASLQKFGERAFKAWAVARLSQRFPKAEFAEVSKLVTDLTKVHTECCHGDLLECADDRADL
AKYICENQDSISSKLKECCEKPLLEKSHCIAEVENDEMPADLPSLAADFVGSKDVCKNYAEAKDVFLGMFL
YEYARRHPDYSVVLLLRLAKTYETTLEKCCAAADPHECYAKVFDEFKPLVEEPQNLIKQNCELFEQLGEYK
FQNALLVRYTKKVPQVSTPTLVEVSRNLGKVGSKCCKHPEAKRMPCAEDCLSVFLNQLCVLHEKTPVSDRV
TKCCTESLVNGRPCFSALEVDETYVPKEFNAETFTFHADICTLSEKERQIKKQTALVELVKHKPKATKEQL
KAVMDDFAAFVEKCCKADDKETCFAEEGKKLVAASQAALGL

FIG. 17

1 MPSSVSWGIL LLAGLCCLVP VSLAEDPQGD AAQKTDTSHH DQDHPTFNKI TPNLAEFAFS
 61 LYRQLAHQSN STNIFFSPVS IATAFAMLSL GTKADTHDEI LEGLNFNLTE IPEAQIHEGF
121 QELLRTLNQP DSQLQLTTGN GLFLSEGLKL VDKFLEDVKK LYHSEAFTVN FGDTEEAKKQ
181 INDYVEKGTQ GKIVDLVKEL DRDTVFALVN YIFFKGKWER PFEVKDTEEE DFHVDQVTTV
241 KVPMMKRLGM FNIQHCKKLS SWVLLMKYLG NATAIFFLPD EGKLQHLENE LTHDIITKFL
301 ENEDRRSASL HLPKLSITGT YDLKSVLGQL GITKVFSNGA DLSGVTEEAP LKLSKAVHKA
361 VLTIDEKGTE AAGAMFLEAI PMSIPPEVKF NKPFVFLMIE QNTKSPLFMG KVVNPTQK

FAB-LINKED GLYCANS AS BIOMARKER FOR THE TRANSITION FROM A PRE-DISEASE "AT-RISK-PHASE" TO RHEUMATOID ARTHRITIS; AAV OR SJÖGREN SYNDROME

CROSS-REFERENCE TO RELATED APPLICATIONS

This application is a national phase entry under 35 U.S.C. § 371 of International Patent Application PCT/NL2017/050773, filed Nov. 24, 2017, designating the United States of America and published in English as International Patent Publication WO 2018/097724 A1 on May 31, 2018, which claims the benefit under Article 8 of the Patent Cooperation Treaty to European Patent Application Serial No. 16200775.1, filed Nov. 25, 2016.

TECHNICAL FIELD

The disclosure is related to the field of autoimmune disease, in particular, anti-neutrophil cytoplasmic antibody (ANCA)-associated vasculitis (AAV); Sjögren syndrome and arthritis, in particular, to the field of rheumatoid arthritis. It also relates to methods for monitoring individuals for the development of the autoimmune disease or the treatment of autoimmune disease, preferably (rheumatoid) arthritis.

STATEMENT ACCORDING TO 37 C.F.R. § 1.821(c) or (e)—SEQUENCE LISTING SUBMITTED AS A TXT AND PDF FILES

Pursuant to 37 C.F.R. § 1.821 (c) or (e), a Sequence Listing ASCII text file entitled 2183-P14958US_ST25.txt, 31,667 bytes in size, generated Nov. 1, 2022, has been submitted, the contents of which are hereby incorporated by reference.

BACKGROUND

IgGs are glycoproteins that contain a conserved glycosylation site located at Asn297 present in the Fc-portion. From a structural point of view, these Fc-glycans serve as an internal scaffold and are crucial for maintaining the conformation of the Fc tail of the IgG molecule. Fc-glycosylation can modulate the interaction with Fcγ-receptors (FcγR) and can be involved in other effector functions, since specific glycoforms can activate complement pathways (C1q- and MBL-mediated) and/or modulate FcγR-binding. For instance, core-fucose residues can influence IgG binding to FcγRIIIa and lack of core-fucose is responsible for enhanced antibody-dependent cellular cytotoxicity. Likewise, low content of sialic acid and galactose residues in Fc-glycans confers important pro-inflammatory properties to IgG, as it favors the binding of IgG to activating FcγRs.

In addition to Fc-linked N-glycans, ~15-25% of IgG molecules in human serum contain N-linked glycans present in the Fab-region. Fab-glycans can also modulate cellular function and have been implicated in the emergence of lymphomas such as follicular lymphoma, diffuse large B-cell lymphoma and Burkitt's lymphoma B-cells, presumably through the provision of aberrant Fab-glycosylated B-cell receptor cross-linking via the glycan to lectins.

Antibodies that can bind post-translational modifications (AMPA) such as citrullinated protein antigens (ACPA), homo-citrullinated protein antigens (anti-CarP) and acetylated lysine protein antigens (AAPA) have recently been found in patients with rheumatoid arthritis (RA). Such antibodies have been implicated in disease pathogenesis. Malondialdehyde-acetaldehyde adduct (MAA-adduct) formation is another post-translational modification that is increased in RA. The modification results in antibody responses that are associated with ACPAs (Thiele et al. 2015: Arthritis Rheumatol. Vol. 67 (3): 645-655: doi 10.1002/art.38969). Various post-translational modifications that are implicated in the development of autoimmune diseases such as RA (reviewed in Trouw et al. (2017; Nature reviews Rheumatology doi: 10.1058/nrrheum.2017.15). Recently, the intriguing observation was made that ACPA isolated from RA patients are extensively Fab-glycosylated. ACPA are highly specific for RA and their presence associates with disease severity and predicts the development of RA in subjects at risk (Scott 2010; Willemze, A., et al., "New biomarkers in rheumatoid arthritis." Neth. J. Med. 70.9 (2012): 392-9). Although it is unknown whether the Fab-glycans on IgG molecules can mediate specific functions in normal immune responses, evidence has been obtained supporting the notion that their presence can influence epitope recognition as well as half-life of antibodies in vivo (Goletz 2012; Co 1993; Leibiger 1999).

To undergo N-linked glycosylation, proteins need to have an N-linked glycosylation consensus sequence (typically N-X-S/T, where X≠P; herein N=Asparagine; S=Serine; T=Threonine; P=Proline and X is any amino acid but not Proline. S/T in the formula means an S or a T at that position; sometimes there is a C (cysteine) at the position of S/T). Importantly, it was previously shown that N-linked glycosylation consensus sites in ACPA-IgG were not germline-encoded but introduced during somatic hypermutation (Rombouts 2015).

BRIEF SUMMARY

In the present disclosure, it was identified that the structure of N-linked glycans in the Fab-domain of autoantibodies associated with rheumatoid arthritis, Sjögren syndrome and AAV such as AMPA antibodies such as ACPA, anti-CarP, anti-MAA-adduct antibodies and AAPA antibodies in rheumatoid arthritis. It was also observed that ACPA-IgG molecules of ACPA-positive individuals that have not yet shown clinical signs of arthritis, i.e., "individuals at-risk," exhibit a lower degree of Fab glycosylation as compared to ACPA-IgG in patients with established RA. Thus, the appearance of ACPA Fab glycans and/or the degree of ACPA Fab-glycosylation marks the transition from the pre-clinical phase to the onset of clinically overt arthritis. As such, the detection of ACPA Fab glycans by appropriate bioassays can be used to identify this transition and to guide treatment strategies for the prevention or delay of disease onset. The same is true for autoantibodies associated with Sjögren syndrome and AAV. Autoantibodies of autoantibody-positive individuals that have not yet shown clinical signs of Sjögren syndrome and/or AAV, i.e., "individuals at-risk" of developing the disease, exhibit a lower degree of Fab glycosylation as compared to autoantibodies in patients with established Sjögren syndrome and/or AAV.

In one embodiment, a method is provided of determining whether an individual that does not have rheumatoid arthritis, Sjögren syndrome or anti-neutrophil cytoplasmic antibody (ANCA)-associated vasculitis (AAV) at the moment of sampling is at risk of developing the disease, the method comprising determining whether an antibody-containing sample of the individual comprises an autoantibody associated with the disease and determining whether the antibody comprises an N-linked glycosylation at one or more positions in a Fab-portion of the antibody, the method further comprising determining the risk of the individual for developing the disease on the basis of the determinations.

Also provided is a method of analyzing an antibody-containing sample of an individual, the method comprising determining whether the sample comprises an autoantibody associated with rheumatoid arthritis, Sjögren syndrome or AAV that comprises an N-linked glycosylation at one or more positions in a Fab-portion of the antibody, the method characterized in that the sample is a sample of an individual that does not have rheumatoid arthritis symptoms, Sjögren syndrome symptoms or AAV symptoms at the moment of sampling.

Further provided is a method of preventing or delaying the development of a rheumatoid arthritis symptom, a Sjögren syndrome symptom or an AAV symptom in an individual, the method comprising:
  determining whether a sample of the individual contains an autoantibody associated with the disease;
  and determining whether the antibody has an N-linked glycosylated Fab-portion;
  wherein the sample is an antibody-containing sample of the individual and the individual did not have rheumatoid arthritis, Sjögren syndrome and AAV at the time of sampling; and
  treating the individual with a medicament for the disease prior to or at the onset of the individual presenting with the disease.

Also provided is a method of monitoring an individual at risk of developing rheumatoid arthritis, Sjögren syndrome or AAV, the method comprising monitoring the presence and/or the onset of an autoantibody associated with the disease in periodic antibody-containing samples of an individual, wherein the method further comprises determining whether a detected autoantibody associated with the disease comprises an N-linked glycan at one or more positions in a Fab-portion of the antibody.

Also provided is a rheumatoid arthritis, Sjögren syndrome or AAV medicament for use in a method of treatment of an individual at risk of developing one or more of the diseases wherein the individual is determined to be at risk by the detection of an autoantibody associated with the disease, which antibody comprises N-linked glycosylation at one or more positions in a Fab-portion of the antibody in an antibody-containing sample of the individual. In one embodiment, the individual does not have the disease at the moment of administering the medicament.

Also provided is a method of determining whether an antibody-containing sample comprises an anti-modified protein antibody (AMPA), preferably a citrulline, a homo-citrulline and/or an acetylated lysine binding AMPA, the method comprising:
  contacting antibodies of the sample with a peptide or protein that comprises a modified protein epitope, preferably comprising a citrulline, homo-citrulline, or acetylated lysine;
  contacting antibodies of the sample with a molecule that can bind an N-linked glycan on a Fab-portion of an antibody; and
  determining whether an antibody with an N-linked glycan on a Fab-portion of the antibody has bound to the modified protein epitope in the peptide or protein, wherein the modified protein epitope preferably comprises citrulline, a homo-citrulline or an acetylated lysine.

Further provided is a kit of parts useful in the detection of an AMPA, preferably an ACPA, an anti-CarP and/or an AAPA antibody in a sample, the kit comprising a peptide or protein that comprises a peptide or protein with a post-translationally modified epitope, preferably a citrullinated, a homo-citrullinated and/or an acetylated lysine epitope and a molecule that can bind an N-linked glycan on a Fab-portion of an antibody.

Further provided is a kit of parts useful in the detection of an autoantibody associated with rheumatoid arthritis, Sjögren syndrome or AAV such as an AMPA in a sample, the kit comprising a peptide or protein that can bind the autoantibody, such as a peptide or protein comprising a post-translational modification and a molecule that can bind an N-linked glycan on a Fab-portion of an antibody.

In one embodiment, a method of analyzing an antibody-containing sample of an individual is also provided, the method comprising determining whether the sample comprises an AMPA, preferably an ACPA antibody, an anti-CarP antibody and/or an AAPA antibody, which antibody comprises an N-linked glycan at one or more positions in a Fab-portion of the antibody, wherein the sample is a sample of an individual that does not have rheumatoid arthritis signs or symptoms at the moment of sampling.

Also provided is a method of determining whether an individual that does not have rheumatoid arthritis at the moment of sampling is at risk of developing rheumatoid arthritis, the method comprising determining whether an antibody-containing sample of the individual comprises an anti-modified protein antibody (AMPA), preferably an ACPA antibody, an or anti-CarP antibody and/or an AAPA antibody; and determining whether the antibody comprises an N-linked glycan at one or more positions in a Fab-portion of the antibody, the method further comprising determining the risk of the individual for developing the arthritis on the basis of the determinations.

The individual that does not have rheumatoid arthritis at the moment of sampling is preferably an AMPA, preferably an ACPA; an anti-CarP and/or an AAPA-positive individual, preferably with arthralgia (joint complaints/pain) without signs of clinically and/or radiographically detectable joint inflammation or arthritis or an individual that is asymptomatic and where ACPA, anti-CarP and/or AAPA serology is detected as an accidental finding or as part of a screening test. The individual preferably does not have chronic arthritis symptoms.

Further provided is a method of treating an individual for a rheumatoid arthritis symptom or the development thereof, the method comprising:
  determining whether a sample contains an AMPA, preferably an ACPA, an anti-CarP and/or an AAPA antibody that has an N-linked glycosylated Fab-portion;
  wherein the sample is an antibody-containing sample of the individual and the individual did not have rheumatoid arthritis at the time of sampling; and
  treating the individual, preferably with a rheumatoid arthritis medicament or other targeted intervention prior to or at the onset of the individual presenting with a rheumatoid arthritis symptom. The treatment prevents or at least delays the onset of chronic arthritis, and/or the onset of a rheumatoid arthritis symptom. The treatment may also reduce the severity of the chronic arthritis, and/or rheumatoid arthritis symptom.

Also provided is a method of treating an individual for a rheumatoid arthritis symptom or the development thereof, the method comprising:

determining whether a sample contains an AMPA, preferably an AAPA, ACPA and/or anti-CarP antibody; and determining whether the antibody has an N-linked glycosylated Fab-portion;

wherein the sample is an antibody-containing sample of the individual and the individual did not have rheumatoid arthritis at the time of sampling; and treating the individual with a rheumatoid arthritis medicament prior to or at the onset of the individual presenting with a rheumatoid arthritis symptom.

Also provided is a method of monitoring an individual at risk of developing arthritis, the method comprising monitoring the presence and/or the onset of an AMPA, preferably an ACPA, an anti-CarP and/or an AAPA antibody in periodic antibody-containing samples of the individual, wherein the method further comprises determining whether a detected AMPA, preferably ACPA, anti-CarP and/or AAPA antibody comprises an N-linked glycan at one or more positions in a Fab-portion of the antibody.

Further provided is a medicament, preferably an arthritis medicament, for use in a method of treatment of an individual comprising determining the presence of an AMPA, preferably an AAPA, ACPA and/or anti-CarP antibody, that comprises N-linked glycosylation at one or more positions in a Fab-portion of the antibody in an antibody-containing sample of the individual, and treating the individual when an AMPA that comprises N-linked glycosylation at one or more positions in a Fab-portion of the antibody has been detected.

Further provided is a method of determining whether an individual comprises an autoantibody associated with rheumatoid arthritis, Sjögren syndrome or AAV with an N-linked glycan on a Fab-portion of the antibody, the method comprising:

contacting a B-cell-containing sample of the individual with a peptide or protein that can bind the autoantibody;

separating B-cells bound to the peptide or protein from unbound B-cells; and sequencing nucleic acid encoding the variable region of a heavy chain or a part thereof and/or the variable region of a light chain variable region or a part thereof of an antibody or B-cell receptor of the bound B-cells; and determining whether the nucleic acid sequence codes for an N-linked glycosylation consensus amino acid sequence.

Further provided is a method of determining whether an individual comprises an anti-modified protein antibody (AMPA) with an N-linked glycan on a Fab-portion of the antibody, the method comprising:

contacting a B-cell-containing sample of the individual with a peptide or protein that comprises a modified protein epitope;

separating B-cells bound to the peptide or protein from unbound B-cells; and sequencing nucleic acid encoding the variable region of a heavy chain or a part thereof and/or the variable region of a light chain variable region or a part thereof of an antibody or B-cell receptor of the bound B-cells; and determining whether the determined nucleic acid sequence codes for an N-linked glycosylation consensus amino acid sequence.

The part of the variable region can be any part, such as, but not limited to, a framework region, such as FR1, FR2, FR3, or FR4. The part can also be a complementarity-determining region (CDR) such as CDR1, CDR2 or CDR3. The part of the variable region of the heavy chain is preferably a CDR of the variable region, preferably the CDR1, preferably CDR1 and CDR2, preferably all of the CDRs. The part of the variable region of the light chain is preferably a CDR of the variable region, preferably the CDR1, preferably CDR1 and CDR2, preferably all of the CDRs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: Nomenclature of glycans found on ACPA-IgG and IgG. G2S2, G2FS1B, G2FS2, G2S2B, G2FS2B are considered as Fab-glycans because these glycan structures are highly expressed by Fab fragments of ACPA-IgG and IgG, whereas these structures are low- or not expressed on Fc fragments.

FIGS. 3A-3C: Approach A (method 2) SNA, a lectin that specifically binds to alpha2,6-linked sialic acids found on Fab-glycan structures binds to ACPA purified from serum of RA patients. FIG. 3A: Method to first capture ACPA with CCP2-coated beads from serum of ACPA-positive and ACPA-negative RA patients (left). Next, the ACPA-positive elution was added to an ELISA plate coated with anti-human-IgG. In the next step, biotinylated-SNA was added to the bound ACPA-IgG to analyze levels of Fab-glycosylation of ACPA (right). As control for the amount of ACPA that was present in each well, a total IgG ELISA was performed (data not shown). FIG. 3B: The ratio glycosylated ACPA-Fab/total ACPA-IgG (for methods, see FIG. 3A) demonstrated a high number of Fab-linked glycans on ACPA from ACPA-positive patients, whereas the CCP-coated elution from ACPA-negative patients did not demonstrate SNA binding. FIG. 3C: To prove that SNA in our ELISA as depicted in FIG. 3A (right) specifically binds to Fab-glycosylated antibodies, a commercially available IVIg (Sanquin) was used. IVIg was incubated with SNA-coated beads and the flow through (FT1) or the elution 1 (E1; eluted with PBS and lactose) or elution 2 (E2; eluted with lactose in acetic acid which is supposed to contain Fab-glycosylated antibodies) were added on an ELISA plate coated with anti-human IgG. Levels of Fab glycosylation on IgG were determined by SNA binding to the different fractions (ELISA method depicted in FIG. 3A, right). Indeed, SNA binding was highest to the fraction that contained Fab-glycosylated antibodies. An additional HPLC analysis with the fractions confirmed the finding.

FIGS. 4A.1-4B: (FIGS. 4A.1 and 4A.2) Approach B (method 3): first capturing sialylated antibodies and next detection of ACPA enrichment. Methodology to assess ACPA-IgG Fab glycosylation using protein G and, subsequently SNA agarose beads. The right panel demonstrates enrichment of Fab-glycosylated ACPA in a set of serum samples of ACPA-positive RA patients. (FIG. 4B) ACPA and anti-CarP antibodies are captured by SNA. IgG was isolated from serum of ACPA- and anti-CarP antibody-positive RA patients by prot G beads. By SNA agarose beads, the SNA-binding IgG antibodies were isolated and resulted in an SNA-binding (eluate) and non-SNA-binding (flow through) fraction (left panel of FIG. 4A.1. The SNA+ fraction (eluate left panel of FIG. 4A.1) or the SNA-negative fraction (flow through left panel of FIG. 4A.1) were added to an ELISA plate either coated with CCP2 (left; to detect ACPA) or carbamylated FCS (right; to detect anti-CarP antibodies) and IgG binding was analyzed. Indeed, the SNA+ fraction contained ACPA and anti-CarP auto-antibodies, suggesting that Fab-glycosylation is elevated on ACPA and anti-CarP antibodies compared to general IgG.

FIG. 6: Amino acid sequence (SEQ ID NO:1) of fibrinogen alpha.

FIG. 7: Amino acid sequence (SEQ ID NO:2) of fibrinogen beta.

FIG. 8: Amino acid sequence (SEQ ID NO:3) of fibrinogen gamma.

FIGS. 9A-9C: Scheme of the purification and analysis of the glycosylation of ACPA-IgG and IgG. FIG. 9A) ACPA antibodies were purified by affinity chromatography on CCP2 (citrullinated cyclic peptide (CCP Cit) or the arginine control (CCP-Arg) followed by Protein G and Protein A capture to obtain ACPA $IgG_{1,2,4}$ as well as non-citrulline-specific $IgG_{1,2,4}$ (depleted of ACPA). FIG. 9B) (ACPA)-IgG F(ab')2 fragments were generated by digesting purified antibodies with Ides. The resulting Fc part was purified using anti-Fc antibodies, whereas the F(ab')2 fragments were isolated using anti-CH1 domain antibodies. FIG. 9C) The N-glycans of antibodies and fragments were labelled with 2-aminobenzoic acid (2AA) and analyzed by UHPLC and MALDI-TOF-MS, whereas the glycopeptides were analyzed by LC-MS.

FIG. 10A) SDS-PAGE of ACPA-IgG and IgG under reducing condition. Compared to NCS-IgG exhibiting one HC and one LC, ACPA-IgG showed multiple HC (HC1 to HC3) and LC bands (LC to LC2) due to N-linked glycosylation. FIG. 10B) UHPLC chromatograms of the N glycans extracted from the different electrophoretic bands.

(FIG. 12A) UHPLC chromatograms of ACPA-IgG and IgG F(ab')2 glycans of a representative RA patient. (FIG. 12B) Differences in glycan-derived traits of ACPA-IgG and IgG Fab glycosylation represented in the relative abundance of galactosylation, sialylation, fucosylation.

FIGS. 13A-13C: ACPA-IgG are highly Fab-glycosylated compared to non-citrulline-specific IgG. (FIG. 13A) MALDI-TOF-MS spectra of ACPA-IgG and IgG (FIG. 13B) Comparison of ACPA-IgG and IgG Fab glycosylation levels derived from UHPLC and LC-MS data. (FIG. 13C) Comparison of the Fab glycosylation of ACPA-IgG or non-citrulline-specific IgG from synovial fluid (n=3) and plasma (n=6).

FIG. 14: Amino acid sequences of VH (SEQ ID NO:4, SEQ ID NO:6, SEQ ID NO: 8) or VL (SEQ ID NO:5, SEQ ID NO:7, SEQ ID NO:9) regions comprising an exposed N-linked glycosylation consensus site(s), which are highlighted and underlined.

FIG. 16: human albumin is sensitive to post-translational modifications such as citrullination and carbamylation. Figure depicts the sequence of the human albumin protein accession code Q56G89 of the Uniprot database (SEQ ID NO:10).

FIG. 17: human alpha-1-antitrypsin is sensitive to post-translational modifications such as carbamylation. Figure depicts the sequence of human alpha-1-antitrypsin accession code AAB59375.1 in the NCBI database (SEQ ID NO: 11).

(FIG. 19A) IgG heavy chain (FIG. 19B) Ig kappa light chain (FIG. 19C) Ig lambda light chain.

FIG. 21A) The FDR RA individuals have a higher ACPA-IgG Fab glycosylation whereas the FDR HC keeps normal levels of ACPA-IgG Fab glycosylation.

FIG. 21B) The ACPA-IgG Fab glycosylation is already high before the disease onset. FIG. 21C) Whereas the ACPA-IgG Fab glycosylation of FDR HC stays low over time.

FIG. 24A) UHPLC chromatogram of the released and 2AA-labelled glycans of ACPA-IgG where a glycan peak was eluting after the already reported GP24 glycan peak. By collecting the GPx, LC-MS was performed to investigate the masses present in this peak fraction. It was determined that the peak was corresponding to a glycan with a mass of N5H6F1S2. FIG. 24B) conformation of the structure with MALDI-TOF-MS-MS. The mass 2812.792 is corresponding with the glycan mass of N5H6F1S2 and by fragmentation a tri-antennary glycan with two a2.6 linked sialic acids was confirmed.

DETAILED DESCRIPTION

Figure 1B:
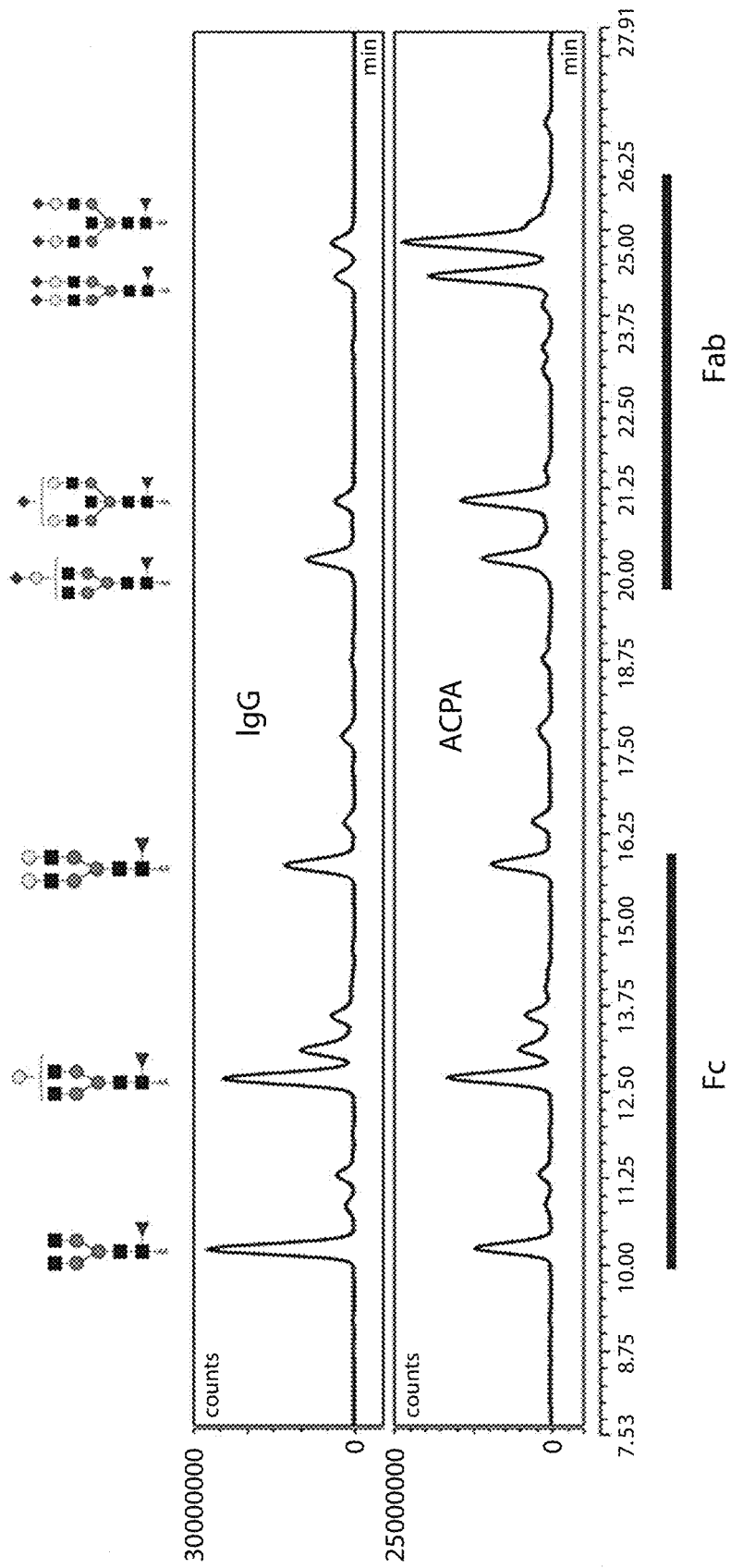
FIG. 1B: Typical profile of glycans found on total IgG (top) and ACPA IgG (bottom). IgG or ACPA were isolated from the same patients. Glycans were released and analyzed by HPLC. ACPA F(ab)-fragments contain bi-antennary N-linked glycans that are highly sialylated (purple diamonds: =sialic acid).

The individual is preferably a human individual.

An autoimmune disease is a condition arising from an abnormal immune response to a normal body part. Autoimmune diseases can affect almost any part of the body, including the heart, brain, nerves, muscles, skin, eyes, joints, lungs, kidneys, glands, the digestive tract, and blood vessels. There are at least 80 types of autoimmune diseases. Nearly any body part can be involved. Common symptoms include low grade fever and feeling tired. Often symptoms come and go.

Some autoimmune diseases such as systemic lupus erythematosus run in families, and certain cases may be triggered by infections or other environmental factors. Some common diseases that are generally considered autoimmune include celiac disease, diabetes mellitus type 1, Graves' disease, inflammatory bowel disease, multiple sclerosis, psoriasis, rheumatoid arthritis, and systemic lupus erythematosus.

Treatment depends on the type and severity of the condition. Nonsteroidal anti-inflammatory drugs (NSAIDs) and immunosuppressants are often used. Intravenous immunoglobulin may also occasionally be used. While treatment usually improves symptoms, they typically do not cure the disease.

In one embodiment is provided a method of determining whether an individual that does not have a particular autoimmune disease at the moment of sampling is at risk of developing that particular autoimmune disease, the method comprising determining whether an antibody-containing sample of the individual comprises an autoantibody that is associated with the particular autoimmune disease and determining whether the autoantibody comprises an N-linked glycosylation at one or more positions in a Fab-portion of the autoantibody, the method further comprising determining the risk of the individual for developing the particular autoimmune disease on the basis of the determinations.

The risk of the individual for developing the particular autoimmune disease is high when the autoantibody that is associated with the particular autoimmune disease is detected and the antibody comprises an N-linked glycosylation at one or more positions in a Fab-portion of the autoantibody. The risk is higher when a higher fraction of the autoantibody comprises an N-linked glycosylation at one or more positions in a Fab-portion.

In one embodiment, a method of analyzing an antibody-containing sample of an individual is provided wherein the method comprising determining whether the sample comprises an autoantibody that is associated with a particular autoimmune disease and which autoantibody comprises an N-linked glycosylation at one or more positions in a Fab-portion of the antibody, wherein the sample is a sample of an individual that does not have symptoms of the particular autoimmune disease at the moment of sampling.

Also provided is a method of treating an individual for a particular autoimmune disease symptom or the development thereof, the method comprising:
  determining whether a sample contains an autoantibody that is associated with the particular autoimmune disease; and
  determining whether the antibody has an N-linked glycosylated Fab-portion;
  wherein the sample is an antibody-containing sample of the individual and the individual did not have the autoimmune disease at the time of sampling; and
  treating the individual with a medicament for the treatment of the particular autoimmune disease prior to or at the onset of the individual presenting with a symptom for the particular autoimmune disease.

Further provided is a method of monitoring an individual at risk of developing a particular autoimmune disease, the method comprising monitoring the presence and/or the onset of an autoantibody associated with the particular autoimmune disease in periodic antibody-containing samples of the individual, wherein the method further comprises determining whether the autoantibody comprises an N-linked glycan at one or more positions in a Fab-portion of the antibody.

Also provided is a medicament for use in a method of treatment of an individual comprising determining the presence of an autoantibody associated with a particular autoimmune disease and that comprises N-linked glycosylation at one or more positions in a Fab-portion of the antibody in an antibody-containing sample of the individual, and treating the individual when an autoantibody associated with the particular autoimmune disease that comprises N-linked glycosylation at one or more positions in a Fab-portion of the antibody has been detected.

In one embodiment, the autoimmune disease is one or more of Sjögren syndrome; anti-neutrophil cytoplasmic antibodies (ANCA)-associated vasculitis (AAV); and arthritis. The arthritis is preferably rheumatoid arthritis. Sjögren syndrome is associated with a number of other medical conditions, many of which are autoimmune or rheumatic disorders, such as celiac disease, SLE (lupus), autoimmune thyroiditis, multiple sclerosis and spondyloarthropathy. Sjögren syndrome is also associated with non-Hodgkin lymphoma. Where reference is made herein to Sjögren syndrome in the context of the present disclosure, the reference is to primary Sjögren syndrome only. The typical autoantibodies with specificity for Sjögren's syndrome are SS-A and SS-B. The reference to primary Sjögren syndrome is with the exclusion of secondary Sjögren syndrome, which is associated with various auto-immune diseases.

An autoantibody is an antibody that is directed against one or more of the individual's own proteins (is directed toward a self-antigen). Autoantibodies can be directed toward a number of different self-antigens. An autoantibody is said to be associated with an autoimmune disease if the frequency with which autoantibodies with the indicated specificity are detected in individuals having the autoimmune disease is significantly higher than in the normal/healthy population. In Sjögren syndrome, the autoantibody is typically an SS-A or SS-B antibody (also referred to as anti-Ro/La). Anti-neutrophil cytoplasmic antibody (ANCA)-associated vasculitis (AAV) is a group of autoimmune diseases characterized by the abnormal infiltration of neutrophils, accumulation of unscavenged leucocytoclasis in perivascular tissues and fibrinoid necrosis of the vessel walls. Patients with AAV frequently exhibit rapidly progressive renal failure caused by crescentic glomerulonephritis. Myeloperoxidase (MPO) and proteinase 3 (PR3) have been shown to be two major ANCA antigens. Autoantibodies in AAV are typically directed toward one or both of the proteins. The lysosomal membrane protein-2 (LAMP-2) autoantibody represents an additional ANCA subtype. In RA, the autoantibody is typically an AMPA or Rheumatoid Factor.

Sjögren syndrome is a long-term autoimmune disease in which the moisture-producing glands of the body are affected. This results primarily in the development of a dry mouth and dry eyes. Other symptoms can include dry skin, a chronic cough, vaginal dryness, numbness in the arms and legs, fatigue, muscle and joint pains, and thyroid dysfunction. Those affected are at an increased risk (5%) of lymphoma. Sjögren syndrome diagnosis is made by combining clinical symptoms, results of measurements that test glandular function, biopsy of moisture-producing glands and blood tests looking for specific antibodies. On biopsy, there are typically lymphocytes within the glands.

Vasculitis is a group of disorders that destroy blood vessels by inflammation. Both arteries and veins are affected. Lymphangitis is sometimes considered a type of vasculitis. Vasculitis is primarily caused by leukocyte migration and resultant damage. ANCA-associated vasculitis is a vasculitis subtype associated with autoantibodies against antigens derived from neutrophil granulocytes. Such anti-neutrophil cytoplasmic antibodies are also referred to as ANCA.

Arthritis is among the more common forms of autoimmune disease. There are over 100 different forms of arthritis. The most common form is osteoarthritis (degenerative joint disease). Osteoarthritis has a variety of causes, albeit that there are also not readily identifiable causes. The latter are often collectively referred to as age-related osteoarthritis. Other arthritis forms are, for example, rheumatoid arthritis, psoriatic arthritis, and related autoimmune diseases.

A major complaint of individuals who have arthritis is joint pain. Pain is often constant and may be localized to the joint affected. The pain from arthritis is often the result of the damage that is induced to the joint or the result of the inflammation that occurs in and around the joint. Other complaints are pain as a result of muscle strains caused by forceful movements against stiff, painful joints and fatigue. Rheumatoid arthritis is a debilitating and progressive disease if left untreated. Symptoms of disease and treatments for RA are detailed in Scott et al., 2010, *The Lancet* 376, pp. 1094-1108, which is incorporated by reference herein. The present disclosure refers to this publication, in particular, for the description of symptoms of RA and RA medicaments. Although the review is extensive, the described symptoms and medicaments should not be read as limitative. A summary non-limitative list of symptoms is given herein below. Rheumatoid arthritis affects joints. Arthritis of joints involves inflammation of the synovial membrane. Joints become swollen, tender and warm, and stiffness limits their movement. Most commonly involved are the small joints of the hands and feet, but larger joints like the shoulder and knee and the cervical spine can also be involved. RA typically manifests with signs of inflammation, with the affected joints being swollen, warm, painful and stiff, particularly early in the morning on waking or following prolonged inactivity. Increased stiffness early in the morning is often a prominent feature of the disease and typically lasts for more than an hour. As the pathology progresses, the inflammatory activity leads to tendon tethering, erosion and destruction of the joint surface. This impairs the range of movement and leads to deformity. The rheumatoid nodule, which is sometimes in the skin, is the most common non joint feature. They occur in a large minority of the patients. It is a type of inflammatory reaction known to pathologists as a "necrotizing granuloma."

Anti-citrullinated protein antibodies (ACPA) are autoantibodies (antibodies to an individual's own proteins). The antibodies are directed against peptides and/or proteins that are citrullinated. They are present in the majority of patients with rheumatoid arthritis. Clinically, cyclic citrullinated peptides (CCP) are frequently used to detect these antibodies in patient serum or plasma.

Citrullination or deimination is the conversion of the amino acid arginine in a protein into the amino acid citrulline. Enzymes called peptidylarginine deiminases (PADs) replace the primary ketimine group (=NH) by a ketone group (=O). Citrullination performs a function in normal individuals. However, the immune system can attack citrullinated proteins, which happens specifically in rheumatoid arthritis.

Citrulline is not one of the 20 standard amino acids encoded by DNA in the genetic code. Instead, it is the result of a post-translational modification. Citrullination is distinct from the formation of the free amino acid citrulline as part of the urea cycle or as a by-product of enzymes of the nitric oxide synthase family.

Arginine is positively charged at a neutral pH, whereas citrulline is uncharged. In the reaction from arginine to citrulline, one of the terminal nitrogen atoms of the arginine side chain is replaced by an oxygen. The change in charge increases the hydrophobicity of the protein, leading to changes in protein folding. Therefore, citrullination can change the structure and function of proteins. Fibrin and fibrinogen may be favored sites for arginine deimination within rheumatoid joints.

Tests for the presence of ACPA-IgG are about as sensitive as IgM rheumatoid factor for the diagnosis of RA. Such ACPA are detectable before the onset of clinical disease. ACPA tests are presently routinely incorporated in the diagnostic scheme for RA. However, considering that such antibodies can be present for years prior to development of disease, they are not on their own conclusive.

Homocitrulline is one methylene group longer than citrulline, but similar in structure. The metabolite is generated from a lysine residue. It is believed that most carbamylation during inflammation takes place when the enzyme MPO is released from neutrophils. Autoantibodies against homocitrullinated peptides and proteins (anti-CarP) are associated with RA. Anti-CarP antibodies can be detected also in pre-symptomatic individuals long before symptoms develop (Shi et al., *Ann. Rheum. Dis.* 2014 April, 73 (4): 780:3).

Citrullination and carbamylation are examples of post-translational modifications of proteins to which auto-antibodies can be produced by individuals. Lysine acetylation is another post-translational modification to which individuals can produce auto-antibodies (Juarez, et al., 2015, Annals of the rheumatic diseases: annrheumdis—2014). Acetylation occurs as a post-translational modification of a protein, for example, histones, p53, and tubulins. Among these proteins, chromatin proteins and metabolic enzymes are highly represented. Acetylation is sometimes also referred to as a co-translation modification. In the present disclosure, it is referred to as a post-translational modification. Proteins can be acetylated on lysine residues. Lysine acetylation is thought to have a regulatory function in at least some types of proteins. Lysine acetylation modifies the end of the side chain of lysine. Where the side chain of lysine ends in-NH2, an acetylated lysine ends in NH=O—CH3.

Other types of post-translational modifications include, but are not limited to, phosphorylation, methylation, ubiquitination, glycosylation and/or sumoylation. In the present disclosure, the post-translational modification that is detected by auto-antibodies is typically not a glycosylation. Preferred post-translational modifications are citrullination, homo-citrullination and lysine acetylation. A peptide or protein with a post-translational modification is also referred to as a modified peptide or protein, or a peptide or protein comprising a modified epitope. An antibody that specifically binds an epitope that comprises a post-translational modification is referred to as anti-modified protein antibody (AMPA). The AMPA binds the peptide or protein only when it comprises the post-translational modification. Such a modified epitope is also referred to as a modified protein epitope. An AMPA is an antibody that can bind a post-translationally modified epitope in a peptide or protein. The AMPA is typically not an antibody that binds a glycosylated epitope. The AMPA is preferably an antibody that binds an epitope comprising a citrulline, a homocitrulline and/or an acetylated lysine. In recent years, it has become apparent that auto-immunity in RA targets citrullinated proteins and extends to other protein modifications such as protein homo-citrullination, also known as carbamylation, and acetylation (Shi et al., *Proc. Natl. Acad. Sci.* 2011, 108:17372-17377; Juarez et al., *Ann. Rheum. Dis.*, 2016, 75:1099-1107). In another aspect, the AMPA is an antibody that binds an MAA-adduct on a protein. Preferred epitopes that the AMPA can bind are epitopes comprising a citrulline, a homo-citrulline, an acetylated lysine residue and/or a malondialdehyde-acetaldehyde adduct. Preferred epitopes that the AMPA can bind are epitopes comprising a citrulline, a homo-citrulline and/or an acetylated lysine residue. The post-translationally modified epitope in a peptide or protein can be a normal peptide or protein that is generated and subsequently modified. The post-translationally modified epitope can also be introduced directly into the peptide or protein during artificial synthesis of the peptide or, if desired, the protein, using an artificial amino-acid comprising the desired side chain.

In the present disclosure, it was found that detection of an AMPA, with N-linked glycosylation at one or more positions in the Fab-portion of the antibody correlated well with the onset of rheumatoid arthritis. The AMPA is preferably an antibody that can bind a citrullinated, or a homo-citrullinated and/or an acetylated lysine epitope in a peptide or protein. The antibody is preferably an ACPA, an anti-CarP and/or an AAPA antibody. It is known that the presence of AAPA, ACPA or anti-CarP antibodies is indicative for a risk of developing the disease. However, such antibodies and, in particular, AAPA, ACPA and anti-CarP antibodies, can generally be present for years prior to development of RA. On the other hand, N-linked glycosylation at one or more positions in the Fab-portion of such antibodies more accurately predicts the onset of disease and the development of symptoms. The moment that an AMPA comprising N-linked glycosylation at one or more positions in the Fab-portion appears in serum is indicative for the appearance of symptoms and development of the disease. The same phenomenon was detected in individuals at risk of developing Sjögren syndrome or AAV. Knowledge of the imminence of the appearance of symptoms is advantageous as early treatment of Sjögren syndrome, AAV or RA symptoms with, for instance, disease-modifying antirheumatic drugs (DMARDs) in the case of RA has been shown to be beneficial to the patients. Also, pre-symptomatic treatment is likely to be beneficial to the individual in the long term. RA symptoms can at least be delayed, and/or the severity of the symptoms can be ameliorated when compared to those of patients that were not treated or received treatment after the onset of RA symptoms. It is also possible that pre-disease treatment prior to the appearance of Fab-glycosylated antibodies that can bind a post-translationally modified epitope in a peptide or protein such as an AAPA, ACPA and/or anti-CarP antibodies could prevent the development of RA.

N-linked glycosylation is a post-translational modification that can occur at certain amino-acid motifs in a protein. The first ACPA and anti-CarP antibodies to appear in the blood typically do not have glycans in the Fab-portion of the antibody and lack a suitable consensus sequence. N-glycans attach to an asparagine, which must be located in a specific consensus sequence in the primary structure (Asn-X-Ser; Asn-X-Thr or, in rare instances, Asn-X-Cys; X may not be proline). The Asn must be located on the surface of the antibody and the Asn must be found in the luminal side of the endoplasmic reticulum for N-linked glycosylation to be initiated. Motifs that meet these criteria often only appear upon maturation of the antibody by means of somatic hypermutation.

The present disclosure provides a method for determining whether an individual comprises an antibody that comprises an N-linked glycosylation in a Fab-portion of the antibody, the method comprising amplifying nucleic acid molecules that code for an antibody VH and/or VL or portion thereof in a sample comprising B-cells of the individual and determining whether an amplified nucleic acid molecule codes for an amino acid sequence that is an N-linked glycosylation consensus site. The three-dimensional structure of Fab-portions of an antibody is well known. It is also known which part of the amino acids in a Fab-portion of an antibody are exposed and, therefore, accessible (exposed to the outside of the molecule) to post-translational N-linked modification. In a preferred embodiment of a method as described, it is determined whether an amplified nucleic acid molecule comprises a sequence that codes for an accessible consensus site for N-linked glycosylation. In a preferred embodiment, the B-cells are B-cells that comprise a B-cell receptor (BCR) that can bind a post-translationally modified epitope in a peptide or protein. The presence of such a BCR indicates that the individual comprises an AMPA. Such B-cells can be purified from a B-cell population on the basis of the modified protein binding capability of the B-cell; for instance, by means of beads that have a modified protein epitope on their surface. It has been found that accessible consensus sites for N-linked glycosylation are not randomly distributed over the VH or VL region. Such consensus sites can be a clustered framework region, such as FR1, FR2, FR3, or FR4, both in the heavy chain and the light chain. The part can also be a complementary-determining region (CDR) such as CDR1, CDR2 or CDR3. In some embodiments, consensus sites are clustered around the CDR regions, most often in or around the CDR1 region or the CDR3 region of the VH or VL, typically in or around the CDR1 region. It is, therefore, preferred that the sequence of at least the VH CDR1 is determined, preferably the VH CDR1 and the VL CDR1; preferably at least further including determining the VH CDR3, preferably the VH CDR3 and the VL CDR3. Preferably, at least the VH sequence is determined; preferably both the VH and the VL sequences are determined. In one embodiment, the disclosure provides a method for determining whether an individual comprises an AMPA that comprises an N-linked glycosylation in a Fab-portion of the antibody; the method comprising collecting B-cells with B-cell receptors that comprise an AMPA from the individual; amplifying nucleic acid molecules that code for the VH and/or VL or portion thereof of the AMPA and determining whether an amplified nucleic acid molecule codes for an amino acid sequence that is an N-linked glycosylation consensus sequence. The VH and/or VL portion is preferably a CDR coding sequence, preferably a CDR1 and/or CDR3 coding sequence. For examples of the sequencing of B-cell receptors of anti-citrullinated protein antibody IgG-expressing B-cells, reference is made to Vergoesen et al., *Ann. Rheum. Dis.,* 2017, Doi: 10.1136/annrheumdis-2017-212052.

Detection of an AMPA, preferably an AAPA, ACPA or anti-CarP antibody with N-linked glycosylation at one or more positions in the Fab-portion of the antibody is typically predictive for the individual developing rheumatoid arthritis shortly after the collection of the sample. Detection of the "immunological conversion," i.e., the appearance of AMPA comprising an N-linked glycan in a Fab-portion of the antibody is preferably done as early as possible, preferably long-enough to be able to initiate effective (and ideally preventive) treatment. Detection of an AMPA with an N-linked glycan in a Fab-portion of the antibody is typically predictive for the individual developing rheumatoid arthritis within a limited time frame from collection of the sample from the individual.

In one aspect, the disclosure provides a new method of determining N-linked glycosylation at a Fab-portion of an AMPA. The method comprises contacting antibodies of a sample with a protein or peptide that comprises an epitope comprising a post-translational modification; contacting antibodies of the sample with a molecule that can bind an N-linked glycan on a Fab-portion of an antibody; and determining whether an antibody with a N-linked glycan on a Fab-portion of the antibody has bound to the epitope comprising the post-translational modification in the protein/peptide.

An epitope comprising a post-translational modification (herein referred to with the term "modified protein epitope") is preferably a citrullinated epitope, a homo-citrullinated epitope and/or an acetylated lysine epitope. Antibodies to these epitopes are referred to as ACPA, anti-CarP and AAPA, respectively. In some embodiments, the post-translational modification is an MAA or AA-adduct. Malondialdehyde (MDA) and its breakdown product acetaldehyde (AA) are highly reactive aldehydes, and together have been demonstrated to modify proteins to produce an MDA-AA protein adduct, termed malondialdehyde-acetaldehyde (MAA-adduct). MAA-adducts are highly immunogenic.

In nature, the modification can be introduced in the peptide or protein after synthesis of the peptide or protein, or during synthesis. In the latter case, the modification is introduced in the part of the protein that has already been synthesized by the ribosome. In the laboratory, it is possible to introduce the modification also by incorporating a modified version of the amino acid in the nascent amino acid chain. In the laboratory, it is preferred that the peptide or protein is synthesized in the presence of an artificial amino acid that comprises the modification, which is then incorporated into the nascent peptide or protein chain.

The sample is typically a blood sample, preferably a serum or plasma sample. Such samples are typically antibody-containing samples. Other antibody-containing samples are, for instance, synovial fluid and sputum. For sequencing purposes, it is preferred that the sample contains cells that produce the antibody. In such embodiments, it is preferred that the sample is a sample that comprises B-cells. B-cell receptor-positive B-cells contain antibodies that are excreted and/or that are present as part of the B-cell receptor on the cell surface of the B-cell. The B-cell receptor or BCR is a transmembrane receptor protein located on the outer surface of B-cells. The receptor's binding moiety is composed of a membrane-bound antibody that, like all antibodies, has a unique and randomly determined antigen-binding site. Antibody-containing samples that have BCR-positive cells can be used, for instance, to sequence the variable region of the expressed BCR or expressed antibody, for instance, to determine whether the variable domain comprises a consensus sequence for N-linked glycosylation. A B-cell-containing sample is, for instance, synovial fluid. IgG antibodies are found in all body fluids. They are the isotype most commonly used for the determination of AAPA, ACPA and anti-CarP antibodies and form a suitable source to determine glycosylation of a Fab-portion. The sample can be used directly in a method for detecting as described herein, or antibodies can be purified from the sample and are then used in the method. The sample is preferably a sample of an individual that does not have RA at the moment of sampling. Preferably, the individual does not express an RA-classifying symptom, in particular arthritis, at the moment of sampling.

Various methods are available to determine whether a sample comprises an ACPA or an anti-CarP antibody. Most methods use a protein or peptide that comprises a citrullinated or homo-citrullinated epitope. The peptide is typically a peptide of between 6-50 amino acids. Preferably, the peptide is a peptide of between 12 and 30 amino acids, more preferably of between 18 and 22 amino acids, most preferably of about 21 amino acids. The mentioned ranges include the number mentioned, i.e., a range of between 12 and 30 amino acids including 12 peptides and 30 amino acids, respectively. The peptide may or may not be a cyclic peptide depending on the sensitivity and/or specificity of the comparable linear peptide. Circular peptides can be generated in any molecular composition as to generate the cyclic nature. A protein typically comprises 30 or more amino acids; typically, 50 or more amino acids. Examples of proteins that can be used in a method of the disclosure are depicted in the figures, i.e., fibrinogen alpha (FIG. 6), fibrinogen beta (FIG. 7) or fibrinogen gamma (FIG. 8), human albumin (FIG. 16) and human alpha-1-antitrypsin (FIG. 17). Particularly preferred peptides are the CCP1 and CCP2 peptides, preferably CCP2. A kit of the disclosure preferably comprises a CCP1 and/or CCP2 peptide.

In a preferred embodiment, a peptide or protein for use in a method of the disclosure is (part of) a human protein that is known to be subject to post-translational modification such as citrullination, homo-citrullination and/or acetylation in patients with RA. In a preferred embodiment, the peptide is a peptide derived from human fibrinogen. The peptide preferably comprises a contiguous amino acid of between 12 and 30 amino acids, more preferably of between 18 and 22 amino acids, most preferably of about 21 amino acids present in the amino acid sequence of any one of fibrinogen alpha (FIG. 6), fibrinogen beta (FIG. 7) or fibrinogen gamma (FIG. 8). In another preferred embodiment, the peptide is a peptide derived from human albumin (FIG. 16) or human alpha-1-antitrypsin (FIG. 17). The peptide or protein comprises an epitope with a post-translational modification. The epitope is preferably an epitope with at least one lysine (anti-CarP or AAPA) or arginine (ACPA) present in an unmodified protein, is now a citrulline, an acetylated lysine or a homo-citrulline. The acetylated lysine, citrulline or homo-citrulline can be introduced by the appropriate acetylation or (homo)-citrullination of a peptide. More suitably, the peptide is synthesized with the acetylated lysine, citrulline or homo-citrulline at the correct position.

The peptide, protein or the molecule that can bind an N-linked glycan on a Fab-portion of an antibody is typically coupled to a surface. The surface is typically a solid surface. The solid surface can be a flat surface as typically present in a plate. It can also be a three-dimensional structure such as a bead. The solid surface may also be gel-matrix. A solid surface to which antibodies can be bound facilitates easy separation of specific material and non-specific material. Any method may be used to couple peptides and/or proteins in carbamylated, citrullinated or native form to the surface. Non-limiting examples are direct coating or biotin-streptavidin coating. Other methods to couple peptides or proteins to a surface are available to the person skilled in the art.

Figure 20:
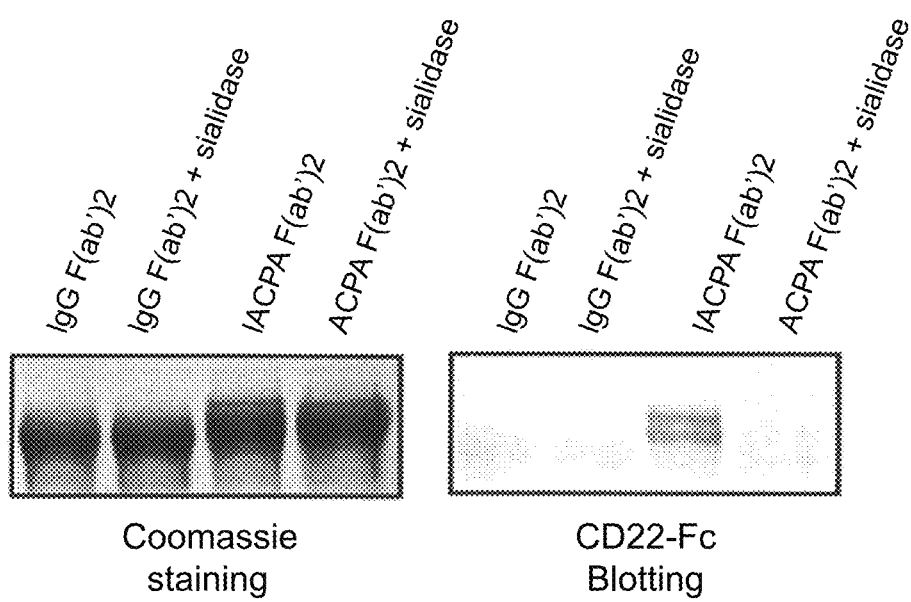
FIG. 20: CD22 as alternative for SNA to detect ACPA Fab glycans. F(ab')2 fragments of ACPA-IgG and IgG isolated from RA patients were loaded in equal amounts on gel (left panel). Next, an SDS-PAGE was performed where ACPA-IgG and IgG F(ab')2 fragments were loaded and thereafter blotted on a membrane. After this, the membrane was incubated with CD22-Fc and then stained with labelled anti-human-Fc (right panel). Only reactivity was shown for ACPA-IgG and the reactivity was gone when sialic acid was removed with sialidase.
Figure 21A:
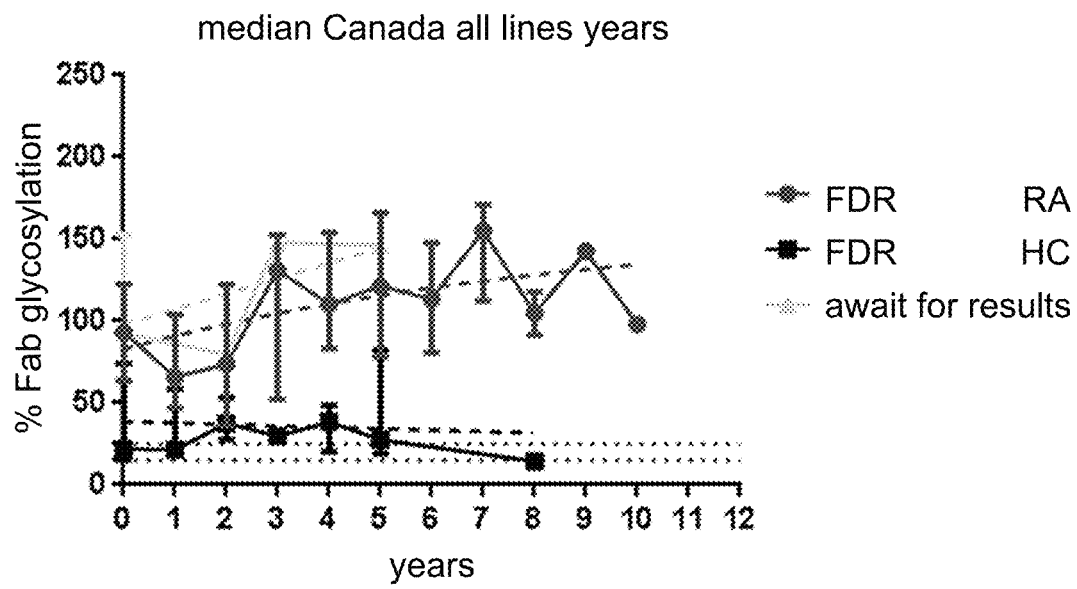
FIGS. 21A-21C: Correlation ACPA-Fab glycosylation and RA development. Analysis of the ACPA-IgG Fab-glycosylation in ACPA+ indigenous North American population first degree relatives (FDR) that developed RA (FDR RA) overtime and in ACPA+ FDR that did not develop RA (FDR HC) thus far.
Figure 21B:
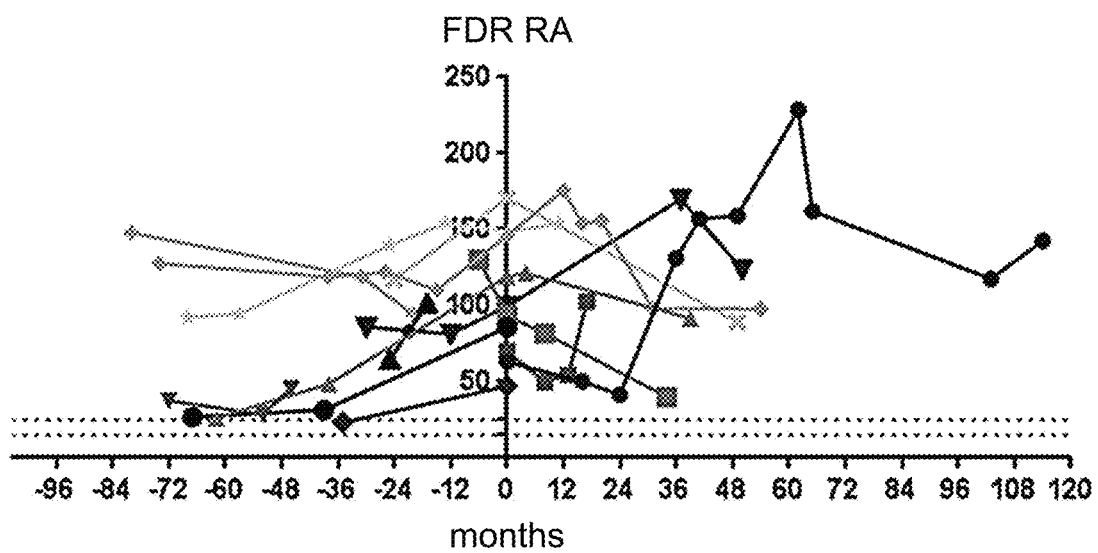
Figure 21C:
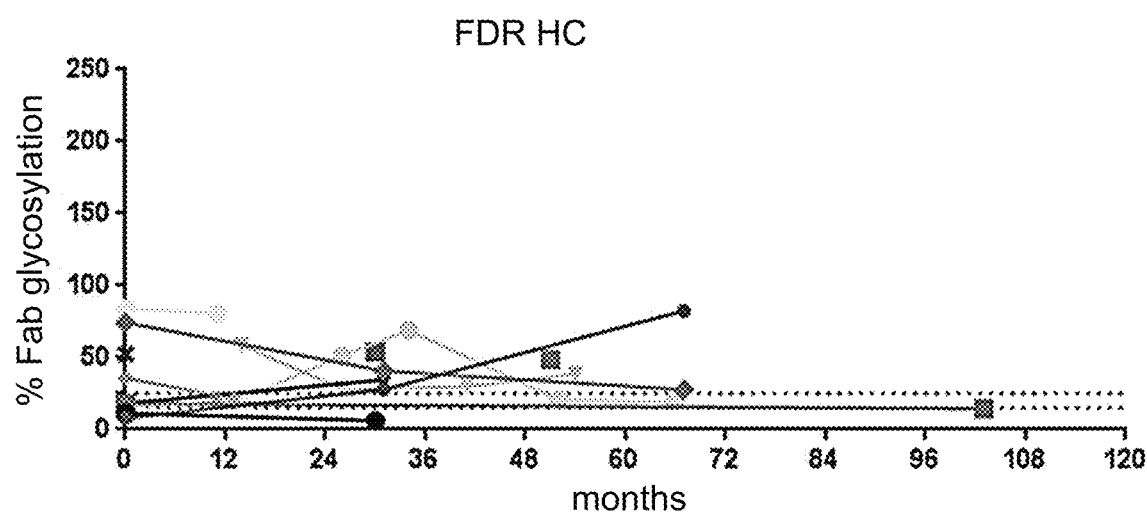

Various molecules are available that can bind an N-linked glycan on a Fab-portion of an antibody. Examples of natural proteins that can bind glycans can be found at the Functional Glycomics homepage on at the World-Wide Web functionalglycomics.org/glycomics/molecule/jsp/gbpMolecule-home.jsp). SIGLECs (Sialic acid-binding immunoglobulin-type lectins) are a family of cell surface proteins that bind sialic acid. They are found primarily on the surface of immune cells and are a subset of the I-type lectins. There are 14 different mammalian Siglecs, providing an array of different functions. The family was previously numbered SIGLEC1, SIGLEC2, . . . . SIGLEC14. Presently, many SIGLECs have been renamed. CD22 or cluster of differentiation-22, is also known as SIGLEC2. It is found on the surface of mature B-cells and to a lesser extent on some immature B-cells. Generally speaking, CD22 is a regulatory molecule that prevents the over-activation of the immune system and the development of autoimmune diseases. Of interest in the present disclosure is the fact that CD22 is a sugar-binding transmembrane protein, which specifically binds sialic acid with an immunoglobulin (Ig) domain located at its N-terminus. FIG. 20 shows the specific N-glycan modified Fab binding characteristics of a CD22-Fc molecule wherein at least the sialic acid-binding domain is physically linked to an Fc tail. A sialic acid-binding part of a SIGLEC typically contains the extracellular part of the respective SIGLEC. Fc hybrids can, for instance, be made easily. A preferred SIGLEC is CD22. Antibodies are another source of molecules that can bind N-linked glycans. Lectins are preferred molecules. Most lectins can easily be produced and many are indeed commercially available. The antibody or lectin is preferably a sialic acid-binding antibody or a sialic acid-binding lectin, preferably a sialic acid-binding lectin. A description of various members of the sialic acid family of monosaccharides, structural diversity, and linkage to the underlying glycan chain is given in A. Varki, R. D. Cummings, and J. D. Esko, et al., editors (2009), *Essentials of Glycobiology*, chapter 14, 2nd edition, Cold Spring Harbor (NY): Cold Spring Harbor Laboratory Press. The chapter also describes various sialic acid-binding lectins and their specificity. In the present disclosure, it has been found that *Sambucus nigra* agglutinin (SNA) and *Maackia amurensis* agglutinin (MAA) are particularly suited to distinguish Fc portion N-linked glycans from Fab-portion N-linked glycan. The sialic acid-binding lectin that can bind an N-linked glycan on a Fab-portion of an antibody therefore preferably comprises SNA or MAA, preferably SNA (Stadlmann et al., *Journal of Clinical Immunology*, 2010, 30 (S1): 15-9). For the sake of clarity, *Maackia amurensis* agglutinin is abbreviated with MAA whereas MAA-adduct stands for the malondialdehyde-acetaldehyde adduct on proteins.

In a preferred embodiment, the step of contacting antibodies of the sample with a peptide or protein that comprises an epitope with a post-translational modification such as an acetylated lysine epitope or a citrullinated or homo-citrullinated epitope is performed with a peptide or protein that is coupled to a surface. The peptide/protein bound fraction is preferably washed to remove unbound material. The peptide/protein bound fraction containing the preferably AAPA, ACPA and/or anti-CarP antibodies, if any, is then collected and contacted with a molecule that can bind an N-linked glycan on a Fab-portion of an antibody. Subsequently, it can be determined if the sample contained ACPA and/or anti-CarP antibodies with N-linked glycans on a Fab-portion thereof. This can be done in various ways. Preferably, this is done by contacting the molecule-containing sample with a molecule that binds human antibodies, preferably human IgG. Unbound molecule is subsequently washed and bound and, if any, can be detected with a label. Preferably, the molecule comprises the label. If the label is detected, it is determined that an antibody with a N-linked glycan on a Fab-portion of the antibody has bound to the citrullinated epitope (ACPA) or a homo-citrullinated epitope (anti-CarP) in the peptide, and that thus the sample contained ACPA and/or anti-CarP with N-linked glycan on a Fab-portion thereof.

In another preferred embodiment, the method of determining whether an antibody-containing sample comprises an AMPA, preferably an antibody that can bind an acetylated lysine epitope, a citrullinated or homo-citrullinated epitope in a peptide, comprises:
  contacting antibodies of the sample with a molecule that can bind an N-linked glycan on a Fab-portion of an antibody and collecting bound antibodies, and
  contacting collected antibodies, if any, with a peptide or protein that comprises a post-translationally modified epitope, preferably an acetylated lysine epitope, a citrullinated or homo-citrullinated epitope.

In a preferred embodiment, antibodies of the sample are first separated from other material in the sample and collected by contacting the sample with a molecule that binds human antibodies. In this way, other molecules that may comprise N-linked glycans are not entered into the method. Subsequently, it can be determined if the sample contained AMPA, preferably AAPA, ACPA and/or anti-CarP antibodies with N-linked glycan on a Fab-portion thereof. This can be done in various ways. Preferably, this is done by a method that comprises an ELISA specific for AMPA, preferably specific for AAPA, ACPA and/or anti-CarP. Antibodies of the sample are preferably contacted with a peptide/protein that comprises an acetylated lysine, a citrullinated or homo-citrullinated epitope. The peptide/protein is preferably coupled to a surface. Bound antibodies are subsequently detected by means of a molecule that can bind human antibodies, preferably IgG. The molecule preferably comprises a label.

In a preferred embodiment, antibodies of the sample are first separated from other material in the sample and collected by contacting the sample with a molecule that binds human antibodies. In this way, other molecules that may comprise N-linked glycans are not entered into the procedure.

The disclosure further comprises a method for determining whether an antibody sample of an individual comprises an AMPA, preferably an AAPA, an ACPA and/or anti-CarP antibody that has N-linked glycan on a Fab-portion, wherein the N-linked glycan on a Fab-portion is detected using a molecule that can bind N-linked glycans on a Fab-portion of an antibody, preferably a sialic acid-binding molecule, preferably SNA or MAA.

The step of detecting an N-linked glycan on a Fab-portion of the antibody can be advantageously done by contacting the antibody or a Fab-portion thereof with a molecule that specifically binds sialic acid as indicated herein. This facilitates high throughput testing of antibody-containing samples. One can also perform mass spectrometry on glycan preparations obtained from purified antibody preparations. As indicated in various figures of the present disclosure, mass spectrometry of such preparations yields spectra that disclose the structure of the glycans obtained from the antibody. The sialic acid-containing glycans can easily be discriminated in such spectra. The autoantibody or antigen-binding fragment thereof can be purified from other antibodies in a preparation, for instance, by allowing binding to specific antigen coated on beads followed by one or more washes to remove unbound antibody. N-linked glycans can be collected from such beads or eluted antibody (fragments) by enzymatic cleavage as demonstrated in the examples. The collected glycans can subsequently be identified by means of mass spectrometry. Where mass spectrometry used to be a time-consuming endeavor, it is now rapidly being optimized and streamlined so that becomes useful for medium to high throughput applications. Examples of suitable mass spec systems are the systems marketed by Waters, for instance, under the tradename Glycoworks RapiFluor-MS N-Glycan kit.

The molecule that can bind a human antibody can be an antibody, for instance, a goat anti human IgG antibody. Other molecules are protein A and protein G. Protein A is a 42 kDa surface protein originally found in the cell wall of the bacteria *Staphylococcus aureus*. Protein G is an immunoglobulin-binding protein expressed in group C and G Streptococcal bacteria much like Protein A but with differing binding specificities.

The disclosure further comprises a kit of parts useful in the detection of, preferably, a citrulline, a homo-citrulline and/or an acetylated lysine binding AMPA, preferably an AAPA, ACPA and/or antiCarP antibody in a sample. The kit preferably comprises a peptide that comprises an epitope with a post-translational modification, preferably an acetylated lysine epitope, a citrullinated or homo-citrullinated epitope and a molecule that can bind an N-linked glycan on a Fab-portion of an antibody. The peptide or the molecule that can bind an N-linked glycan is preferably linked to a surface. The kit preferably further comprises a molecule that can bind a human antibody. The molecule that can bind an N-linked glycan on a Fab-portion of an antibody is preferably a sialic acid-binding lectin, preferably SNA or MAA, preferably SNA. The molecule preferably comprises a label.

The antibody sample is preferably a sample of an individual; preferably, of an individual that does not have RA, Sjögren syndrome or AAV. In a preferred embodiment, the sample is a sample from an individual of which an earlier sample tested positive for the presence of an autoantibody associated with the disease such as an AMPA, preferably an AAPA, ACPA and/or anti-CarP antibody and in which the antibody did not comprise an N-linked glycan on a Fab-portion of the antibody. An autoantibody such as an AMPA is considered to be devoid of (or negative for) N-linked glycan on a Fab-portion of the antibody when 10% or less of the autoantibody comprises an N-linked glycan on a Fab-portion thereof. Thus, in one aspect, 10% or less of the autoantibody, preferably an AMPA, in the earlier sample comprises an N-linked glycan on a Fab-portion thereof. The disclosure further provides a method of monitoring an individual at risk of developing arthritis, Sjögren syndrome or AAV, the method comprising monitoring the presence and/or the onset of an autoantibody associated with the disease such as an AMPA, preferably an AAPA, ACPA and/or anti-CarP antibody in periodic antibody-containing samples of the individual. The method further comprises determining whether detected antibodies comprise an N-linked glycosylation at one or more positions in a Fab-portion of the antibody. Methods of the disclosure are particularly suited in screening a population of individuals for the conversion from a pre-disease "at-risk phase" into disease phase, such as RA. To this end, the sample that is tested in a method of the disclosure is preferably a sample from an individual that has been tested previously for RA. The antibodies are preferably AAPA, ACPA and/or anti-CarP antibodies.

Upon detection of AMPA, preferably an AAPA, ACPA and/or anti-CarP antibody, with an N-linked glycan on a Fab-portion of an antibody, the individual can be treated for arthritis, preferably rheumatoid arthritis, preferably with an arthritis medicament, preferably a rheumatoid arthritis medicament. As mentioned herein above, early treatment is beneficial to the patients. Also pre-symptomatic treatment is beneficial to individuals at risk of developing RA. Treatments are expensive and typically not completely without side effects, or the potential thereof. It is preferred to start pre-symptomatic treatment as soon as possible, i.e., when symptoms of RA are expected but at least when symptoms are imminent.

A person can always attract a disease. A person is said to be at risk using a method as described herein if that person has an increased risk over the normal population. For instance, a person that does not have RA but that does have an AMPA has an increased risk of developing RA. When such an individual is tested with a method as described herein and found to have an AMPA with an N-linked glycan on a Fab-portion thereof, that person has an increased risk of developing RA when compared to the population of AMPA-positive RA-negative individuals as a whole. A person has an AMPA with an N-linked glycan on a Fab-portion thereof if more than 10% of the AMPA antibodies in an antibody-containing sample of the individual has an N-linked glycan on a Fab-portion thereof, preferably more than 20%, preferably more than 30%, preferably more than 50%, preferably more than 55%. The same holds for an individual at risk of developing Sjogren syndrome or AAV. For instance, a person that does not have Sjogren syndrome or AAV but that does have an autoantibody associated with the disease has an increased risk of developing Sjogren syndrome or AAV. When such an individual is tested with a method as described herein and found to have the autoantibody with an N-linked glycan on a Fab-portion thereof, that person has an increased risk of developing Sjogren syndrome or AAV when compared to the population of autoantibody-positive Sjogren syndrome or AAV-negative individuals as a whole. A person has an autoantibody with an N-linked glycan on a Fab-portion thereof if more than 10% of the autoantibodies in an antibody-containing sample of the individual has an N-linked glycan on a Fab-portion thereof, preferably more than 20%, preferably more than 30%, preferably more than 50%, preferably more than 55%.

The disclosure thus further provides an arthritis medicament for use in a method of treatment of an individual comprising determining the presence or absence of an AMPA, preferably an AAPA, ACPA and/or anti-CarP antibody that comprises N-linked glycosylation at one or more positions in a Fab-portion of the antibody in an antibody-containing sample of the individual, and treating the individual when the antibody, preferably AAPA, ACPA or anti-CarP antibody comprising N-linked glycosylation in a Fab-portion has been detected.

Also provided is a method of treating an individual for a rheumatoid arthritis symptom or the risk of development thereof, the method comprising:
- determining whether a sample contains an AMPA, preferably an AAPA, ACPA and/or anti-CarP antibody that comprises N-linked glycosylation at one or more positions in a Fab-portion thereof;
- wherein the sample is an antibody-containing sample of the individual and the individual did not have rheumatoid arthritis at the time of sampling; and
- treating the individual with a rheumatoid arthritis medicament prior to or at the onset of the individual presenting with a rheumatoid arthritis symptom.

RA is a disease for which many different medicaments are available. A preferred medicament is a Disease Modifying Anti-Rheumatic Drug (DMARD). DMARD is a category of otherwise unrelated drugs defined by their use in rheumatoid arthritis to slow down disease progression. The term is often classified as synthetic DMARDs (sDMARDs, conventional or targeted) or biological DMARDs and used in contrast to non-steroidal anti-inflammatory drugs (which refers to agents that treat the inflammation but not the underlying cause) and steroids (which blunt the immune response but are insufficient to slow down the progression of the disease). In one embodiment, the rheumatoid arthritis medicament as referred to in the present disclosure is a non-steroidal anti-inflammatory drug or a steroid. In a preferred embodiment, the rheumatoid arthritis medicament is a sDMARD. Methotrexate is a preferred sDMARD. Other preferred DMARDs are abatacept; adalimumab; tocilizumab; azathioprine; chloroquine and hydroxychloroquine; etanercept golimumab; infliximab; leflunomide; methotrexate; rituximab and sulfasalazine. In addition, small molecule inhibitors such as tofacitinib represent a novel class of kinase inhibitors that are available in some countries. In a preferred embodiment, the DMARD is a monoclonal antibody that can bind tumor necrosis factor alpha (TNF-α). The rheumatoid arthritis medicament may also be a combination of two or more medicaments wherein one or more of the combination is a DMARD.

The tested individual is preferably provided with the rheumatoid arthritis medicament prior to or at the onset of the individual presenting with a rheumatoid arthritis symptom.

A medicament for the treatment of AAV or Primary Sjögren syndrome is preferably one or more of hydroxychloroquine, methotrexate, azathioprine, leflunomide, a glucocorticoid, rituximab, cyclophosphamide or mycophenolate.

The antigen-binding (Fab) portion comprises a region on an antibody that binds to antigens, the so-called variable domain. It preferably further comprises a constant domain that is associated with the variable domain in an antibody (together often referred to as a Fab-fragment). The Fab-portion is composed of a part of the heavy chain and a part of the light chain of the antibody. Fc and Fab fragments can be generated in the laboratory. The enzyme papain can be used to cleave an immunoglobulin monomer into two Fab fragments and an Fc fragment. The enzyme pepsin cleaves below the hinge region, so a F(ab')2 fragment and a pFc' fragment is formed. Recently, another enzyme for generation of F(ab')2 has been commercially available. The enzyme IdeS (immunoglobulin degrading enzyme from *Streptococcus pyogenes*, trade name FABRICATOR®) cleaves IgG in a sequence-specific manner at neutral pH.

Many of the methods can be performed with a Fab-portion or a Fab-fragment in part or all of the method, instead of a complete antibody. Such methods are, therefore, also provided in the present disclosure. This is typically clear to the skilled person.

Antibodies are purified when they are separated from other antibodies in the sample. The purified antibodies are typically separated from other antibodies on the basis of one or more characteristics. As a result, purified antibodies share the one or more characteristics used for the separation. The purified antibodies do not have to contain only one type of antibody. In the case of AMPA antibodies, it is perfectly possible that the purified antibodies all bind CCP2 (for instance) but nonetheless have different variable domains. Similarly, antibodies that are purified on the basis of binding to a molecule that binds an N-linked glycan on a fab-portion of the antibody can have different fab-portion linked glycans, as long as all thus purified antibodies bind to the molecule. A method is a method of purifying an antibody if it separates antibodies of a sample into fractions wherein at least one fraction has a percentage of purified antibody relative to all antibody in the fraction that is higher than the percentage in the sample prior to purification. In other words, the purified antibodies do not have to be essentially pure. Typically, however, it is preferred that a purified sample comprises at least 70%, more preferably at least 80%, preferably at least 90% and more preferably at least 95% of the purified type relative to all antibodies in the sample.

Determining the risk of an individual developing RA in a given time period is done by determining that the individual has an AMPA, preferably an AAPA, ACPA and/or anti-CarP antibody that comprises N-linked glycosylation at one or more positions in a Fab-portion thereof. The identification of such antibodies indicates the increased risk of the patient to develop RA in the indicated time period. The level at which such antibodies are detected is a measure for the actual time until development of RA symptoms. A high level indicates that the onset of disease is expected. Levels are preferably determined relative to the total amount of antibodies in the sample. Preferably they are determined relative to total AAPA, ACPA and/or anti-CarP in the sample.

The disclosure also provides a method of purifying antibodies for the measurement of antibodies comprising N-linked glycan on a Fab-portion thereof comprising:
  providing an antibody sample;
  contacting the sample with a solid surface that comprises a peptide or protein that comprises a modified protein epitope;
  removing unbound antibody and eluting bound antibody from the solid surface;
  incubating eluted antibody with a solid surface comprising a molecule that can bind an N-linked glycan on a Fab-portion of an antibody;
  removing unbound molecules; and
  determining whether an antibody has bound to the solid surface,
  wherein a bound antibody indicates the presence of an N-linked glycan on a Fab-portion of an antibody in the sample.

It is not necessary to purify complete antibodies. Antibody in the sample can be fragmented into Fab-portion and Fc fragments, for instance, and subsequently these fab-portion fragments are purified.

The disclosure also provides a method of purifying antibodies for the measurement of antibodies that have an N-linked glycan on a Fab-portion comprising:
  providing an antibody sample;
  contacting the sample with a solid surface that comprises a peptide or protein that comprises a modified protein epitope;
  removing unbound antibody;
  incubating the solid surface with a molecule that can bind an N-linked glycan on a Fab-portion of an antibody;
  removing unbound molecules; and
  determining whether a molecule has bound to the solid surface,
  wherein a bound molecule indicates the presence of an N-linked glycan on a Fab-portion of an antibody in the sample.

Further provided is a method of purifying antibodies for the measurement of antibodies that have an N-linked glycan on a Fab-portion comprising:
  providing an antibody sample;
  contacting the sample with a solid surface that comprises a peptide or protein that comprises a modified protein epitope;
  removing unbound antibody;
  incubating bound antibody with an enzyme that separates glycan from the antibody;
  collecting glycans; and
  determining whether the collected glycans comprise a Fab-portion-specific glycan;
  wherein the sample is an antibody sample of an individual at risk of developing RA, Sjögren syndrome or AAV.

Also provided is a method of purifying antibodies with N-linked glycosylation on a Fab-portion of the antibody, the method comprising:
  providing an antibody sample;
  incubating the sample with a solid surface that comprises a molecule that can bind an N-linked glycan on a Fab-portion of an antibody;
  washing the solid surface and collecting bound antibody;
  incubating collected antibody with a peptide or protein that comprises a modified protein epitope; removing unbound antibody; and
  determining whether the peptide or protein had bound antibody.

In certain embodiments, the sample comprises purified antibodies. In such cases, the antibodies were typically separated from other proteins of the sample by means of a binding agent that binds antibodies. Suitable agents are protein A or protein G.

Also provided is a method comprising:
  providing an antibody sample;
  contacting the sample with a solid surface that comprises a peptide or protein that comprises a modified protein epitope;
  removing unbound antibody;
  incubating the solid surface with a molecule that can bind an N-linked glycan on a Fab-portion of an antibody;
  removing unbound molecules; and
  determining whether a molecule has bound to the solid surface.

The sample is preferably an antibody sample of an individual at risk of developing RA, Sjögren syndrome or AAV. Preferably, the sample is an antibody sample of an individual of which an earlier antibody sample was tested positive for an autoantibody. Preferably, 10% or less of the autoantibody of the earlier antibody sample comprises an N-linked glycan on a Fab-portion thereof. The autoantibody is preferably an AMPA. In certain embodiments, the antibodies are cleaved to produce Fab and Fc fragments.

Antibody can be eluted from a solid surface by various means. Typically, this is achieved by changing the pH and/or the salt concentration of the surrounding fluid. The antibody is generally absorbed, bound to, an absorbent on a solid phase or solid surface. Elution is the process of removing analytes from the adsorbent by running a solvent, called an "eluent," past the adsorbent/antibody complex. As the solvent molecules "elute," or travel down through the column, they can either pass by the adsorbent/analyte complex or they can displace the analyte by binding to the adsorbent in its place. After the solvent molecules displace the analyte, the analyte can be carried out of the column for analysis.

Unbound antibody is typically removed by washing the solid phase with a buffer. Suitable buffers are buffers used to load to the antibody on the solid surface. Phosphate-buffered saline is a suitable buffer.

Periodic antibody-containing samples of an individual are samples that are taken at different time points in the life the individual. The interval between the time points can vary. The time between respective samples can be a month, two months, 6 months, a year, or even more. The time periods between samples can be longer when the autoantibody is negative for an N-linked glycan on a Fab-portion thereof. Time periods between samples of a series of periodic samples can vary and can be very short (days) to very long, more than a couple of years of periodic samples of one individual.

The moment of sampling is the day on which a sample of an individual has been collected. The taking of a sample can be part of the claim but is typically not part of the claim. The sample provided in the methods referred to in the claims is typically collected by an authorized person and subsequently handed over to provide it for a method as described herein.

For the purpose of clarity and a concise description, features are described herein as part of the same or separate embodiments, however, it will be appreciated that the scope of the disclosure may include embodiments having combinations of all or some of the features described.

The disclosure further provides a method for determining whether an antibody comprises an N-linked glycan, the method comprising purifying AMPA from an antibody-containing sample and detecting whether the AMPA comprises an H5N4S2; H5N5F1S1, H5N4F1S2; H5N5S2; H5N5F1S2 and/or H6N5F1S2 glycan of FIG. 1A. In a preferred embodiment, the method further comprises determining whether the glycan is present on a FAB-portion of the antibody when one or more of the glycans have been detected.

In FIG. 1A, the nomenclature of glycans found on ACPA-IgG and IgG is illustrated. G2S2, G2FS1B, G2FS2, G2S2B, G2FS2B are considered as Fab-glycans because these glycan structures are highly expressed by Fab fragments of ACPA-IgG and IgG, whereas these structures are low- or not expressed on Fc fragments.

EXAMPLES

Example 1

Material and Methods
Patient Samples

For experiments to compare ACPA glycosylation with total IgG glycosylation, plasma (n=6) and synovial fluid (n=3) samples from 9 ACPA-positive RA patients were collected at the outpatient clinic of the rheumatology department at LUMC. All RA patients fulfilled the American College of Rheumatology 1987 revised criteria for the classification of RA.

For the experiments to compare ACPA-Fab glycans of ACPA derived from ACPA-positive RA patients and their ACPA-positive healthy relatives, serum samples were collected from 53 ACPA-positive RA patients and their unaffected ACPA-positive first-degree relatives at rheumatology clinics in Canada. The prevalence of RA is considerably higher in these communities than in the general Caucasian population, and ACPA are present at increased frequency in healthy relatives of patients.[1, 2] RA patients fulfilled the American College of Rheumatology 1987 revised criteria for the classification of RA.

Purification of Antibodies

ACPA-IgG and IgG of samples collected in Leiden were purified on fast protein liquid chromatography (ÄKTA, GE Healthcare) as previously described.[3] Briefly, samples were loaded on a biotinylated CCP2-arginine-HITRAP®-streptavidin column (GE Healthcare) followed by a biotinylated CCP2-citrulline-HITRAP®-streptavidin column connected in series. The flow through (FT) and ACPA-eluted fractions were further loaded on a HITRAP® protein G and subsequently on a HITRAP® protein A column (both from GE Healthcare). The purified fractions of ACPA-depleted IgG (control IgG) and of ACPA-IgG were concentrated and desalted by size exclusion chromatography.

ACPA-IgG was purified from Canadian samples using a micro-bead system. Briefly, 25 µl plasma or serum was loaded on neutravidin beads which was coupled to a biotinylated CC(cit)P peptide. The samples were incubated for 2 hours and ACPA was eluted with formic acid and neutralized to a Ph of 7.5. The ACPA-eluted fractions were further loaded on Prot G beads to end up with ACPA-IgG.

Structural Analysis

The structural analysis to compare ACPA with general IgG was performed on F(ab)$_2$ or Fc fragments of the isolated ACPA-IgG and IgG. F(ab)$_2$ and Fc fragments were generated by antibody digestion with IdeS (FABRICATOR®; Genovis) and purified by IgG-Fc/CH1 CAPTURESELECT® affinity beads (Thermo Fisher). N-glycans from F(ab)$_2$ and Fc fragments of (ACPA)-IgG were released in solution using PNGase F. Glycans were labelled with 2-aminobenzoic acid (2-AA), purified by hydrophilic interaction chromatography solid-phase extraction (HILIC-SPE) and characterized by matrix-assisted laser desorption/ionization time of flight mass spectrometry (MALDI-TOF-MS) and Ultra-high performance liquid chromatography (UHPLC).

For the experiments to compare ACPA-Fab glycans of ACPA derived from ACPA-positive RA patients and their healthy relatives, structural analysis was performed on the isolated ACPA-IgG. N-glycans of the ACPA-IgG were released in solution using PNGase. In addition, the glycans were labelled with 2-aminobenzoic acid (2-AA), purified by hydrophilic interaction chromatography solid-phase extraction (HILIC-SPE) and characterized by Ultra-high performance liquid chromatography (UHPLC).

Data and Statistical Analysis

UHPLC data were analyzed with CHROMOLEON® 7. The software calculates the area under the curve of the chromatograms. Glycan peaks and glycosylation-derived traits were defined as previously described.[4] The percentage of galactosylation, sialylation, fucosylation and the frequency of bisecting N-acetylglucosamine residues of IgG were calculated. In addition, the percentage Fab glycosylation is calculated with the following formula: (sum of GP19 till GP24)/(sum of GP1 till GP14)*100%. The statistical analysis was performed using GraphPad Prism 6. A non-parametric paired Wilcoxon test was applied with a significance limit at $p<0.05$.

Results

Recently, it was discovered that ACPA-IgG obtained from RA-patients exhibit a 10-20 kDa higher molecular weight compared with non-autoreactive IgG. This feature also distinguished ACPA-IgG from antibodies against recall antigens or other disease-specific autoantibodies. Structural analysis showed that the presence of N-linked glycans in the (hyper) variable domains (F(ab) domains) of ACPA is responsible for this observation. Elucidation of the precise sites where the N-linked glycans are located revealed that the N-linked consensus sequence required for N-linked glycosylation of proteins was not germline encoded but had been introduced upon somatic hypermutation.[5] Structural analysis of the N-linked Fab-glycans present on ACPA showed that the composition of Fab-linked glycans differed from Fc-linked sugars and, more importantly, that these are highly sialylated (FIG. 1B). Moreover, based on quantification, it is estimated that over 90% of ACPA molecules present in serum harbor F(ab)-glycans, a percentage that is even higher on ACPA in synovial fluid.

Figure 2A:
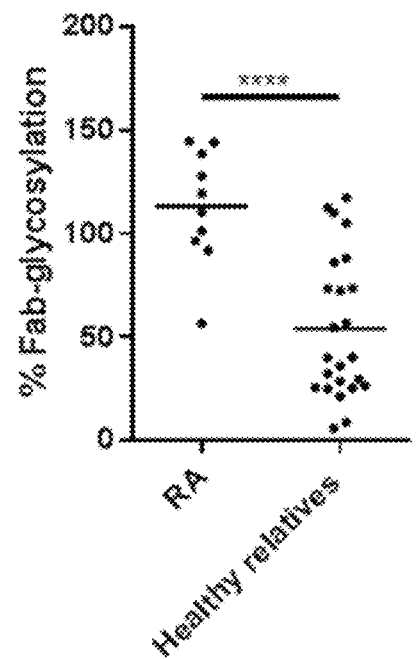
FIG. 2A: Serum samples from ACPA+RA patients and their healthy ACPA+ first degree relatives (Healthy relatives) were analyzed for the presence of F(ab) glycans on ACPA. The frequency of F(ab)-glycans on ACPA is remarkably lower on ACPA derived from healthy donors as compared to ACPA from RA patients.
Figure 2B:
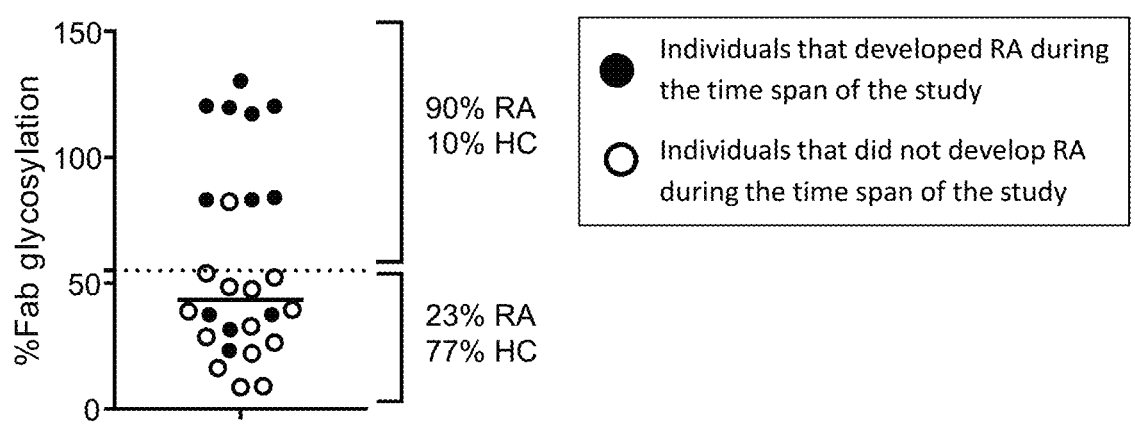
FIG. 2B: Predictive value of the percentage of the ACPA-IgG Fab glycosylation before RA diagnosis: 26 ACPA-positive healthy first-degree relatives of RA patients were followed over time. Every circle represents the median of the ACPA Fab glycosylation of one individual that is followed until disease onset of rheumatoid arthritis (RA; black circles) or is followed over a similar time span without RA development (HC; healthy control; white circle). Of these 26 followed individuals, 46% developed RA over time. The percentage of Fab glycosylation of general IgG is 15-25%. IgG-Fab glycosylation >55% is considered "abnormal." Healthy individuals that developed RA at the end of the study period demonstrated higher percentages of Fab-glycosylation before RA diagnosis compared to the individuals that did not develop RA.

Remarkably, preliminary data show that the frequency of hyperglycosylated ACPA is considerably lower on ACPA derived from healthy ACPA-positive relatives (FIGS. 2A and 2B). This is intriguing as it indicates that ACPA present in healthy individuals have not yet introduced the N-linked glycosylation sites in the ACPA variable regions required for glycosylation.

Although the methodology described above can be converted into a high-throughput assay, the current assay to detect ACPA F(ab)-hyperglycosylation is time-consuming and requires high-end mass spectrometry and expertise. Therefore, a more accessible method that can be used in day-to-day routine would be preferred. It has been demonstrated that the binding of antibodies to the lectin SNA (Sambuccus Nigra Agglutinin) is primarily mediated by F(ab) glycosylation and that two sialic residues are required for binding to SNA. SNA will only bind to the Fc part under reducing conditions (which opens up the interface between CH2 domains).[6-8] As most ACPA F(ab)-glycans contain two sialic acid residues, it is highly likely that SNA-binding of serum antibodies from RA-patients will enrich for ACPA.

Therefore, an SNA-binding-based approach to detect ACPA F(ab)-glycans represents a promising strategy to visualize the presence of these glycans without the need of high-end mass spectrometry. Therefore, two approaches were embarked upon to establish a high-throughput method based on SNA-detection. These approaches aim to develop a standardized protocol allowing the detection of ACPA F(ab)-glycans in a high-throughput manner.

In the first approach (FIGS. 3A-3C), ACPA was first captured using CCP-coated microbeads (left panel). After elution of ACPA from these beads, the presence of F(ab) glycans was visualized using labelled SNA (right panel). As the preliminary data indicate that the F(ab) glycans do not directly interact with antigen and hence might be accessible for SNA, it is conceivable that elution of ACPA from the beads is not necessary and that SNA can directly bind to ACPA F(ab)-glycans. Therefore, this possibility will also be tested.

In the second approach (FIG. 4A.1, left panel), a reverse strategy will be taken by first immobilizing F(ab)-glycosylated IgG (ACPA) on SNA, followed by detection of ACPA using a CCP-ELISA. The preliminary data indicate that this approach is feasible and can be used in a high-throughput manner (FIG. 4A.1, right panel). At present, this approach includes pre-isolation of IgG by protein A in order to prevent "overloading" of SNA by other molecules present in serum that carry sialic acid molecules. The preliminary data suggest that this might not be required, a possibility that will also be investigated in this context.

Example 2

Material and Methods
Patient Samples

Plasma (n=6) and synovial fluid (n=3) samples from nine ACPA-positive RA patients were collected at the outpatient clinic of the rheumatology department at Leiden University Medical Center. All RA patients fulfilled the American College of Rheumatology 1987 revised criteria for the classification of RA and gave written informed consent.[9] Treatment included disease-modifying anti-rheumatic drugs, biological agents and glucocorticoids.

Chemicals, Solvents and Enzymes Used

TFA, SDS, disodium hydrogen phosphate dihydrate, HCl, Glycine, β-mercaptoethanol, acetic acid and NaCl were purchased from Merck (Darmstadt, Germany). Fifty percent sodium hydroxide and nonidet P-40 substitute, hyaluronidase from bovine testes type IV, EDTA, 2-aminobenzoic acid, 2-picoline borane complex, ammonium hydroxide, DMSO and formic acid were obtained from Sigma-Aldrich (St. Louis, USA). Tris was purchased from Roche (Indiana, USA) and the laemmli buffer was obtained from Bio-Rad (California USA). Peptide: N-glycosidase F (PNGase F) was bought from Roche Diagnostics (Mannheim, Germany), 2,5-dihydroxybenzoic acid from Bruker Daltonics (Bremen, Germany) and HPLC Supra-gradient ACN from Biosolve (Valkenswaard, Netherlands). MQ (MILLI-Q® deionized water; R>18.2 MΩ cm-1; Millipore Q-GARD® 2 system, Millipore, Amsterdam, The Netherlands) was used throughout. CAPTURESELECT® anti-IgG Fc affinity matrix and anti-CH1 affinity matrix were bought from Life Technologies (Leiden, The Netherlands). Empty spin column with closed screw cap, inserted plug and large 10-µm filter were provided from MoBiTec (Goettingen, Germany). The PBS was obtained from B. Braun (Meslungen Germany) and the IdeS enzyme (trade name FABRICATOR®) from Genovis (Lund, Sweden). The CCP2 arginine (control) and CCP2 citrulline peptides were kindly provided by Dr. J. W. Drijfhout, Department of IHB, Leiden University Medical Center (LUMC), The Netherlands.

Purification of ACPA-IgG and ACPA-Depleted IgG.

ACPA-IgG and IgG were purified on fast protein liquid chromatography (ÄKTA, GE Healthcare) as previously described.[5] Briefly, samples were loaded on a biotinylated CCP2-arginine-HITRAP®126 streptavidin column (GE Healthcare) followed by a biotinylated CCP2-citrulline-HITRAP®-streptavidin column connected in series. The flow through (FT) and ACPA-eluted fractions were further loaded on a HITRAP® protein G and subsequently on a HITRAP® protein A column (both from GE Healthcare). The purified IgG and ACPA-IgG of the isotypes 1, 2 and 4 were then concentrated and desalted by size exclusion chromatography (ZEBA™ Spin Desalting Column, 7K MWCO, Pierce Thermo Scientific) according to the manufacturer's instructions.

Generation and Purification of Fc and F(Ab')2 Fragments

ACPA-IgG and ACPA-depleted IgG were specifically cleaved into Fc and F(ab')2 portions by using the recombinant streptococcal IdeS enzyme. The supplier's protocol was adjusted to simplify the procedure as previously described. [5] Briefly, for each sample, 30 µg of (ACPA)-IgG antibodies were dried under centrifugal evaporator and digested by adding 200 µL digestion buffer (50 mM sodium phosphate, 150 mM NaCl, 5 mM EDTA) containing 30 U of IdeS followed by incubation at 37° C. for overnight. The Fc portion was then separated from the F(ab')2 by affinity chromatography on anti-IgG Fc affinity matrix (bead slurry) loaded on a 10-µM filter spin column. The Fc fragments were eluted from beads with 100 mM formic acid and neutralized with 2 M Tris. In order to capture the F(ab')2 domain, the FT fraction resulting from the Fc purification was purified on anti-IgG-CH1 affinity matrix using a similar protocol as for the anti-IgG Fc affinity matrix. Elution fractions were neutralized with 2 M TRIS and desalted by size exclusion chromatography (ZEBA™ Spin Desalting Columns, 7 kDa MWCO, Pierce Thermo Scientific). Following purification, 6 µg of the purified Fc and F(ab')2 samples were analyzed for their purity by SDS-PAGE and quantified by bicinchoninic acid protein assay reagent (Pierce Thermo Scientific). For glycan analysis, the samples were dried by vacuum centrifugation.

Structural Analysis

The structural analysis was performed on of either the total molecule, F(ab)2 or Fc fragments of the isolated ACPA-IgG and IgG from nine RA patients. In addition, sodium dodecyl sulphate polyacrylamide gel electrophoresis (SDS-PAGE) was performed of (ACPA)-IgG. N-glycans from total molecule, F(ab)2 and Fc fragment of (ACPA)-IgG were released in solution using PNGase F, whereas the heavy and light chain (HC/LC) glycans were obtained following in-gel digestion with PNGase F. Labelling of glycans was performed by mixing the samples (in 25 µL) with 12.5 µL of 2-aminobenzoic acid (2-AA; 48 mg/mL) in DMSO with 15% glacial acetic acid and 12.5 µL 2-picoline borane (107 mg/mL) in DMSO. The mixture was incubated for 2 hours at 65° C., cooled down to room temperature and diluted to 85% ACN prior to purification. The 2-AA-labelled glycans were purified by HILIC SPE using cotton tips as described previously with some modifications.[10] Briefly, for each sample, 500 µg of cotton were packed into a 200 µL pipette tip and conditioned by pipetting three times 150 µL MQ, followed by 150 µL 85% ACN 0.1% TFA and two times 150 µL 85% ACN. The sample (in 85% ACN) was loaded by pipetting 25 times into the reaction mixture. The tips were washed three times with 150 µL 85% ACN 0.1% TFA and two times with 150 µL 85% ACN. The 2-AA-labelled glycans were finally eluted from the cotton with 30 µL MQ and identified by MALDI-TOF-MS and UHPLC. For MALDI-TOF-MS analysis, 2 µL of glycan sample purified by cotton HILIC SPE were mixed on spot with 1 µL of 2,5-dihydroxybenzoic acid matrix (20 mg/mL in 50% ACN, 50% water) on a Bruker ANCHORCHIP™ plate (800 µm anchor; Bruker Daltonics, Bremen, Germany) and allowed to dry at ambient temperature. Measurement was performed in linear negative mode on an UltrafleXtreme MALDI-TOF-MS (Bruker Daltonics) using FlexControl 3.4 software (Bruker Daltonics). A peptide calibration standard (Bruker Daltonics) was used for external calibration. For each spectrum, a mass window of m/z 1000 to 4000 was used and a minimum of 5000 laser shots were accumulated. Regarding UHPLC analysis, 5 µL of purified 2-AA-labelled N-glycan solution were separated and analyzed by HILIC-UHPLC on a DIONEX™ ULTIMATE™ 3000 (Thermo Fisher Scientific) equipped with a 1.7 µm 2.1×100 mm Acquity UHPLC BEH Glycan column (Waters) and with a fluorescent detector. Separation was performed at 60° C. with a flow rate of 0.6 mL/minute. Two solutions were used for gradient generation, ACN as solution A, and 100 mM ammonium formate pH 4.4 (prepared as formic acid buffered to pH 4.4 by ammonium hydroxide) as solution B. The column was equilibrated by 85% solution A for 0.5 minute. The samples were then loaded in 75% A, and excess of fluorescent reagent was eluted from the column by washing with 85% A 47 for 10 minutes. The separation gradient started at 75% A and decreased linearly to 63% A in 30 minutes. The column was then flushed at a flow rate of 0.4 mL/minute with 40% A for 4 minutes followed by 10 minutes of 85% A for re-equilibration. For fluorescent detection, 330 nm was used for excitation and the emission recorded at 420 nm. The resulting chromatograms were analyzed using CHROMOLEON® version 7.1.2.1713 (Thermo Fisher Scientific). Finally, to analyze the Fc-linked glycosylation of (ACPA)-IgG at the glycopeptide level, antibodies were digested with trypsin and analyzed by LC-MS as described.[11]

Data and Statistical Analysis

UHPLC data was analyzed with CHROMOLEON® 7; the program calculates the area under the curve of the UHPLC chromatograms. Glycan peaks and glycosylation-derived traits were defined as previously described.[4] The percentage of galactosylation (non-galactosylated G0, monogalactosylated G1 and di-galactosylated G2), sialylation (non-sialylated N, mono-sialylated S1 and disialylated S2), fucosylation (F) and the frequency of bisecting N-acetylglucosamine (GlcNAc, B) residues of IgG were calculated as follows: G0=GP1+GP2+GP4+GP5+GP6, G1-GP7+GP8+GP9+GP10+GP11+GP16, G2-GP12+GP13+GP14+GP15+GP17+GP18+GP19+GP21+GP22+GP23+GP24, N=GP1+GP2+GP4+GP5+GP6+GP7+GP8+GP9+GP10+GP11+GP12+GP13+GP14+GP15, S1=GP16+GP19, S2-GP21+GP24, F=GP1+GP4+GP6+GP8+GP9+GP10+GP11+GP14+GP15+GP16+GP18+GP19+GP23+GP24 and B-GP6+GP10+GP11+GP13+GP15+GP19+GP22+GP24. Analysis of the glycan traits of the LC-MS were previously described.[11] For the processing of LC-MS data, the total intensity of the first three isotopes of every observed analyte charge state was extracted within a window of ±0.06 Da around the theoretical mass and ±20 seconds around the manually extracted average retention time as described earlier.[12] Glycan identification by MALDI-TOF-MS were defined as previously described.[13] The statistical analysis was performed using GraphPad Prism 6. A non-parametric paired Wilcoxon test was applied with a significance limit at $p<0.05$.

Results

Quantification of the N-Glycans Expressed by IgG and ACPA-IgG.

Figure 9A:
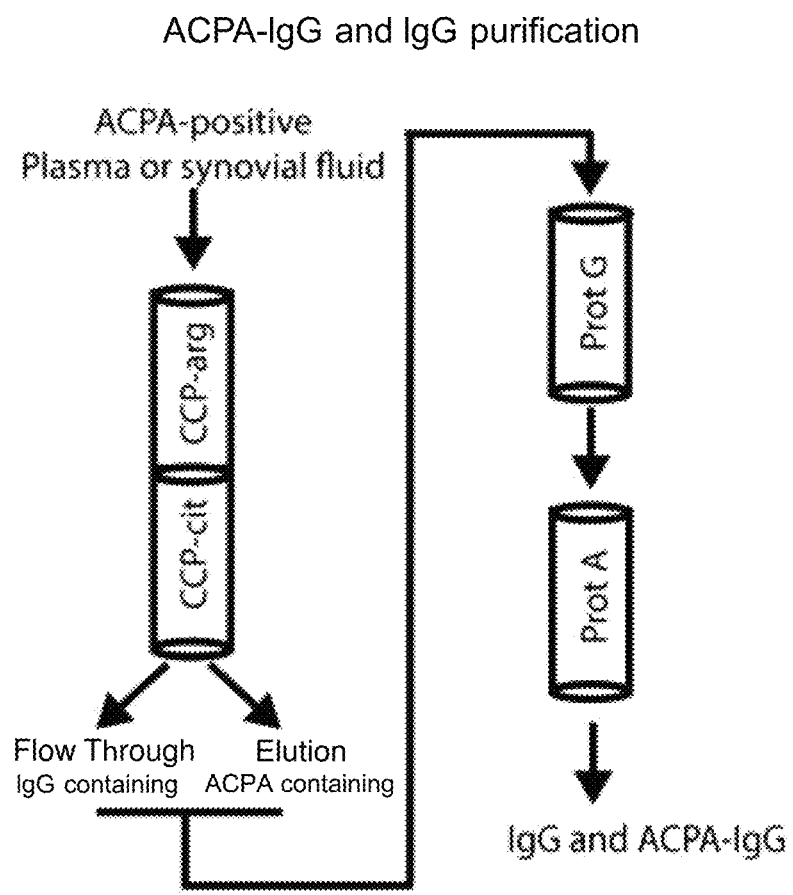
Figure 10A:
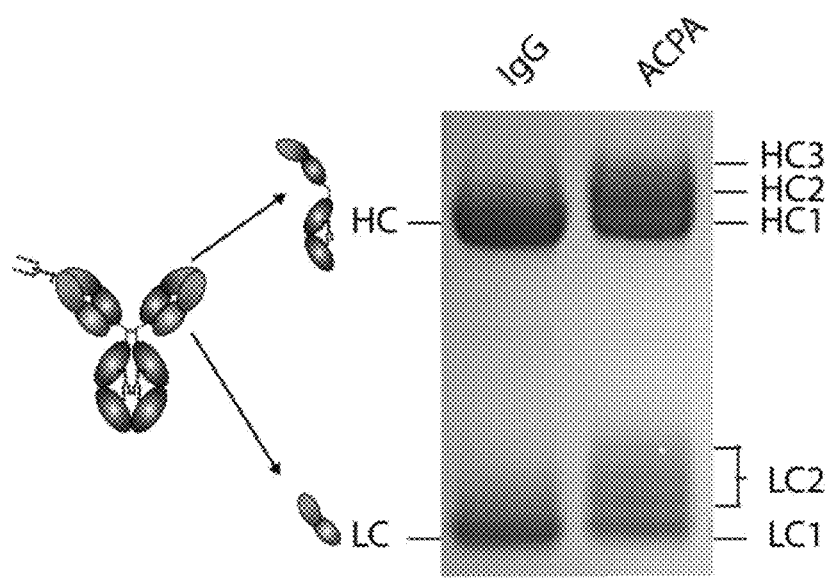
FIGS. 10A and 10B: The glycosylation of heavy chain (HC) and light chain (LC) derived from ACPA-IgG and IgG isolated from RA patients.
Figure 10B:
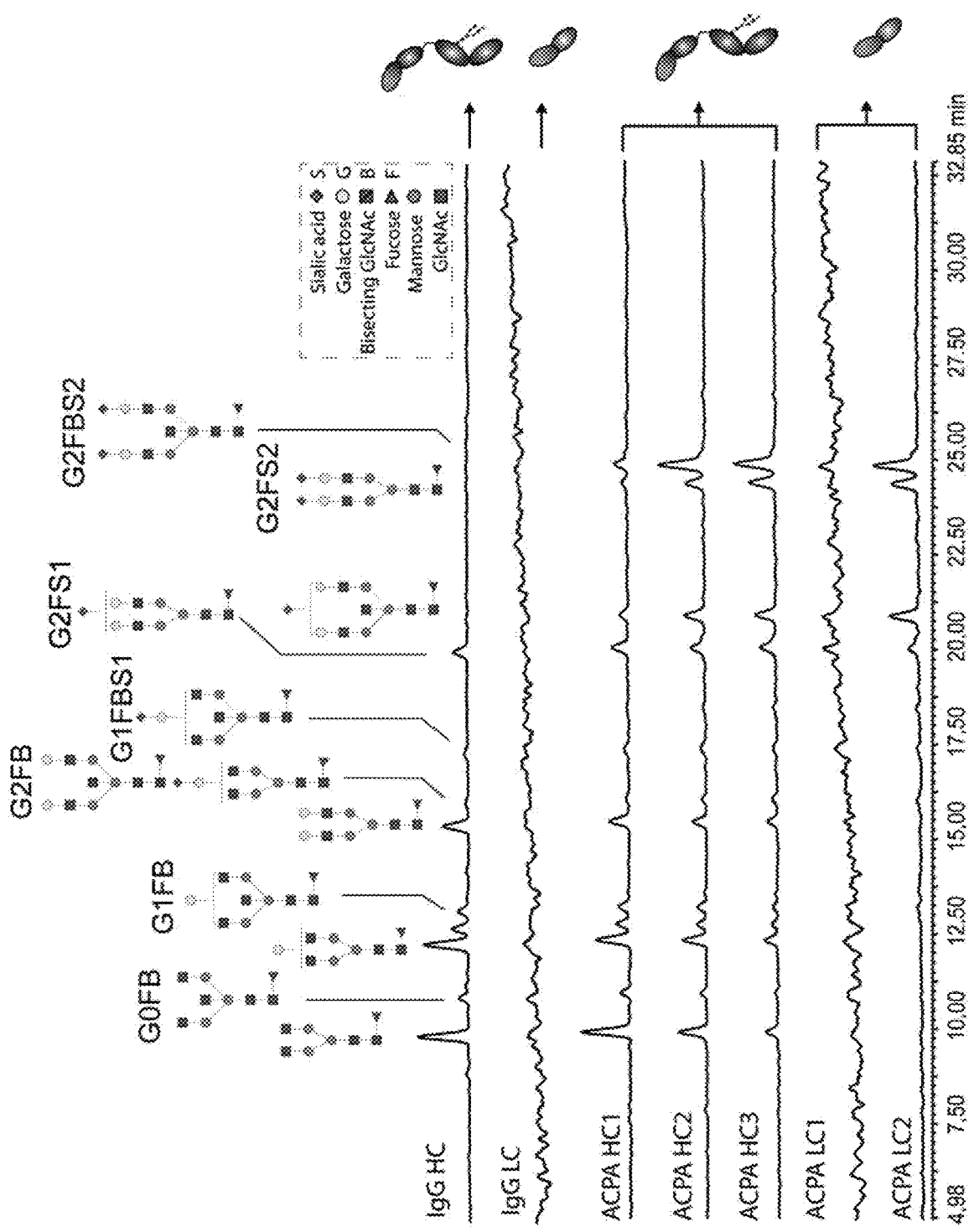

It was demonstrated that ACPA-IgG produced by RA patients are extensively N glycosylated in the variable region as compared to other IgG (auto) antibodies.[5] A comprehensive quantitative and qualitative analysis of the glycosylation of ACPA-IgG and its fragments was performed and compared it to that of non-citrulline-specific IgG (i.e., depleted of ACPA hereafter named control IgG). To this end, (ACPA)-IgG were purified by affinity chromatography and their glycans were analyzed by UHPLC, MALDI-TOF-MS and/or LC-MS according to the scheme presented in FIGS. 9A-9C. Following purification, the purity of (ACPA)-IgG was assessed by SDS-PAGE under reducing conditions (FIG. 10A). As expected, control IgG was characterized by two electrophoretic bands corresponding to the heavy and light chains (HC and LC), whereas ACPA-IgG showed several HC and LC bands with higher molecular weights as previously described. Released N-glycans from both the HC of IgG and the HCl of ACPA-IgG displayed a typical Fc-linked glycan profile in UHPLC,[21, 25] while no N-glycans were detected in the LC of IgG and the LC1 of ACPA-IgG (FIG. 10B). In contrast, N-glycans released from LC2 of ACPA-IgG showed a different profile, indicating the presence of diantennary glycoforms that were highly sialylated (FIG. 10B). Likewise, the glycosylation profiles derived from HC2 and HC3 of ACPA-IgG showed the presence of a mixture of Fc-glycans but also of additional glycans usually not present in the Fc-domain (FIG. 10B).

Fc-Linked and Fab-Linked Glycans of IgG (Auto) Antibodies Exhibit Typical Antibody Glycan Patterns.

Figure 11A:
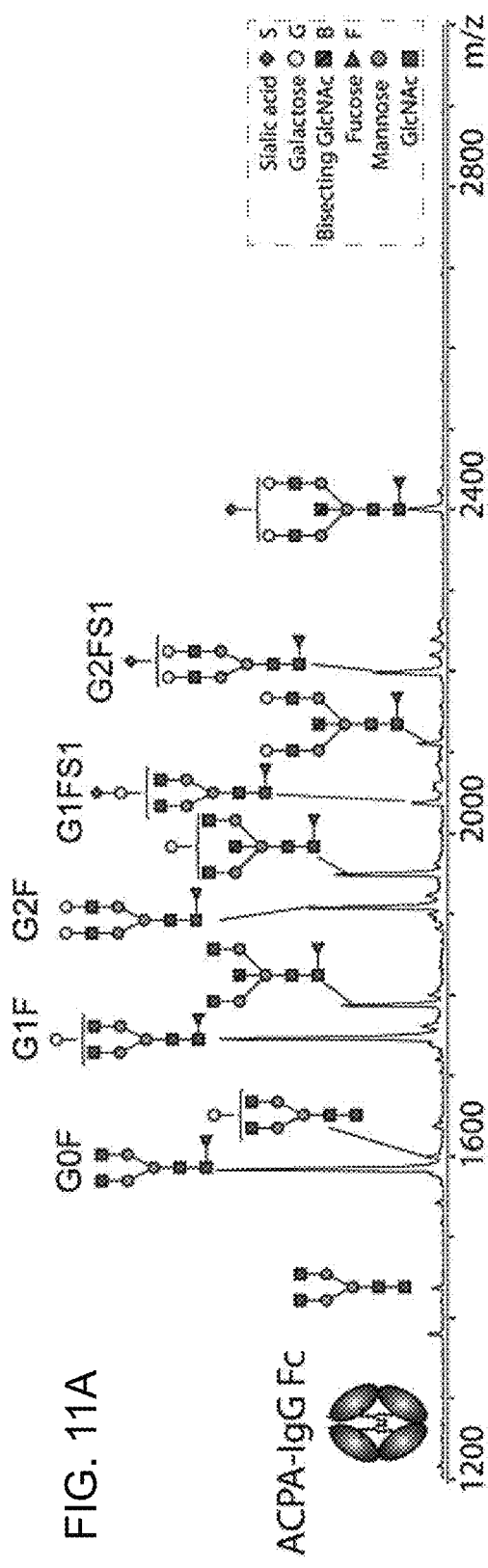
FIGS. 11A and 11B: ACPA-IgG is differentially glycosylated in the Fc compared to the Fab glycosylation. MALDI-TOF spectra of the (FIG. 11A) Fc and (FIG. 11B) F(ab')2 fragments of ACPA-IgG purified from a representative donor.
Figure 11B:
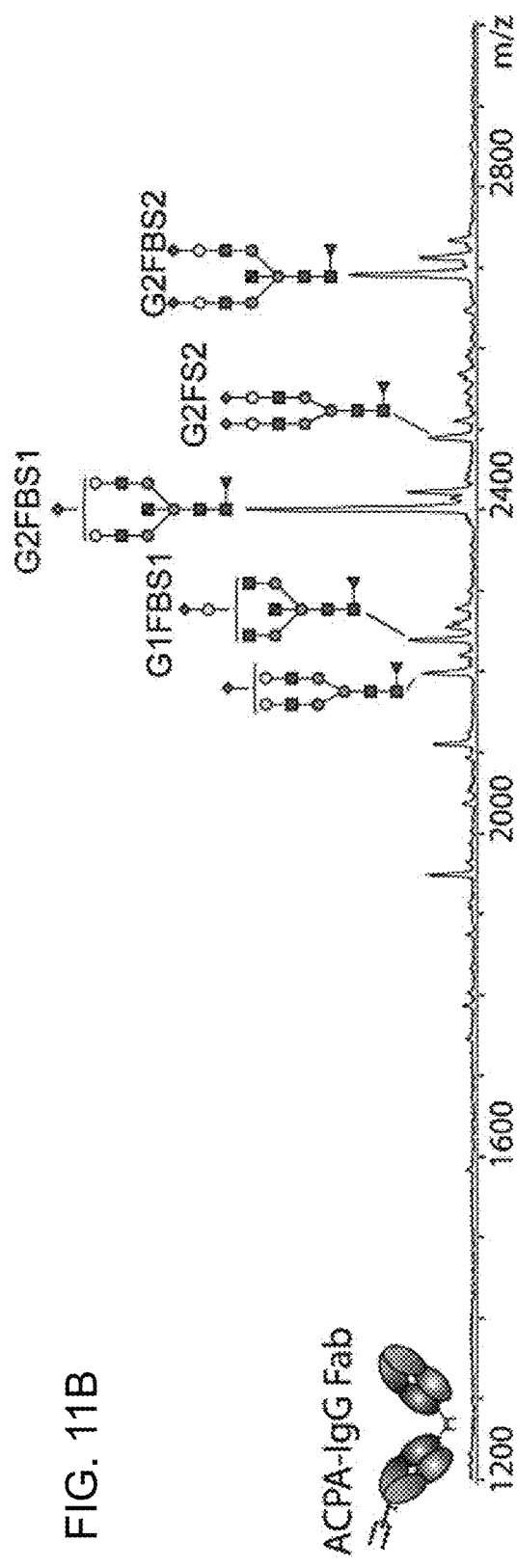

To determine if the glycan pattern detected in the additional HC band of ACPA-IgG, i.e., HC2 and HC3, truly reflects the glycosylation of the IgG variable region. The N glycosylation of (ACPA)-IgG and its fragments (Total/Fc/Fab) or glycopeptides (for Fc only) were investigated (FIGS. 9A-9C). The structure of N-glycans released from Fc and F(ab')2 fragments of ACPA-IgG and control IgG (from the same donor) were first analyzed and compared. The N glycosylation profile derived from (ACPA)-IgG Fc fragments exhibited typical Fc-linked N-glycan structures that consisted of diantennary, often core fucosylated complex type species with a variable number of antenna galactose (0 to 2) and sialic acid (0 to 1) residues (FIG. 11A). Part of the Fc-linked N-glycans also contained a bisecting GlcNAc. Of note, a relatively high proportion of non-galactosylated glycans (G0) was observed as previously described.[11] The N glycans released from (ACPA)-IgG F(ab')2 fragments consisted of highly galactosylated and sialylated diantennary glycoforms, that may carry bisecting GlcNAc and/or a core fucose (FIG. 11B). Together, the results demonstrate that the N-glycan species attached to the Fc and Fab fragments of IgG (auto) antibody differ with a striking presence of highly sialylated glycan species in the glycans linked to the Fab-domain of ACPA-IgG.

The Fab-Linked Glycosylation Pattern of ACPA-IgG Differs from the Pattern on "Conventional" IgG.

It has been shown that Fc-linked N-glycans of ACPA-IgG isolated from patients present a more pronounced reduction in the level of galactosylation and sialylation but an increased degree of core fucosylation than those of other IgG molecules.[11, 15] In agreement, the Fc-glycans of ACPA IgG purified in this study exhibit a lower level of sialylation (S 12% [IQR9-16%] for ACPA-IgG versus 16%

Figure 12A:
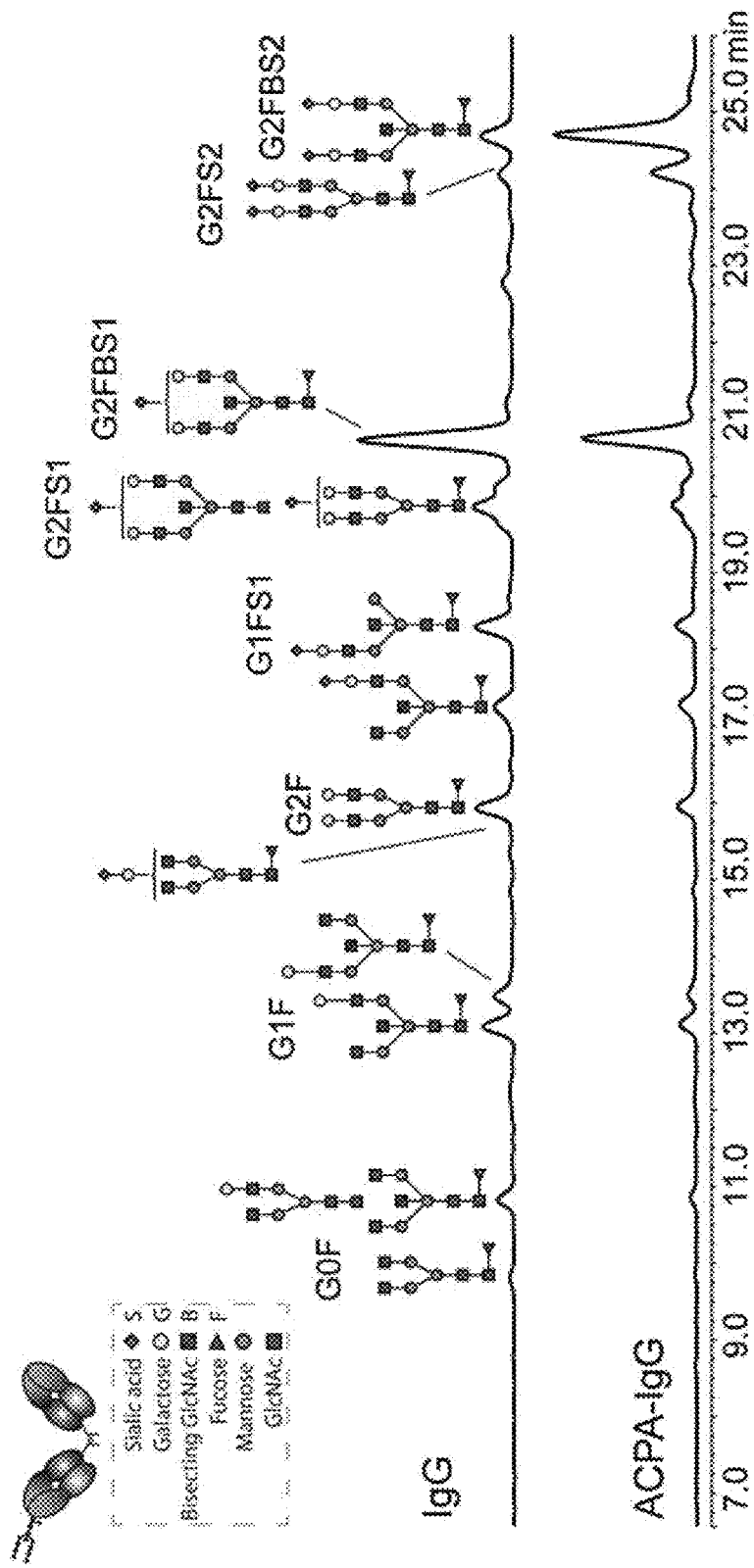
FIGS. 12A and 12B: The Fab-linked glycosylation patterns differ between ACPA-IgG and non-citrulline-specific IgG isolated from RA patients.
Figure 12B:
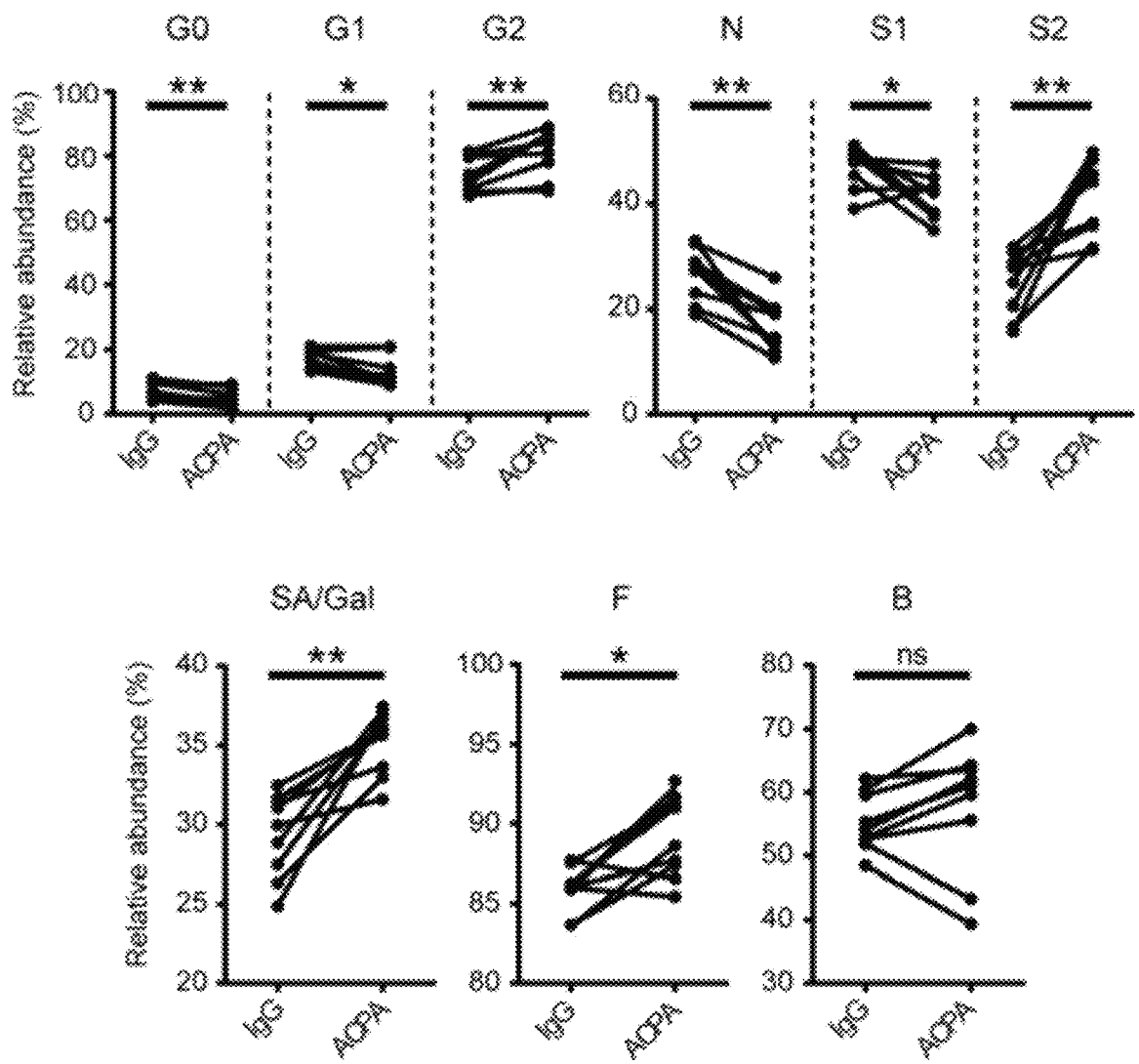

[IQR13-17.5%] for control IgG) as well as a higher frequency of core fucosylation in comparison with that of control IgG (F 99.3% [IQR98.7-99.7%] for ACPA-IgG versus 91.8% [IQR90.3-99.7%]) IgG. In addition, however, the data revealed important differences between the Fab-linked N-glycan profile of ACPA-IgG and that of control IgG (FIGS. 12A and 12B). Especially, ACPA-IgG Fab N-glycans displayed a high frequency of di-galactosylated species (G2; 73% [IQR69.5-80%] for IgG versus 84% [IQR74-87%] for ACPA-IgG) and di-sialylated 259 species (S2; 27% [IQR19-30%] for IgG versus 44% [IQR34-48.5%] for ACPA-IgG), as also exemplified by an increase in the ratio of sialic acid per galactose (SA/Gal; 36% [IQR33-37%] versus 30% [IQR27-31.5%] for ACPA-IgG and IgG). In addition, higher levels of core fucose and bisecting GlcNAc residues in 7 out of 9 samples were found. In general, stronger glycan differences were observed between the glycan structures derived from the Fab domain of ACPA-IgG and control IgG than between the glycans from the Fc portions.

ACPA-IgG Exhibit a Higher Level of Fab Glycosylation.

Figure 13B:
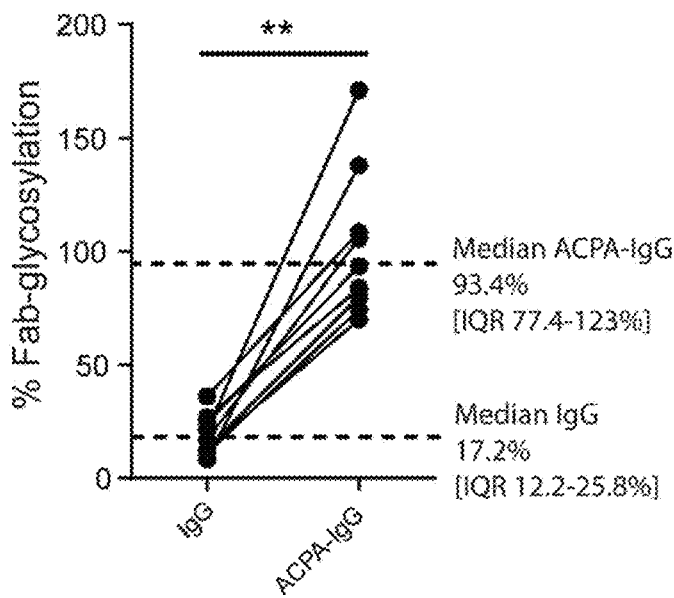

The amount of Fab glycosylation present on ACPA-IgG and IgG depleted from ACPA was quantified. To estimate the level of Fab glycosylation, glycans were released from ACPA-IgG and ACPA depleted IgG, characterized by MALDI-TOF-MS, and their relative abundance was measured by UHPLC. Whereas the glycan profile of total IgG was dominated by Fc-linked N-glycans (G0F, G1F and G2F), the total glycan profile of ACPA-IgG exhibited a large quantity of Fab-linked N-glycan (G2FBS1, G2FS2 and G2FBS2) (FIG. 13A). Importantly, the identification of a number of these glycoforms specific for either the Fc- or the F(ab')2-fragment, and the quantification of these glycoforms released from the entire antibody molecule, enabled determination of the overall frequency of Fab glycans on either ACPA-IgG or ACPA-depleted IgG (FIG. 13B). All ACPA-IgG samples (n=9) exhibited an increased frequency of Fab glycosylation compared to control IgG. The median Fab-glycosylation level of IgG depleted of ACPA was estimated at 17% [IQR12%-26%], with large differences between donors. In contrast, the median Fab glycosylation of ACPA-IgG reached 93% [IQR77-123%]. Together, these data indicate that the median Fab glycosylation of ACPA-IgG is five times higher than that of control IgG.

(ACPA)-IgG Derived from Plasma and Synovial Fluid Display Different Fab Glycosylation Profiles.

Figure 13C:
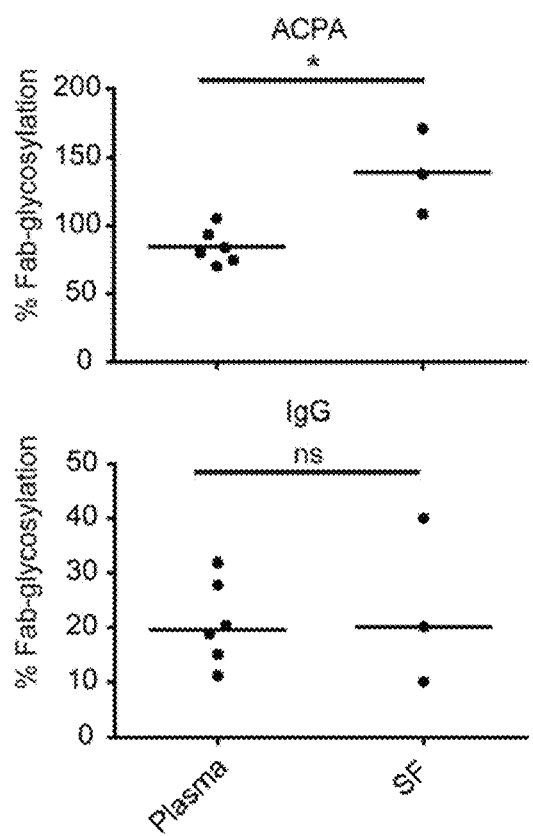

It was demonstrated that ACPA-IgG derived from the synovial fluid display a more proinflammatory Fc glycosylation profile than ACPA-IgG purified from serum.[16] Given this observation, it was hypothesized that differences may also occur in the Fab-linked glycan structures and/or Fab-glycosylation levels of ACPA-IgG and control IgG. As compared to the plasma ACPA-IgG (n=6) Fab-linked glycans, the composition of SF derived ACPA-IgG (n=3) Fab glycans exhibited a trend toward lower levels of galactosylation, sialylation and bisecting GlcNAc. A similar trend was observed for the glycan profile of SF control IgG compared to plasma IgG. Next, the level of Fab-glycosylation of plasma (ACPA)-IgG and their counterparts from the SF was quantified. As shown in FIG. 13C, a significantly higher level of Fab glycosylation was found in ACPA IgG from the SF as compared to plasma ACPA-IgG (138% vs. 80%). Of note, such a difference was not observed for control IgG (20% vs. 20%). Together, these observations indicate in quantitative terms that the level of Fab-glycosylation is even more pronounced on ACPA-IgG from SF as compared to ACPA-IgG from blood.

Example 3

Material and Methods

Determination of N-Linked Glycosylation in the Fab-Portion of IgG for ACPA or antiCarP IgG.

Biotinylated CCP2 or arginine control peptides are conjugated to different fluorochrome-labelled streptavidin tetramers. By fluorescence-activated cell sorting (FACS), tetramer-positive B-cells are sorted. With two different methods, B-cell receptor (BCR) sequences are determined. The general method for isolating ACPA-specific B-cells is described in Kerkman et al., Jun. 2, 2015; *Ann. Rheum. Dis.*, 0:1-7; doi: 10.1136/annrheumdis-2014-207182.

For the first method, tetramer-positive single B-cells are cultured in vitro for 10-12 days in IMDM medium with a cytokine cocktail on a layer of CD40L-expressing L-cells. Supernatants of these cultures are analyzed for antibodies with CCP2 reactivity by ELISA. Besides, the CCP2-positive supernatants are screened for the absence of reactivity against the control peptide. Consequently, of the CCP2-reactive, control peptide-negative cultures mRNA is isolated with TRIzol. cDNA is synthesized and an Anchoring Reverse Transcription of Immunoglobulin Sequences and Amplification by Nested (ARTISAN) PCR is performed to eventually determine the BCR sequence with Sanger sequencing.

For the second method, ten to thirty tetramer-positive B-cells are directly sorted in lysis buffer to obtain mRNA, followed by cDNA synthesis and preamplification according to the SMART-Seq protocol. As with the first protocol, immunoglobulin products were obtained by the ARTISAN PCR. In contrast with the first method, products were sequenced on the PacBio platform for next generation sequencing.

Results

82% ($^{23}/_{28}$) IgG, 0% (0/3) IgM and 0% (0/1) IgA ACPA antibodies sequenced with the single-cell sorting method, had an N-glycosylation site in the Fab-portion. With the multi-cell sorting and next generation sequencing method, 94% ($^{17}/_{18}$) IgG, 40% ($^{2}/_{5}$) IgM and 100% (9/9) IgA ACPA antibodies had an N-glycosylation site in the Fab-portion. In comparison, sequence analysis of the BCR repertoire of total B-cells obtained from healthy donors indicates that only around 9% of the antibodies contain an N-glycosylation site. From this data, it is clear that the percentage of ACPAs with an N-glycosylation site in the Fab region is significantly higher than the percentage in other sequences from healthy individuals.

The sequence data is supported by earlier-obtained data of increase of molecular weight by hyperglycosylation of ACPA-IgG in comparison to total or anti-tetanus IgG.[5]

Example 4

ACPA can Recognize and Bind to Acetylated-Peptides (Lysine and Ornithine)

Material and Methods

It was determined whether monoclonal and polyclonal ACPA antibodies can bind to a mutated vimentin peptide with different PTM. Monoclonal ACPA E4 IgG1 provided by Dr. Rispens (Sanquin) was analyzed for reactivity toward PTM-modified vimentin peptides. Polyclonal ACPA from RA patients was previously purified by gel filtration columns, purified ACPA 2.93 and 2.77.

For detection of reactivity toward PTM-modified vimentin peptide, an ELISA kit of Orgentec Diagnostica was used consisting of coated microplates containing PTM-modified vimentin peptides: HC52-homocitrulline, P62-arginine, P18-citrulline, HC55-acetylated lysine, HC56-lysine, acetylated-ornithine, and ornithine. Buffers were provided by the ELISA kit of Orgentec Diagnostica and consist of sample diluent buffer, conjugate anti-Human IgG-HRP+ reference secondary IgG conjugate, TMB substrate and stop solution. Purified ACPA and monoclonal ACPA were diluted in Orgentec Diagnostica sample diluent buffer until the desired concentrations (30 µg/ml for purified ACPA and ACPA E4 mAbs) and incubated on the ELISA plate. ACPA binding was detected by conjugate anti-human IgG-HRP and TMB. The optical density was measured at 450 nm (reference 600-690 nm).

Results

Figure 15:
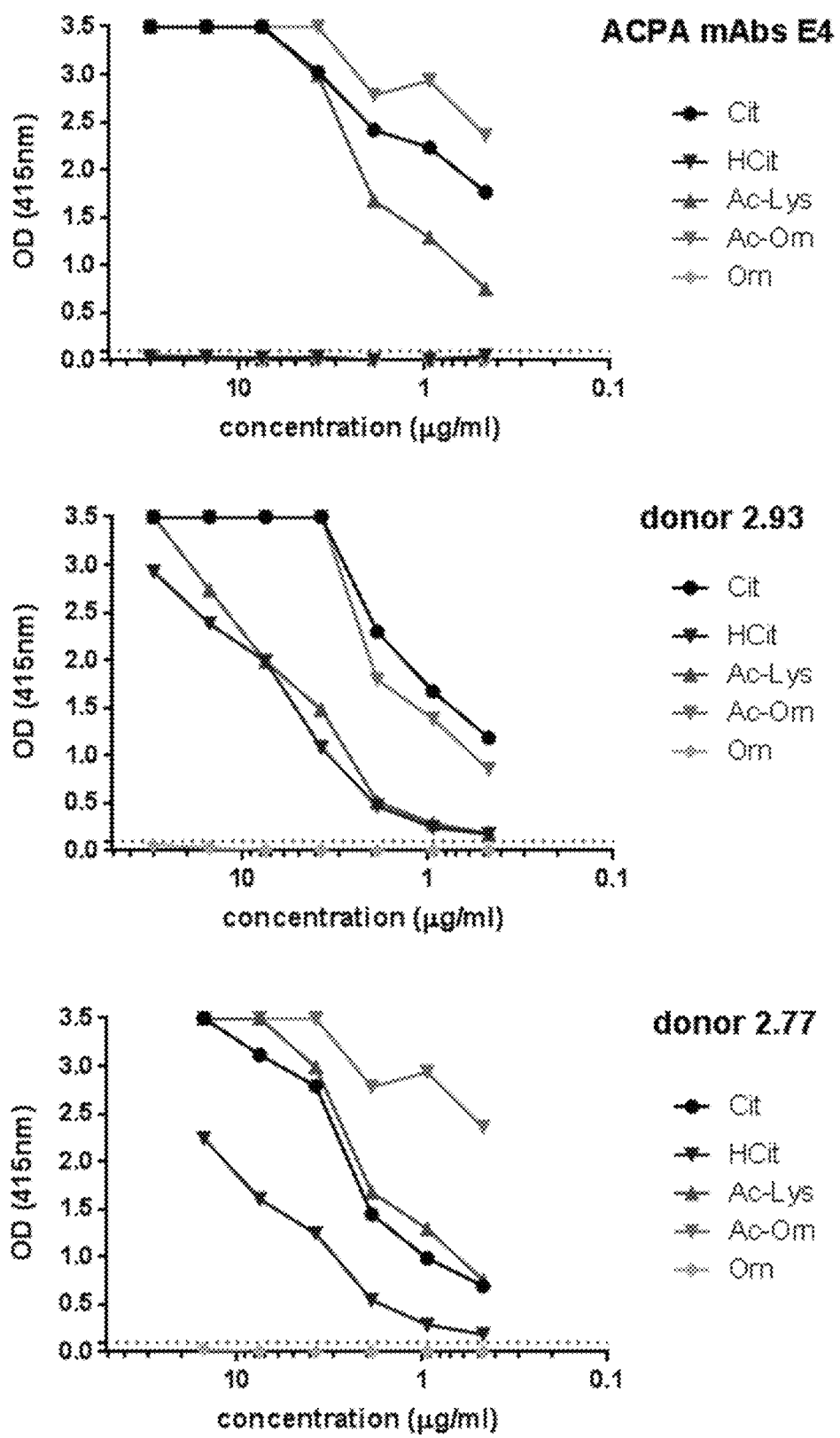
FIG. 15: ELISA with various antigens and antibody preparations.
Figure 18A:
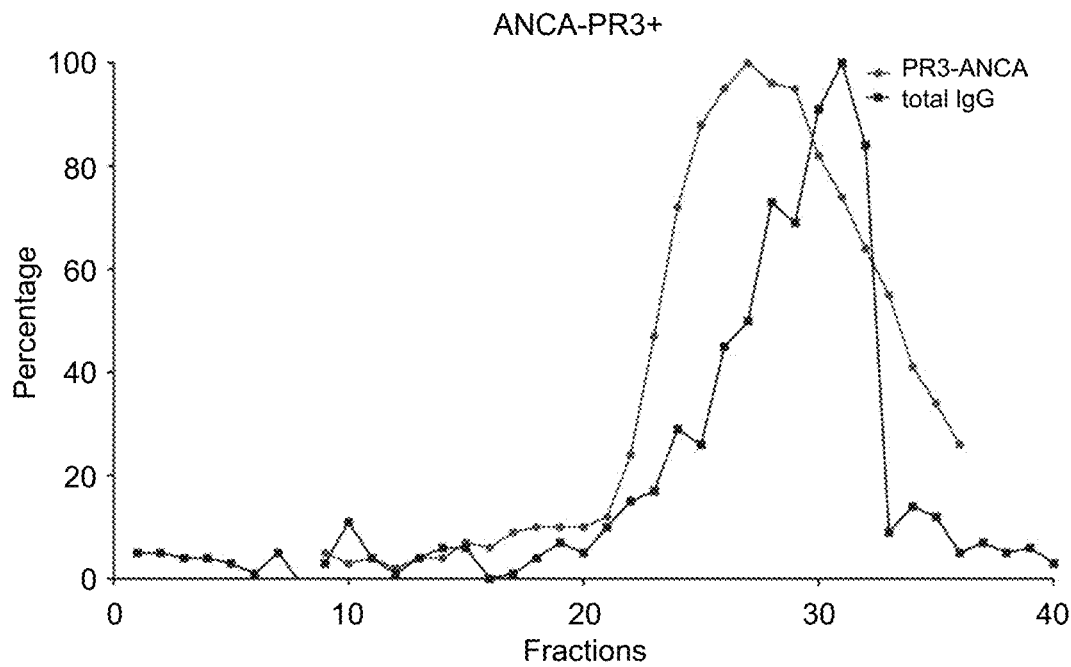
FIGS. 18A and 18B: Size shift as a result of N-glycosylation of an autoantibody Fab. The autoantibodies are PR3-ANCA antibodies, which are correlated AAV. Depicted are HPLC size fractionation fractions of total IgG and PR3-ANCA antibodies of one patient (FIG. 18A) and another patient (FIG. 18B). The autoantibodies are involved in bodies (ANCA) associated with vasculitis (AAV).
Figure 18B:
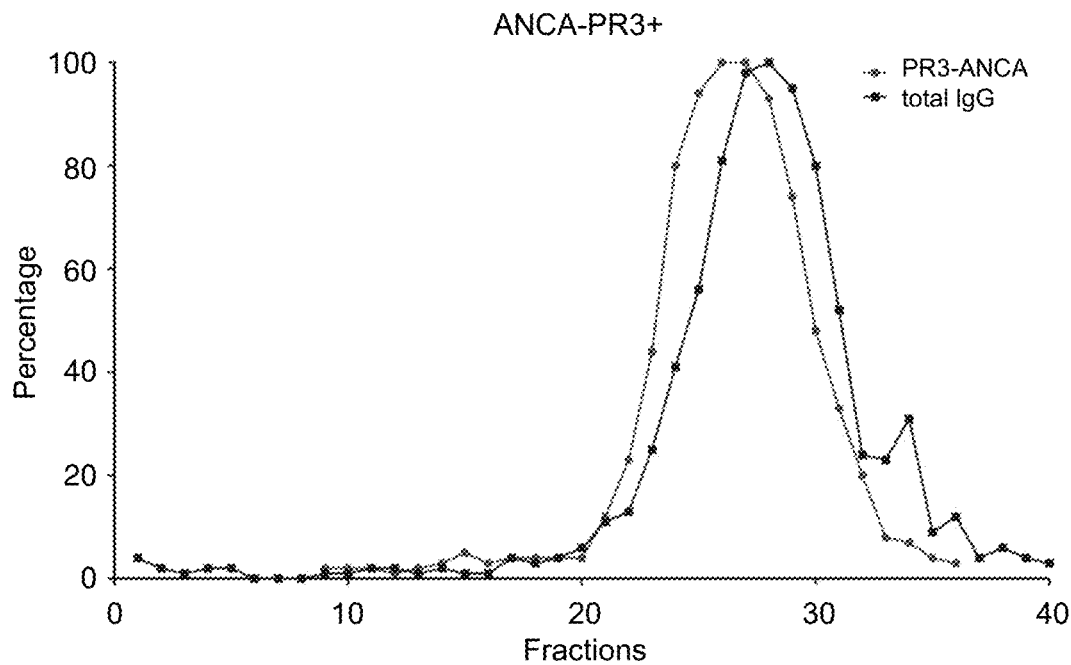

Monoclonal ACPA E4 is reactive toward the mutated vimentin peptide with post-translational modifications of citrulline, acetylated lysine and acetylated ornithine. Polyclonal ACPA from RA patient 2.93 is reactive toward mutated vimentin peptide with post-translational modifications of citrulline and acetylated ornithine. Polyclonal ACPA from RA patient 2.93 also harbors reactivity toward acetylated lysine and homocitrulline, although to a lesser extent. Polyclonal ACPA from RA patient 2.77 also binds mutated vimentin peptide with post-translational modifications of acetylated ornithine, acetylated lysine, citrulline and, to a lesser extent, homocitrulline (FIG. 15).

CONCLUSION

Monoclonal ACPA E4 and polyclonal ACPA obtained from RA patients (2.93 and 2.77) are reactive toward mutated vimentin peptide with post-translational modifications of citrulline, acetylated lysine and acetylated ornithine. Binding toward these different amino acids indicate that ACPA might be cross-reactive toward different PTMs.

CITED ART

1. Peschken, C. A. and J. M. Esdaile, *Rheumatic diseases in North America's indigenous peoples*. Semin. Arthritis Rheum., 1999. 28 (6): p. 368-91.
2. Ioan-Facsinay, A., et al., *Marked differences in fine specificity and isotype usage of the anti-citrullinated protein antibody in health and disease*. Arthritis Rheum., 2008. 58 (10): p. 3000-8.
3. Rombouts, Y., et al., *Extensive glycosylation of ACPA-IgG variable domains modulates binding to citrullinated antigens in rheumatoid arthritis*. Ann. Rheum. Dis., 2015.
4. Pucic, M., et al., *High throughput isolation and glycosylation analysis of IgG-variability and heritability of the IgG glycome in three isolated human populations*. Mol. Cell Proteomics, 2011. 10 (10): p. M111 010090.
5. Rombouts, Y., et al., *Extensive glycosylation of ACPA-IgG variable domains modulates binding to citrullinated antigens in rheumatoid arthritis*. Ann. Rheum. Dis., 2016. 75 (3): p. 578-85.
6. Stadlmann, J., et al., *A close look at human IgG sialylation and subclass distribution after lectin fractionation*. Proteomics, 2009. 9 (17): p. 4143-53.
7. Dalziel, M., I. McFarlane, and J. S. Axford, *Lectin analysis of human immunoglobulin G N-glycan sialylation*. Glycoconj. J., 1999. 16 (12): p. 801-7.
8. Guhr, T., et al., *Enrichment of sialylated IgG by lectin fractionation does not enhance the efficacy of immunoglobulin G in a murine model of immune thrombocytopenia*. PLOS One, 2011. 6 (6): p. e21246.
9. Arnett, F. C., et al., *The American Rheumatism Association 1987 revised criteria for the classification of rheumatoid arthritis*. Arthritis Rheum., 1988. 31 (3): p. 315-24.
10. Selman, M. H., et al., *Cotton HILIC SPE microtips for microscale purification and enrichment of glycans and glycopeptides*. Anal. Chem., 2011. 83 (7): p. 2492-9.
11. Rombouts, Y., et al., *Anti-citrullinated protein antibodies acquire a pro-inflammatory Fc glycosylation phenotype prior to the onset of rheumatoid arthritis*. Ann. Rheum. Dis., 2015. 74 (1): p. 234-41.
12. Falck, D., et al., *Glycoforms of Immunoglobulin G Based Biopharmaceuticals Are Differentially Cleaved by Trypsin Due to the Glycoform Influence on Higher-Order Structure*. J. Proteome Res., 2015. 14 (9): p. 4019-28.
13. Ruhaak, L. R., et al., *Glycan labeling strategies and their use in identification and quantification*. Anal. Bioanal. Chem., 2010. 397 (8): p. 3457-81.
14. Bondt, A., et al., *Immunoglobulin G (IgG) Fab glycosylation analysis using a new mass spectrometric high-throughput profiling method reveals pregnancy-associated changes*. Mol. Cell Proteomics, 2014. 13 (11): p. 3029-39.
15. Scherer, H. U., et al., *Immunoglobulin 1 (IgG1) Fc-glycosylation profiling of anti-citrullinated peptide antibodies from human serum*. Proteomics Clin. Appl., 2009. 3 (1): p. 106-15.
16. Scherer, H. U., et al., *Glycan profiling of anti-citrullinated protein antibodies isolated from human serum and synovial fluid*. Arthritis Rheum., 2010. 62 (6): p. 1620-9.
17. van de Stadt, L. A., et al., *Monoclonal anti-citrullinated protein antibodies selected on citrullinated fibrinogen have distinct targets with different cross-reactivity patterns*. Rheumatology (Oxford), 2013. 52 (4): p. 631-5.

Example 5

Material and Methods

Patients and Healthy Individuals

Peripheral blood samples were obtained from ACPA-positive patients with established RA. Patients were recruited from the outpatient clinic of the Department of Rheumatology at Leiden University Medical Centre (LUMC) and gave written informed consent. Healthy donor samples were obtained from leftover material collected for allogeneic stem cell transplantation and sequenced as described before.[1]

Isolation and Culture of Antigen-Specific B-Cells

ACPA-expressing B-cells were isolated from peripheral blood mononuclear cells (PBMC) as previously described.[2] Tetanus-toxoid (TT)-specific B-cells were isolated using directly labelled TT (Statens Serum Institute) prepared with the AnaTag™ Labeling Kit (ThermoFisher). Cells were sorted either in pools of 10 cells or as single cells as described.[3] One patient sample was processed following both methods. Presence of ACPA-IgG in culture supernatants was assessed by ELISA.[2]

mRNA Isolation and cDNA Processing

Cells sorted as pools were directly lysed using TRITON® X-100 (Sigma) followed by mRNA isolation. mRNA from single cell cultures was isolated using TRIZOL® (Thermo Fisher). Following either isolation procedure, cDNA was synthesized as described.[4]

ARTISAN PCR and Sequencing

Ig transcripts were amplified using Anchoring Reverse Transcription of Immunoglobulin Sequences and Amplification by Nested (ARTISAN) PCR, with modifications.[1]

PCR products of pooled cells were sequenced on the PacBio RSII system (Pacific Biosciences, Menlo Park, CA, USA). PCR products obtained from single cell cultures were sequenced with Sanger sequencing.[5] Sequence data were analyzed with Geneious R9.1.5[6] and IMGT (High) V-QUEST tools[7].

Results

Localization of N-Glycosylation Sites in ACPA BCR Sequences

Figure 19A:
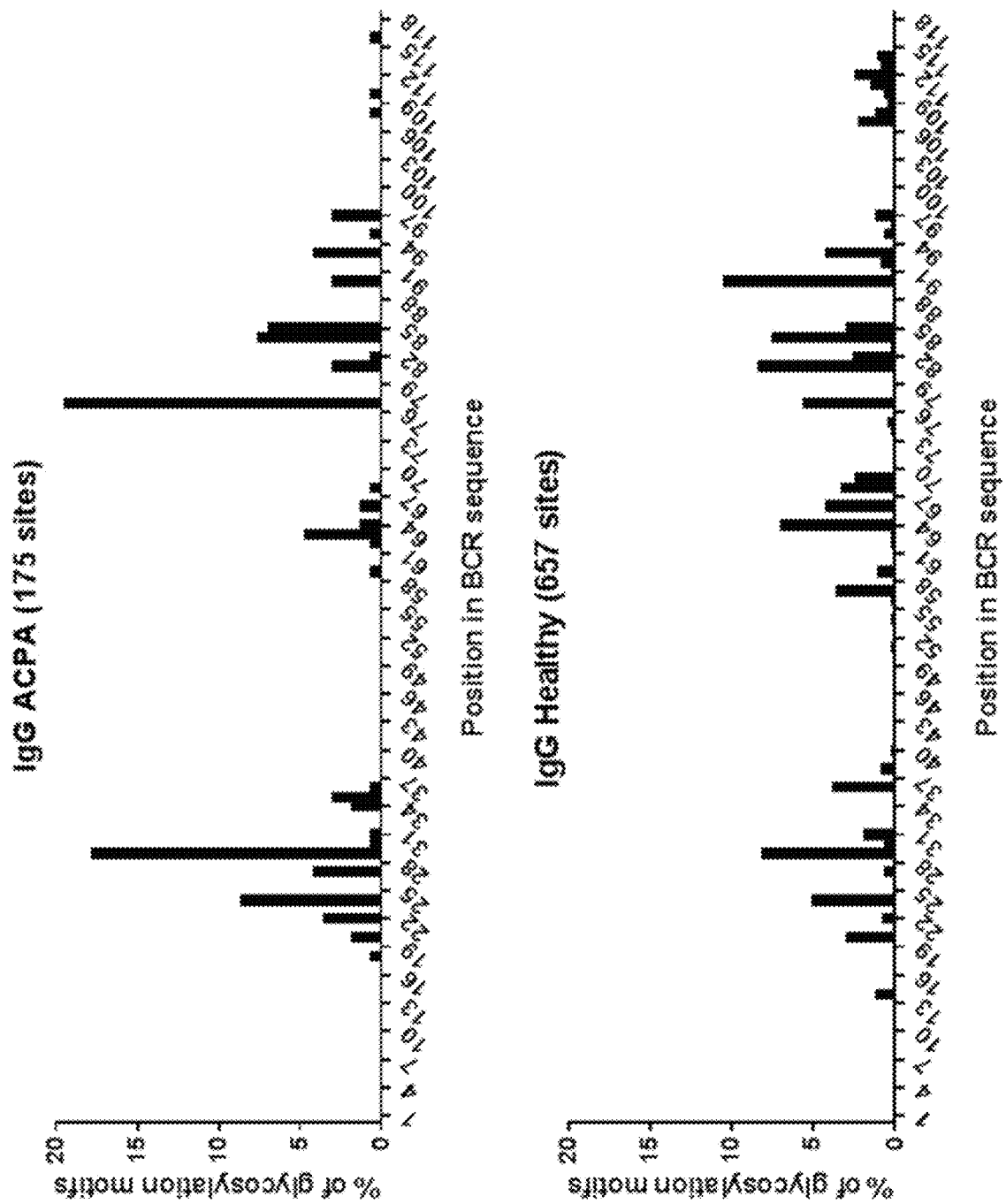
FIGS. 19A-19C: Localization of N-glycosylation sites in ACPA BCR sequences compared to sites in BCR sequences obtained from healthy individuals.
Figure 19B:
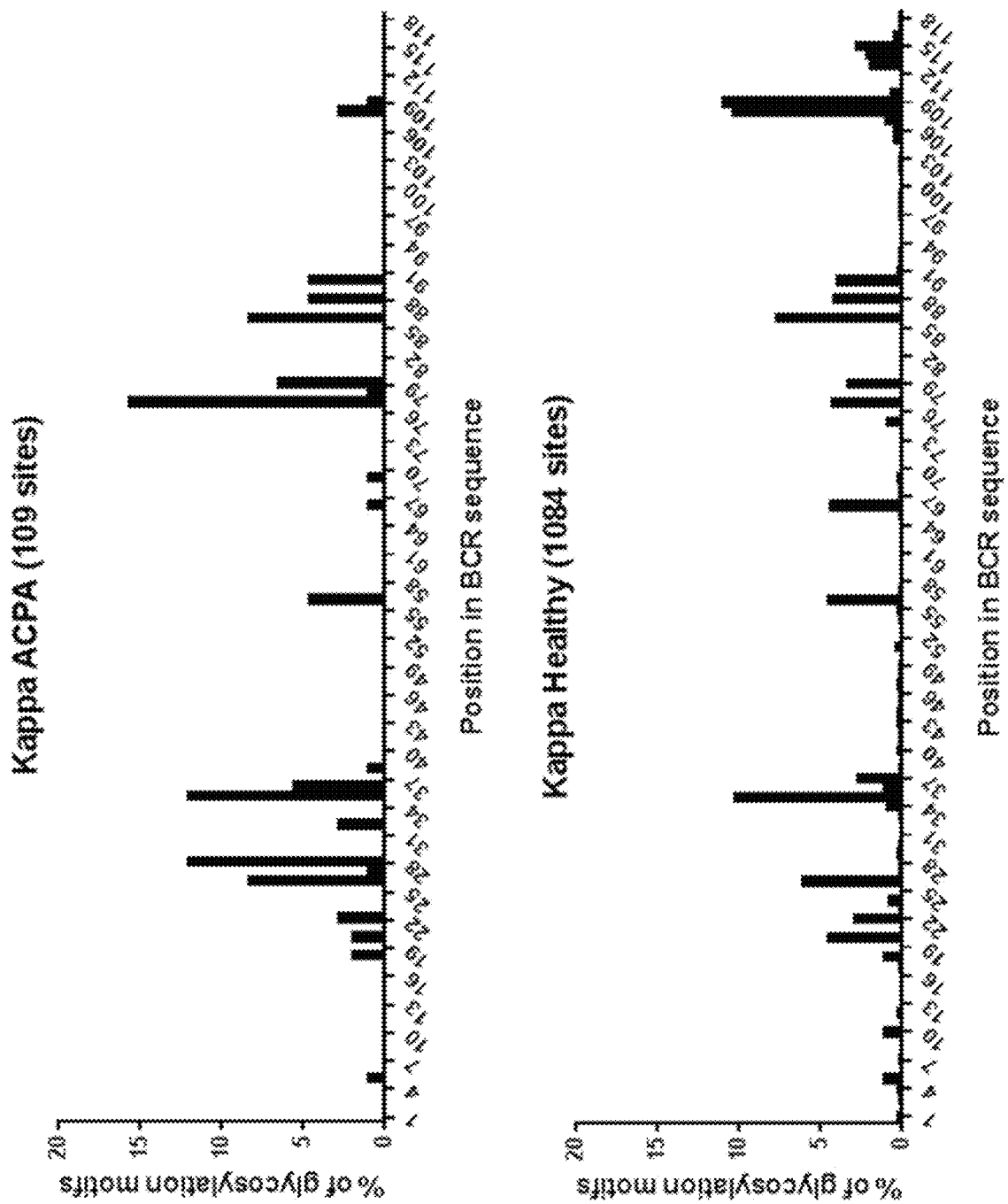
Figure 19C:
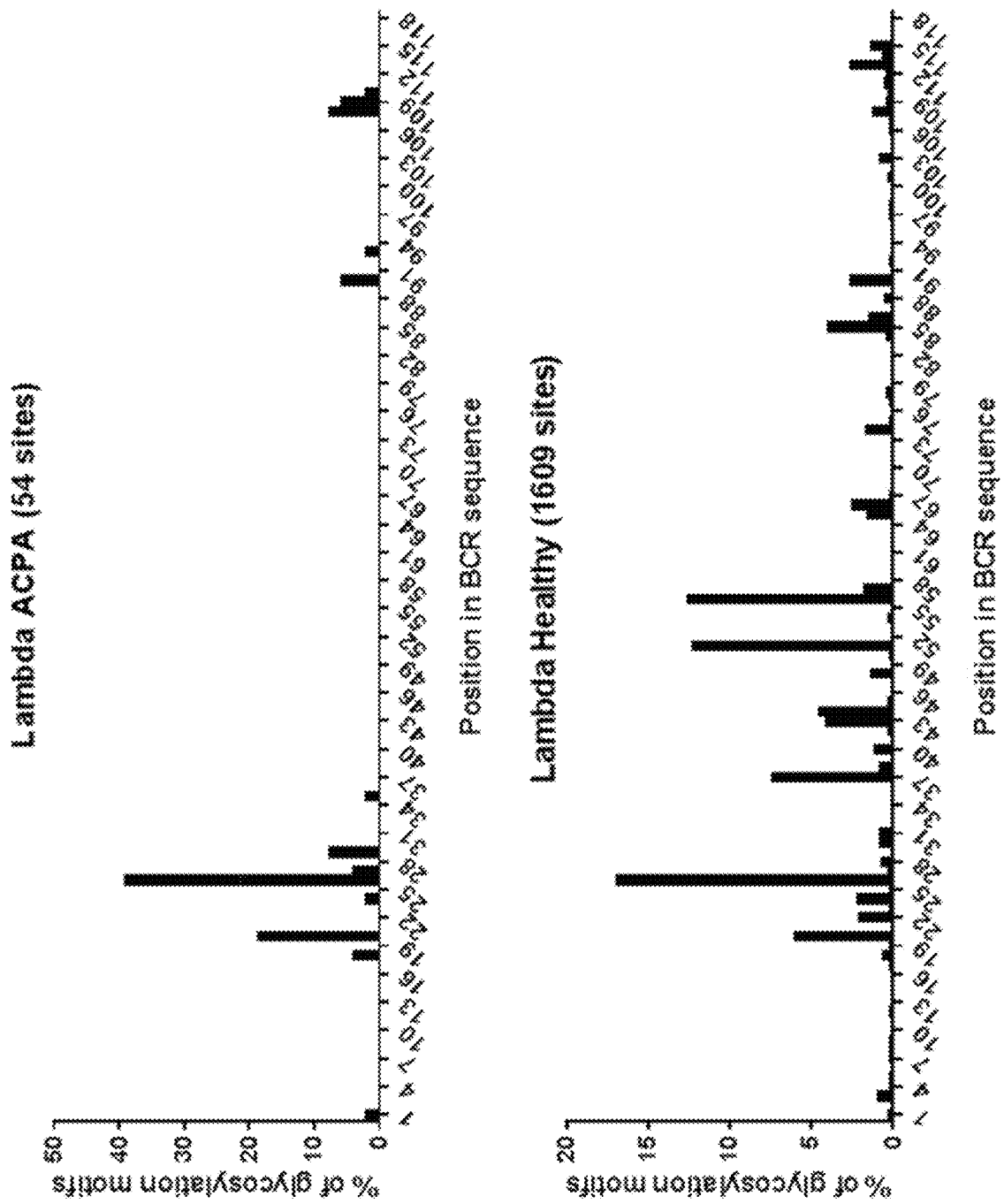

BCR sequences of citrulline-specific B-cells show a remarkable frequency of N-glycosylation sites. Their independence from the SHM rate suggests that N-glycans in the variable region confer selective advantages to ACPA-expressing B-cells during development and/or maturation. To obtain more insight into this possibility, the distribution of sites were studied and compared the pattern to N-glycosylation sites identified in healthy donor B-cell receptor (BCR) repertoires. For ACPA-IgG sequences, a predominance of sites in the CDR1 region and a relative absence in CDR3 regions of ACPA-IgG were observed. These results suggest that the N-glycosylation site distribution pattern of ACPA-IgG is skewed away from the CDR3 region and indicate a certain preference for glycans in the CDR1 region.[8] More specifically, by assessing the V genes of the IgG heavy chain, kappa light chain and lambda light chain in detail, enrichment of sites on specific positions in the BCR sequence and lack of sites on other positions were observed. Considering the V-gene of the IgG heavy chain and kappa light chain, a similar pattern, enrichment of sites on positions 29 and 77 and a lower abundance of sites on several positions in the CDR3 region were observed. In the lambda light chain, there seems to be a lack of sites in positions 37, 51, 56, which are highly present in BCR sequences obtained from healthy individuals (FIG. 19).

Cited Art (Example 5)

1 Koning, M. T. et al., ARTISAN PCR: rapid identification of full-length immunoglobulin rearrangements without primer binding bias. Br. J. Haematol., doi: 10.1111/bjh.14180 (2016).

2 Kerkman, P. F. et al., Identification and characterisation of citrullinated antigen-specific B cells in peripheral blood of patients with rheumatoid arthritis. Ann. Rheum. Dis. 75, 1170-1176, doi: 10.1136/annrheumdis-2014-207182 (2016).

3 Lighaam, L. C. et al., Phenotypic differences between IgG4+ and IgG1+B cells point to distinct regulation of the IgG4 response. J. Allergy Clin. Immunol. 133, 267-270.e261-266, doi: 10.1016/j.jaci.2013.07.044 (2014).

Trombetta, J. J. et al., Preparation of Single-Cell RNA-Seq Libraries for Next Generation Sequencing. Curr. Protoc. Mol. Biol. 107, 4 22 21-17, doi: 10.1002/0471142727.mb0422s107 (2014).

5 Sanger, F. & Coulson, A. R., A rapid method for determining sequences in DNA by primed synthesis with DNA polymerase. Journal of molecular biology 94, 441-448 (1975).

6 Kearse, M. et al., Geneious Basic: an integrated and extendable desktop software platform for the organization and analysis of sequence data. Bioinformatics (Oxford, England) 28, 1647-1649, doi: 10.1093/bioinformatics/bts199 (2012).

7 Alamyar, E., Duroux, P., Lefranc, M. P. & Giudicelli, V., IMGT((R)) tools for the nucleotide analysis of immunoglobulin (IG) and T cell receptor (TR) V-(D)-J repertoires, polymorphisms, and IG mutations: IMGT/V-QUEST and IMGT/HighV-QUEST for NGS. Methods in molecular biology (Clifton, N.J.) 882, 569-604, doi: 10.1007/978-1-61779-842-9 32 (2012).

8 Vergroesen, R. D. et al., B-cell receptor sequencing of anti-citrullinated protein antibody (ACPA) IgG-expressing B cells indicates a selective advantage for the introduction of N-glycosylation sites during somatic hypermutation. Annals of the rheumatic diseases, doi: 10.1136/annrheumdis-2017-212052 (2017).

Example 6

Methods for the Detection of ACPA-Fab Glycans

Figure 22A:
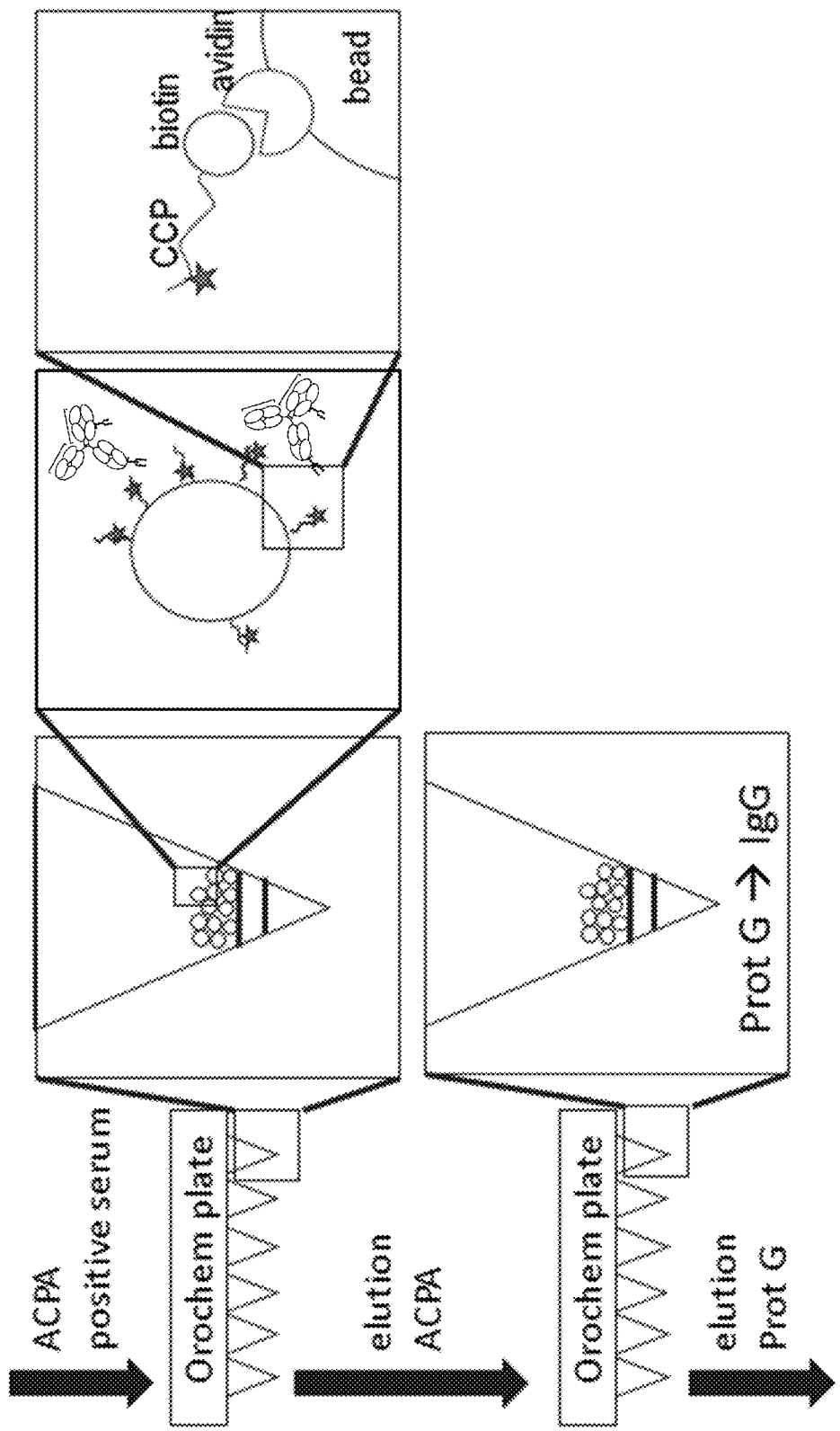
FIGS. 22A-22C: High-end UHPLC and mass spectrometry analyses of purified ACPA-IgG.
Figure 22B:
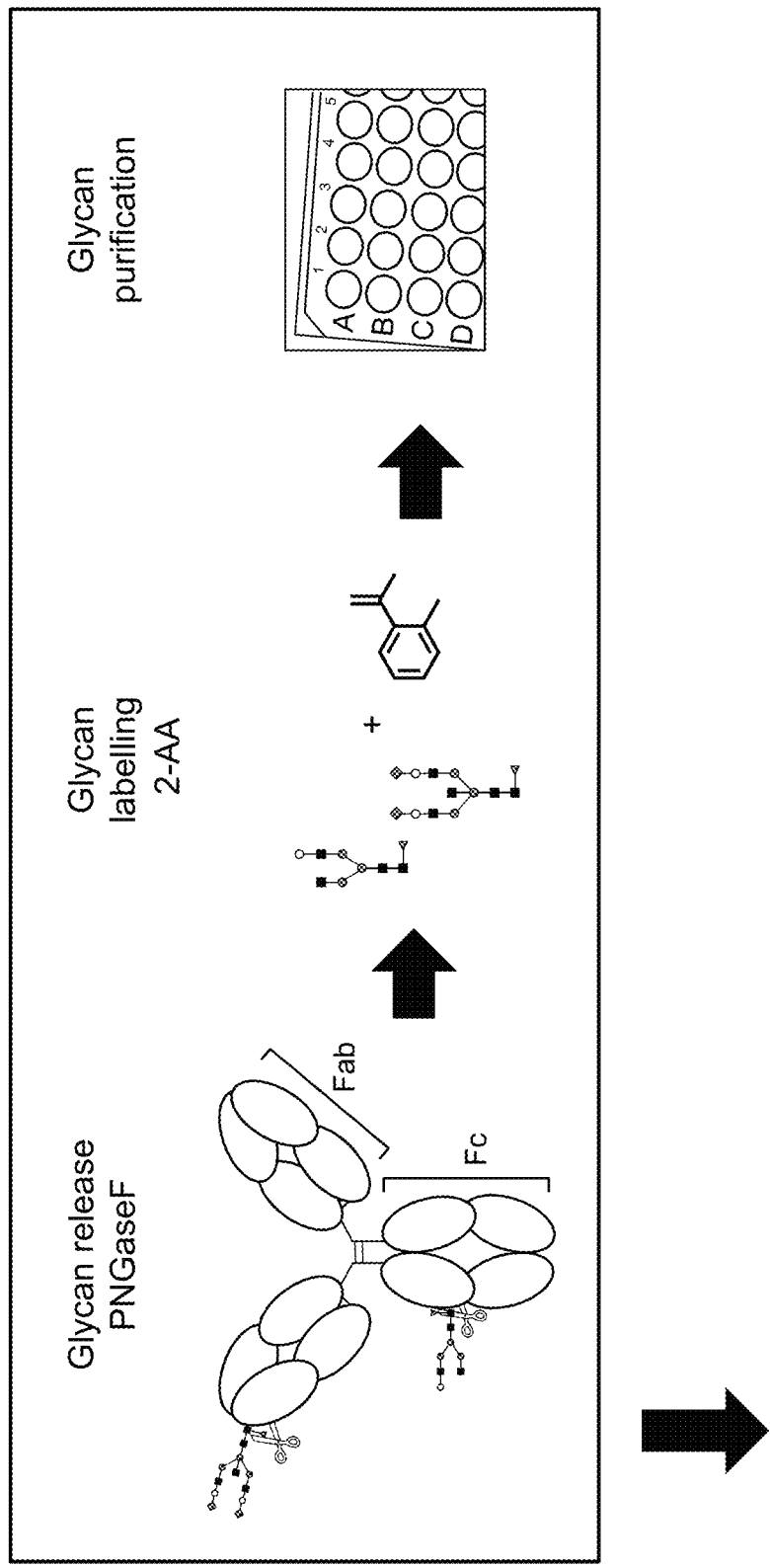
Figure 22C:
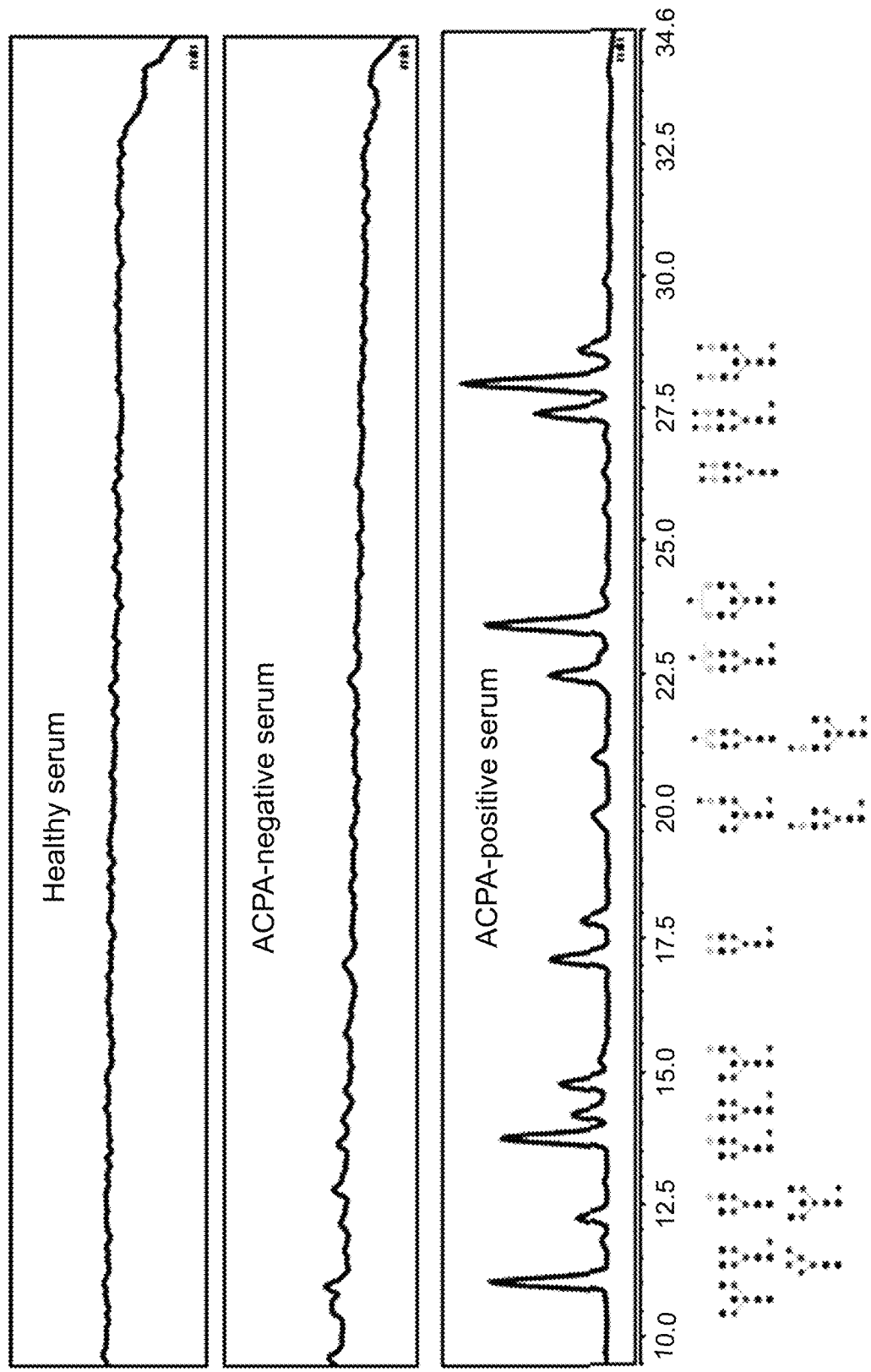

Method 1:

High-end UHPLC and mass spectrometry analyses of purified ACPA-IgG were used (FIG. 22).

ACPA-IgG was isolated with the CCP2 microbeads assay as it was described before[1]. Briefly, the CCP2-biotinylated peptide was coupled to neutravidin beads by incubating the beads with peptide for 1 hour at room temperature (RT) while shaking 850 rpm. After the incubation, the beads were washed with PBS to remove uncoupled peptide. Then, 25 µl of the beads slurry (25% beads per ml) was placed in an orochem filter plate. Thereafter, the 25-75 µl serum/plasma was loaded and PBS was added to an end volume of 200 µl per well and incubated for 2 hours at RT while shaking at 600 rpm. After collecting the flow-through by spinning the plate at 500 g for 1 minute, the beads were again washed with PBS three times by spinning the plate at 500 g for 1 minute. ACPA was eluted by 2×100 µl 100 mM Formic acid (FA) and neutralized with 2 M Tris to a pH of 7. The ACPA elution was further purified by using a similar technique as described above, but instead of CCP2 beads, 20 µl of 50% slurry prot G beads was used. The ACPA elution were incubated 1 hour at RT at 900 rpm and again eluted in 100 µl 100 mM formic acid. The elutions, now containing ACPA-IgG, were dried using a Speedvac. Glycans were released by resolubilizing the dried ACPA-IgG in 10 µl 2% SDS and 5 µl PBS and denatured for 30 minutes at 60° C. Ten, 10 µl PNGaseF solution (1:1 1% NP-40/5×PBS containing 0.5 U PNGaseF) was added and incubated overnight at 37° C. The next day, 12.5 µl 2-PB buffer and 12.5 µl 2AA-label was added and incubated 2 hours at 60° C. to label the released glycans.[2, 3] The 2-AA-labelled glycans were purified by HILIC SPE using cotton tips as described previously with some modifications.[4] Briefly, for each sample, 500 µg of cotton was packed into a 200 µl pipette tip and conditioned by pipetting three times 150 µl MQ, followed by 150 µl 85% ACN 0.1% TFA and two times 150 µl 85% ACN. The sample (in 85% ACN) was loaded by pipetting 25 times into the reaction mixture. The tips were washed three times with 150 µl 85% ACN 0.1% TFA and two times 150 µl 85% ACN. The 2-AA-labelled glycans were finally eluted from the cotton with 30 µl MQ and identified by MALDI-TOF-MS and/or UHPLC.

The protocol described in Method 1 is time consuming and requires high-end UHPLC analysis and expertise. Therefore, a more accessible method for use in day-to-day routine is preferable. Methods 2 and 3 are preferable, however, optimization experiments are required. The lectin SNA (Sambuccus Nigra Agglutinin) binds antibodies, primarily if these carry two sialic acid residues in the Fab domain.[5,6] SNA binds the antibody Fc tail only under reducing conditions (which opens up the interface between CH2 domains).[7, 8] ACPA F(ab)-glycans contain a high degree of di-sialylated glycans, which are virtually absent from the (ACPA-)IgG Fc tail. Therefore, SNA-binding to serum antibodies from RA-patients to detect ACPA F(ab)-glycans represents a promising strategy to visualize the presence of glycosylated antibodies. Method 2, as well as method 3, describe two approaches to establish a high-throughput method based on SNA-detection.

Figure 3B:
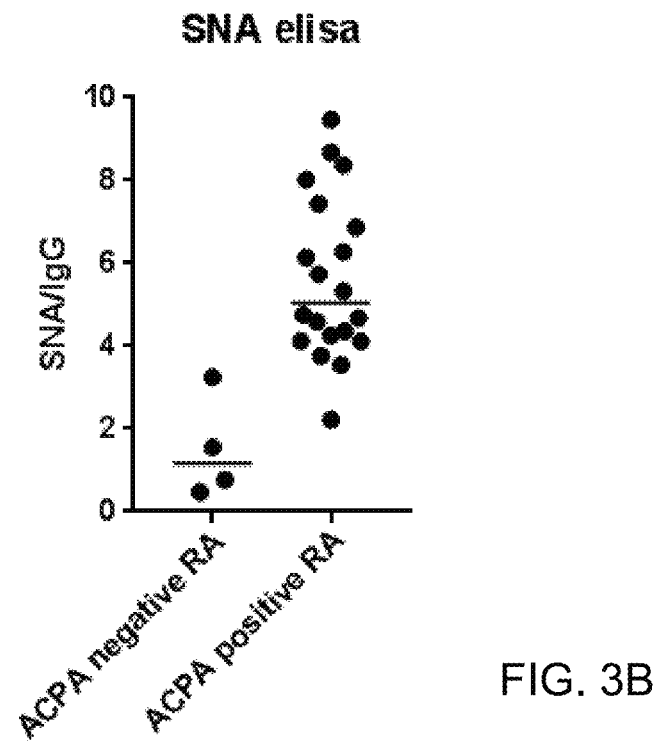
Figure 3C:
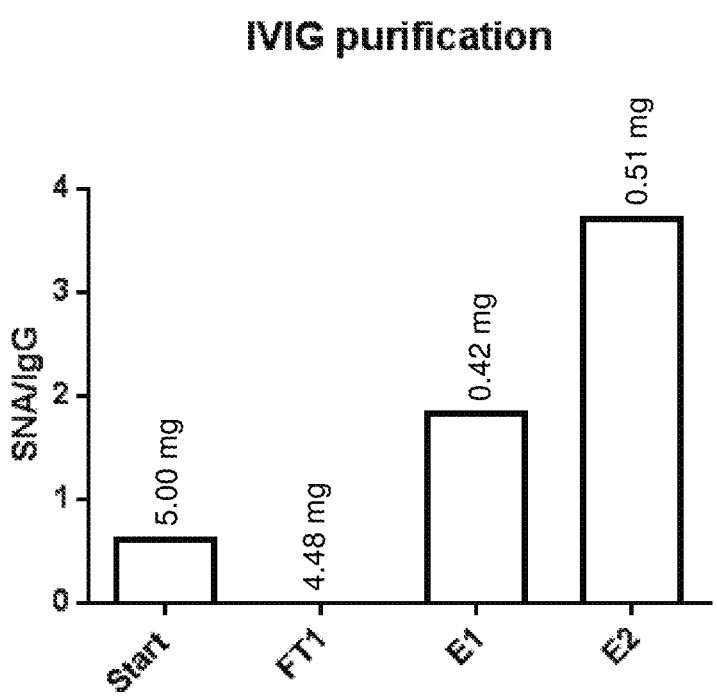
Figure 5A:
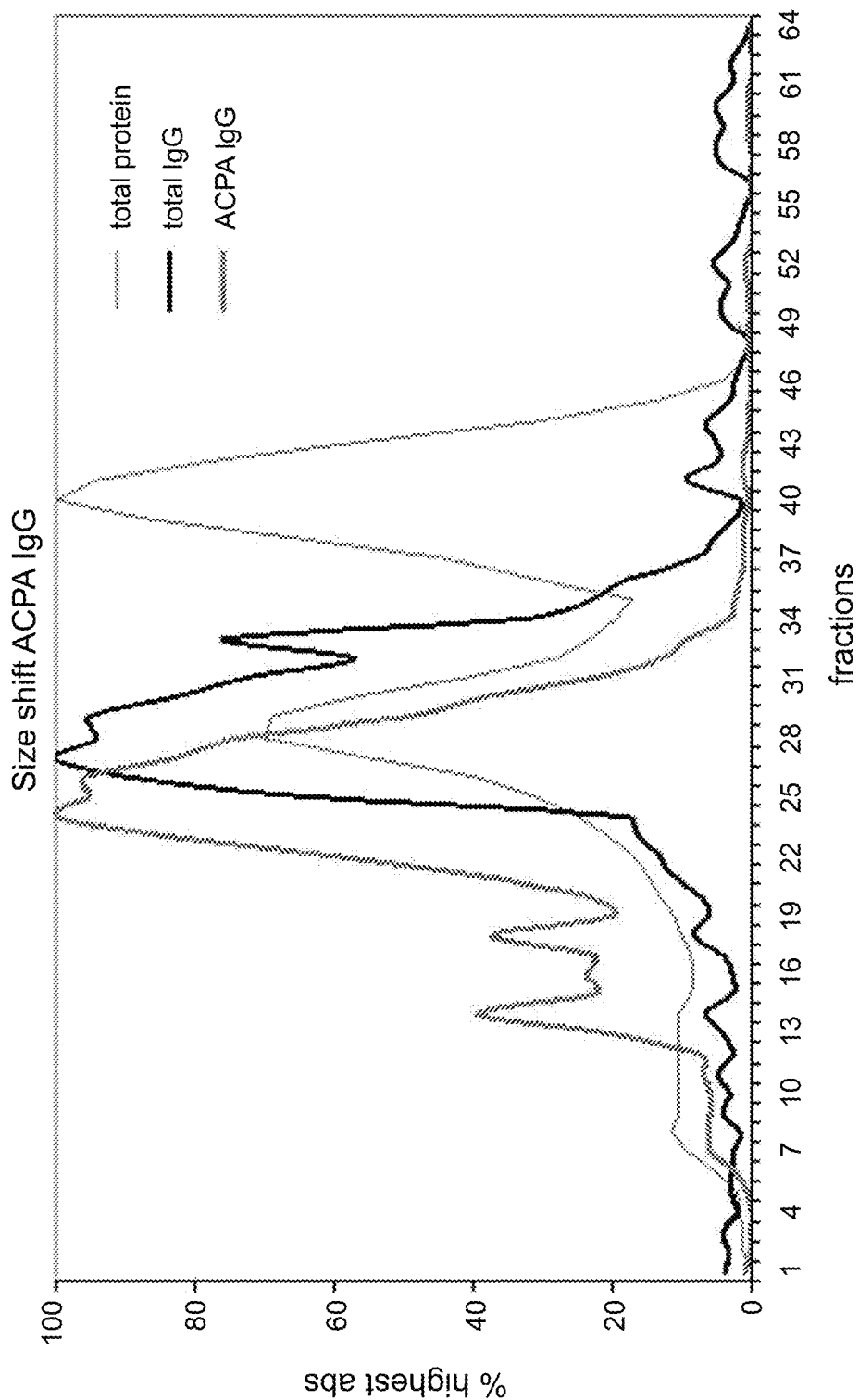
FIGS. 5A-5C: Size shift of ACPA and anti-carbamylated protein antibodies with respect to normal antibodies, i.e., not directed towards (homo-) citrullinated proteins (in this case anti-tetanus toxoid).
Figure 5B:
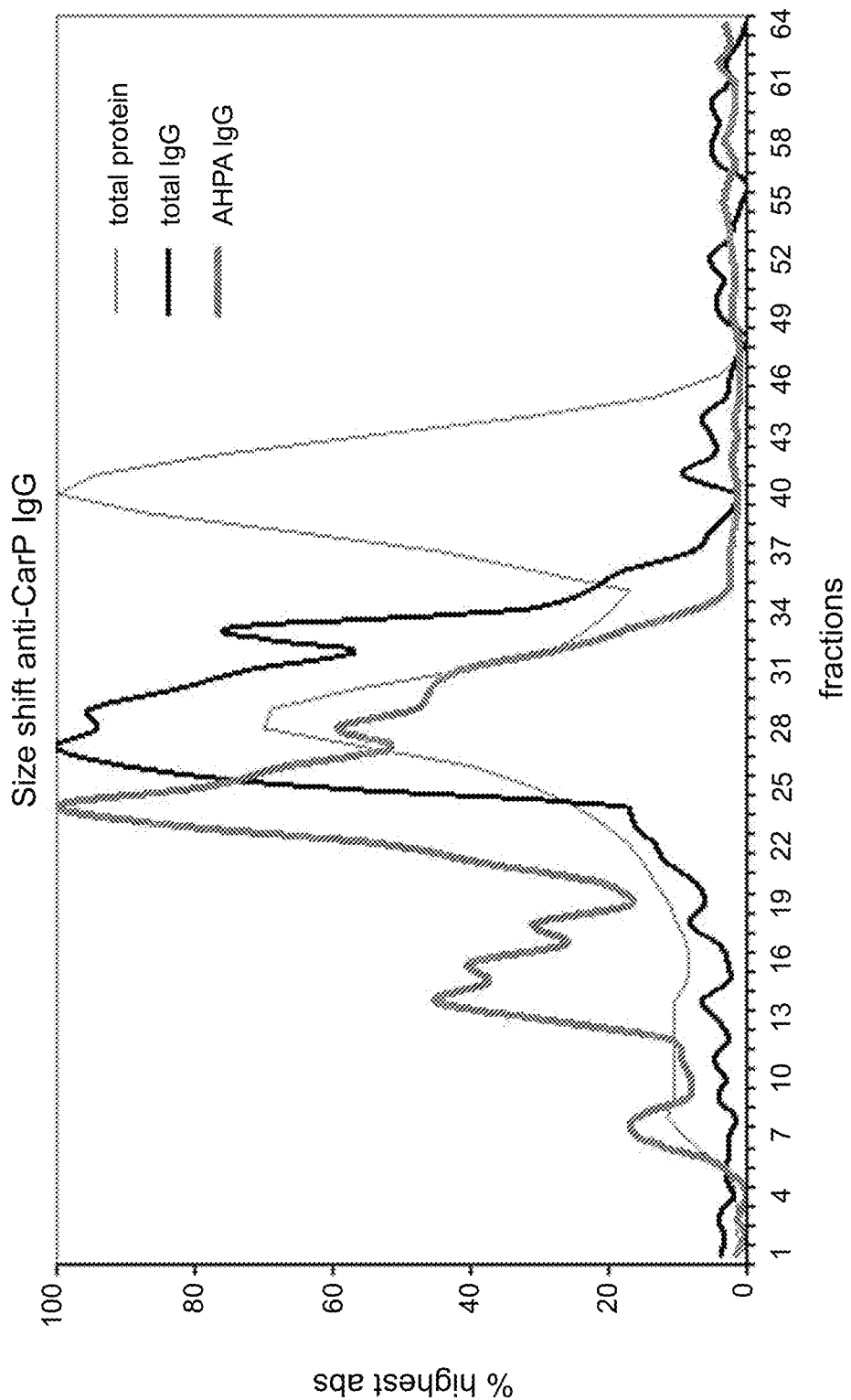
Figure 5C:
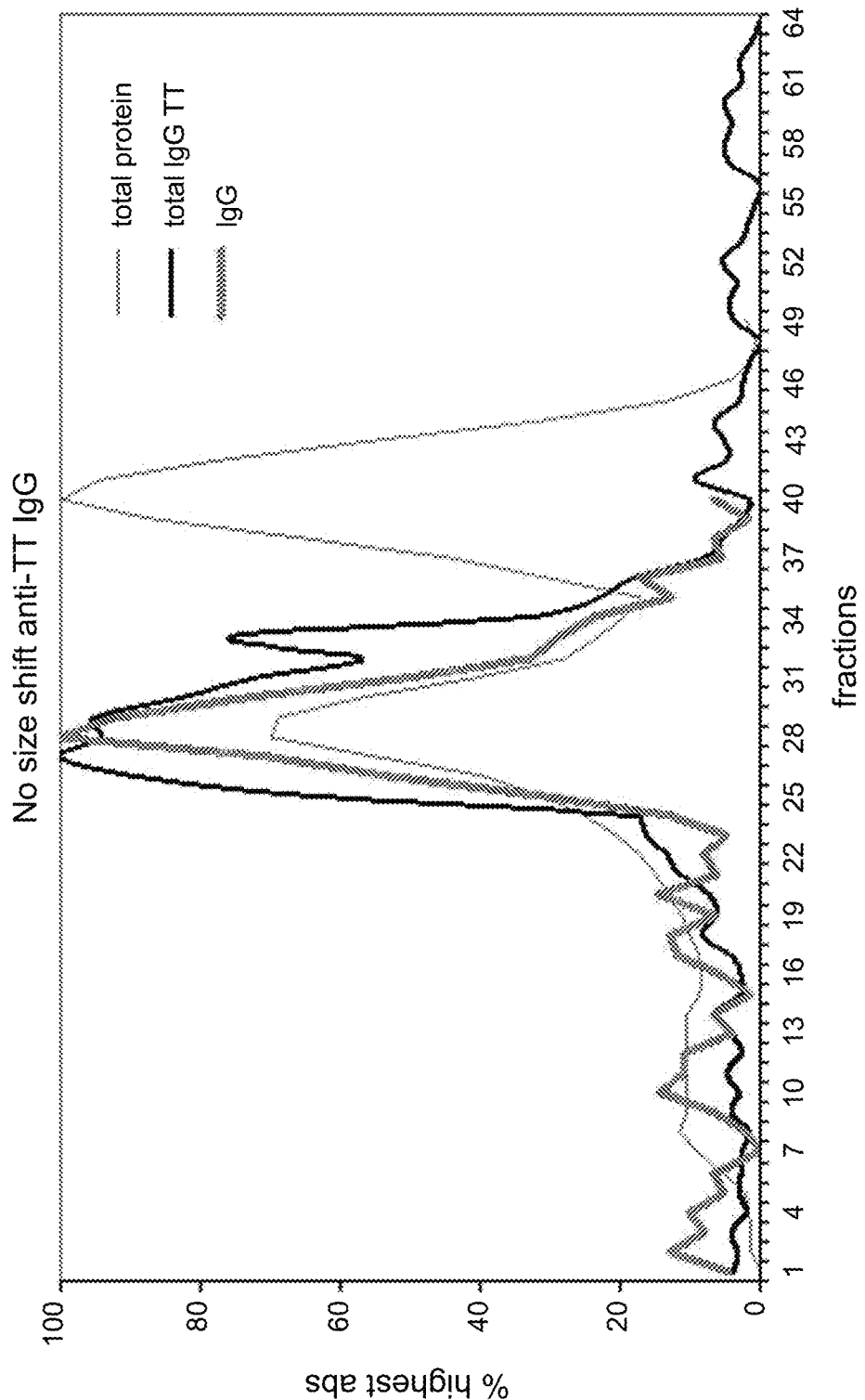

Method 2:

For method 2 (FIGS. 3A-3C), ACPA is captured using CCP2 coated microbeads (left panel) as described above. To calculate the presence of F(ab) glycans on ACPA IgG molecules, two different ELISAs are used. The first ELISA to visualize sialylated ACPA by an SNA-based lectin is depicted in FIG. 3A, right panel. For the second ELISA, to calculate the amount of ACPA IgG, a kit from Bethyl is used (Human IgG ELISA Kit, E88-104). For both ELISAs, plates were first coated with 10 µg/ml peroic acid-treated goat-anti-human IgG Fc capture antibody. Two hundred mM peroic acid was incubated for 30 minutes at 4° C. to destroy the sialic acid present on the goat-anti-human antibody and for 1 hour at RT. The plates were washed 3× with PBS 0.05% TWEEN® buffer and then blocked with 1% BSA-PBS (again treated with 20 mM PA overnight at 4° C.) for 1 hour at RT. After washing the plates, the eluted ACPA elution (FIG. 3A left panel) were added to both plates and incubated for 1 hour at RT. After incubation and washing, one plate was incubated with 2 µg/ml biotinylated SNA for 1 hour at RT and the other plate was incubated with goat-anti-human IgG HRP for 1 hour at RT. Again, after the incubation, the plates were washed. Subsequently, ABTS was added to the plate previously incubated with goat-anti-human IgG HRP, and the absorbance was measured at 415 nm. To the plate previously incubated with SNA, Strep-HRP was added and incubated for 1 hour at RT. After the incubation, the absorbance was measured by a similar approach. For the analysis of the results, both plates contained a standard curve.

SNA binding per µg ACPA-IgG was calculated by dividing the SNA binding to ACPA-IgG on plate 1 by the µg ACPA-IgG captured on plate 2. The higher the binding of SNA per µg ACPA-IgG, the higher the amount of ACPA Fab glycosylation. The results clearly show enhanced SNA-to-IgG ratio in the ACPA-positive samples, visualizing the high glycosylated content in Fab from ACPA.

Figure 23A:
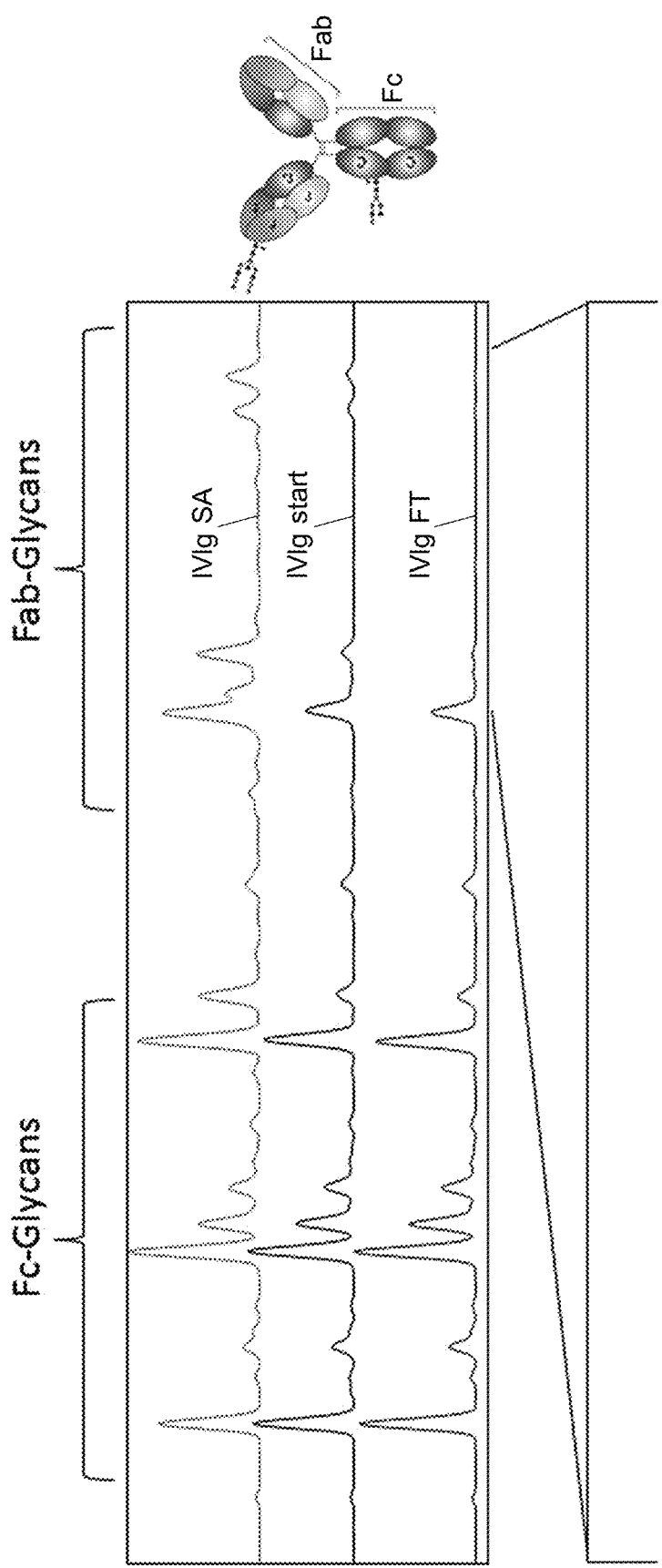
FIGS. 23A and 23B: IVIG was fractionated using the setup detailed in FIGS. 4A.1-4B, followed by UPLC analysis (upper graph) of total IgG molecules and of IgG Fab fragments (lower graph). Data show that SNA-purification enriched for IgG molecules containing highly sialylated Fab fragments (top lines in the graphs), whereas these were absent in the SNA-flow through fraction (bottom lines in the graphs). Of note, IVIG contains ~15% of Fab-glycosylated IgG molecules (middle lines in the graphs).
Figure 23B:
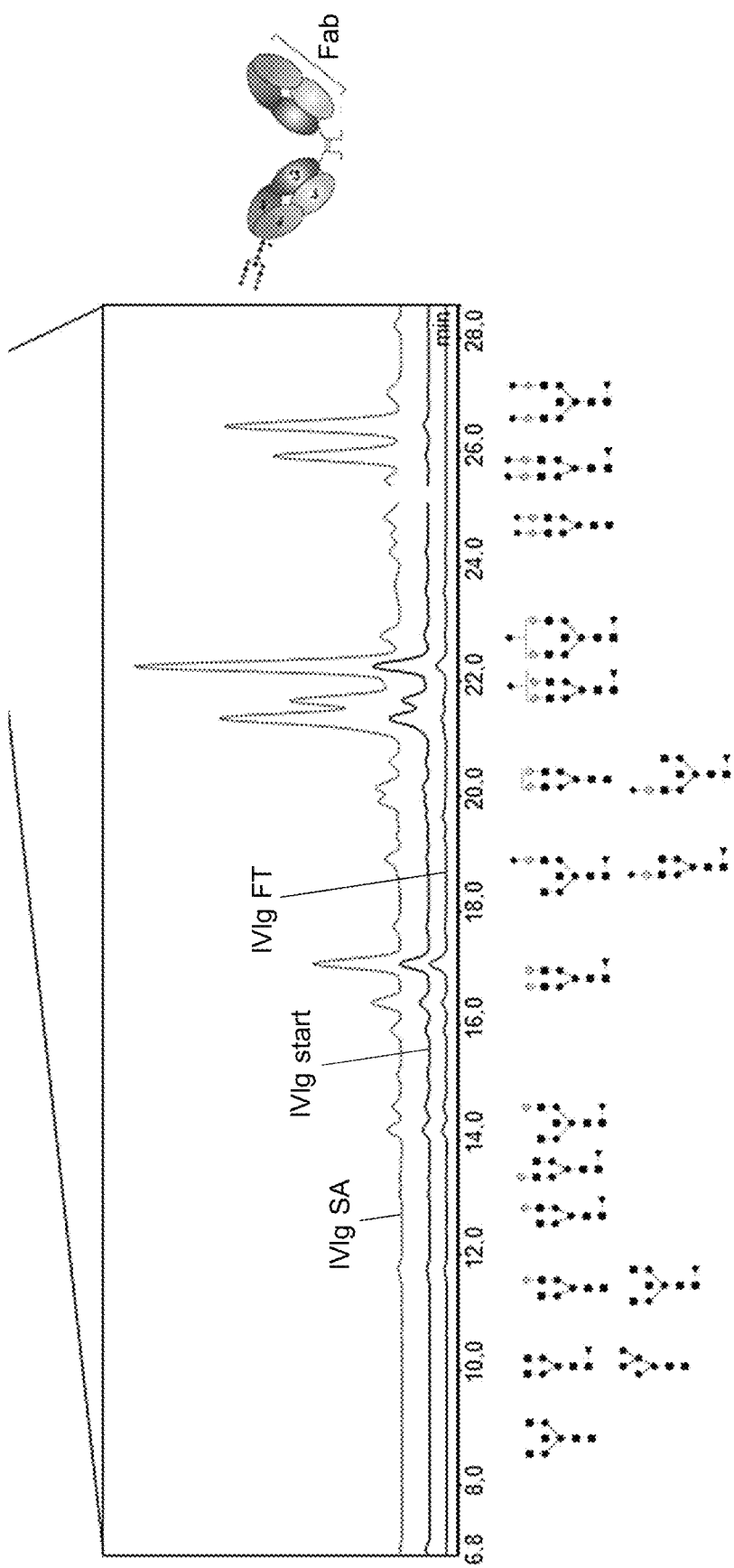
Figure 24A:
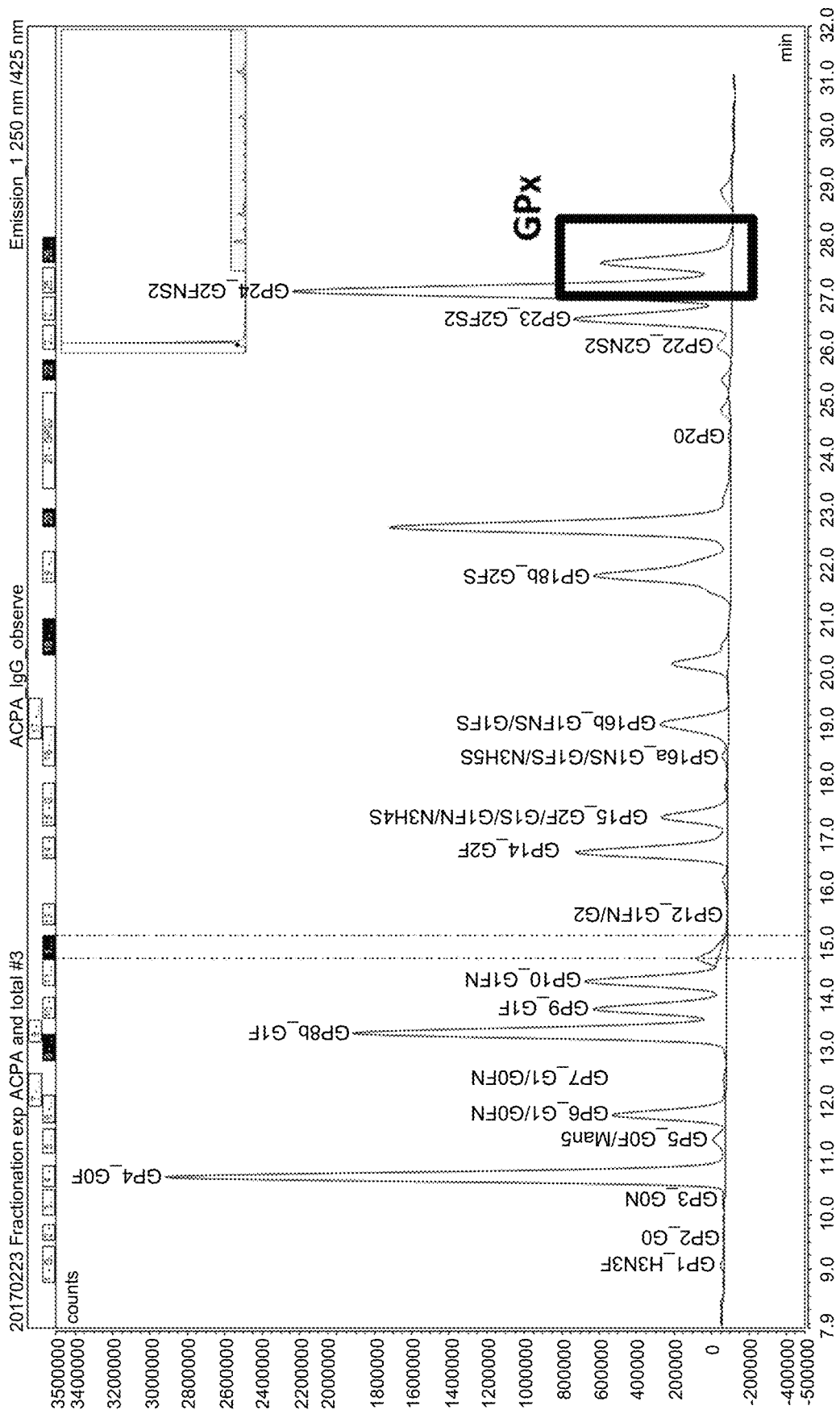
FIGS. 24A and 24B: Identification of triantennary glycans on ACPA-IgG using UHPLC, LC-MS and MALDI-TOF-MS-MS.
Figure 24B:
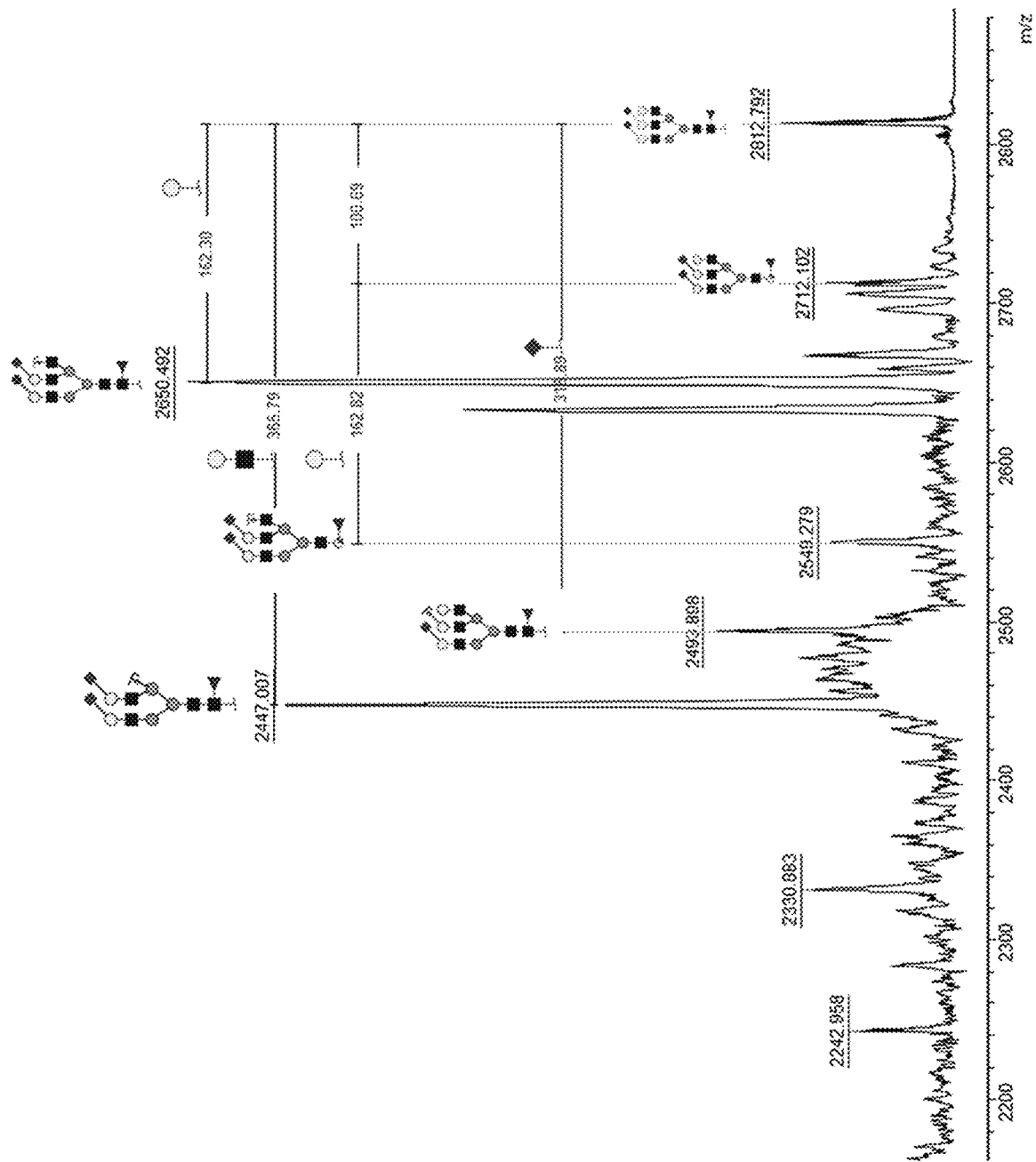

Method 3:

For method 3, a reverse strategy is used. First, total IgG from serum or plasma is isolated by a similar approach as the micro bead assay described before. This is followed by immobilizing IgG on SNA by SNA agarose beads. Finally, ACPA-IgG is detected using a CCP ELISA on the SNA elution and flow-through fractions (FIGS. 4A.1-4B). Due to the high amount of di-sialylated Fab glycans present on ACPA-IgG, an enrichment of CCP reactivity is expected in the SNA elution fraction. This approach is feasible for ACPA-IgG and can be used in a high throughput manner, as shown in FIG. 4B (right panel). Importantly, it was confirmed that SNA agarose beads indeed capture Fab glycosylated IgG in this set-up, as UHPLC analysis of IVIG samples indicates that we could clearly enrich for Fab glycosylated IgG molecules contained in IVIG in the SNA elution fractions (FIGS. 23A and 23B). Thus, the data depicted in FIGS. 4A.1-4B also show the feasibility of this approach and visualize the presence or highly-glycosylated Fab-domains of ACPA. Of note, pre-isolation of IgG by protein G is important to prevent "overloading" of SNA beads by other molecules present in serum that carry sialylated glycans. However, with adjusting the amount of serum loading on SNA beads, the method can also be used in reverse.

Methods 2 and 3 both show the robustness, specificity and reliability to detect F(ab) glycans. Together, these experiments show that an assay system that quickly and reliably identifies ACPA F(ab) glycans has been established.

Cited Art (Example 6)

1 Habets, K. L. et al., Anti-citrullinated protein antibodies contribute to platelet activation in rheumatoid arthritis. Arthritis research & therapy 17, 209, doi: 10.1186/s13075-015-0665-7 (2015).

2 Hafkenscheid, L. et al., Structural Analysis of Variable Domain Glycosylation of Anti-Citrullinated Protein Antibodies in Rheumatoid Arthritis Reveals the Presence of Highly Sialylated Glycans. Molecular & cellular proteomics: MCP 16, 278-287, doi: 10.1074/mcp.M116.062919 (2017).

3 Rombouts, Y. et al., Extensive glycosylation of ACPA-IgG variable domains modulates binding to citrullinated antigens in rheumatoid arthritis. Annals of the rheumatic diseases 75, 578-585, doi: 10.1136/annrheumdis-2014-206598 (2015).

4 Selman, M. H. et al., Fc-specific IgG glycosylation profiling by robust nano-reverse phase HPLC-MS using a sheath-flow ESI sprayer interface. Journal of proteomics 75, 1318-1329, doi: 10.1016/j.jprot.2011.11.003 (2012).

5 Kasermann, F. et al., Analysis and functional consequences of increased Fab-sialylation of intravenous immunoglobulin (IVIG) after lectin fractionation. PLOS One 7, e37243, doi: 10.1371/journal.pone.0037243 (2012).

6 Guhr, T. et al., Enrichment of sialylated IgG by lectin fractionation does not enhance the efficacy of immunoglobulin G in a murine model of immune thrombocytopenia. PLOS One 6, e21246, doi: 10.1371/journal.pone.0021246 (2011).

7 Stadlmann, J. et al., A close look at human IgG sialylation and subclass distribution after lectin fractionation. Proteomics 9, 4143-4153, doi: 10.1002/pmic.200800931 (2009).

8 Dalziel, M., McFarlane, I. & Axford, J. S., Lectin analysis of human immunoglobulin G N-glycan sialylation. Glycoconj. J. 16, 801-807 (1999).

The invention claimed is:

1. A method of determining whether an antibody sample comprises an anti-modified protein antibody (AMPA), the method comprising:
    contacting antibodies of the antibody sample with a peptide or protein that comprises a modified protein epitope, wherein the modified protein epitope comprises citrulline, homo-citrulline, or acetylated lysine;
    contacting antibodies of the antibody sample with a molecule that binds an N-linked glycan on a Fab-portion of an antibody; and
    determining whether an antibody with an N-linked glycan on a Fab-portion of the antibody has bound to the modified protein epitope in the peptide or protein so as to determine whether the antibody sample comprises AMPA.

2. The method according to claim 1, wherein the AMPA is a citrulline, a homo-citrulline, and/or an acetylated lysine binding AMPA.

3. The method according to claim 1, wherein the antibody sample is from an individual, and an AMPA, a citrullinated protein antigens antibody (ACPA), lysine acetylated protein antigens antibody (AAPA) and/or anti-CarP antibody had been detected in an earlier sample of the individual.

4. The method according to claim 3, wherein the AMPA in the earlier sample tested negative for the presence of N-linked glycosylation on a Fab-portion of the antibodies.

5. The method according to claim 1, wherein the antibody sample is from an individual at risk of developing arthritis.

6. The method according to claim 1, wherein the glycan-binding molecule comprises a lectin, a sialic acid residue binding lectin, a member of the sialic acid-binding immunoglobulin-type lectin (SIGLEC) family, CD22, or the sialic acid-binding part of lectin.

7. The method according to claim 6, wherein the lectin can simultaneously bind two sialic acid residues.

8. The method according to claim 1, wherein the AMPA is a homo-citrullinated protein antigens (anti-CarP) or acetylated lysine protein antigens (AAPA) antibody.

9. The method according to claim 1, further comprising:
   determining whether the antibody sample comprises a citrullinated protein antigens antibody (ACPA antibody), an anti-CarP antibody, or an AAPA antibody by:
   contacting antibodies of the antibody sample with a peptide or protein that comprises a modified protein epitope, wherein the modified protein epitope comprises citrulline, a peptide or protein that comprises a modified protein epitope, wherein the modified protein epitope comprises homo-citrulline, and/or a peptide or protein that comprises a modified protein epitope, wherein the modified protein epitope comprises acetylated lysine; and
   detecting binding between antibodies in the sample and the peptide or protein that comprises a citrulline, the peptide or protein that comprises homo-citrulline, and/or the peptide or protein that comprises an acetylated lysine, and
   determining whether the antibody sample comprises an ACPA antibody, an anti-CarP antibody or an AAPA antibody.

* * * * *

SEQUENCE LISTING

```
<160> NUMBER OF SEQ ID NOS: 11

<210> SEQ ID NO 1
<211> LENGTH: 866
<212> TYPE: PRT
<213> ORGANISM: Homo sapiens

<400> SEQUENCE: 1
```

```
Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65              70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
                100                 105                 110

Leu Arg Gly Asp Phe Ser Ser Ala Asn Asn Arg Asp Asn Thr Tyr Asn
            115                 120                 125

Arg Val Ser Glu Asp Leu Arg Ser Arg Ile Glu Val Leu Lys Arg Lys
        130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
                180                 185                 190

Asp Leu Lys Asp Tyr Glu Asp Gln Gln Lys Gln Leu Glu Gln Val Ile
            195                 200                 205

Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
                260                 265                 270

Gly Ser Thr Ser Tyr Gly Thr Gly Ser Glu Thr Glu Ser Pro Arg Asn
            275                 280                 285

Pro Ser Ser Ala Gly Ser Trp Asn Ser Gly Ser Ser Gly Pro Gly Ser
290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
            355                 360                 365

Ser Ala Gly His Trp Thr Ser Glu Ser Ser Val Ser Gly Ser Thr Gly
        370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415
```

```
Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
        435                 440                 445

Val Thr Ser Gly Ser Thr Thr Thr Thr Arg Arg Ser Cys Ser Lys Thr
    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
        595                 600                 605

Ser Glu Ala Asp His Gly Thr His Ser Thr Lys Arg Gly His Ala
    610                 615                 620

Lys Ser Arg Pro Val Arg Asp Cys Asp Asp Val Leu Gln Thr His Pro
625                 630                 635                 640

Ser Gly Thr Gln Ser Gly Ile Phe Asn Ile Lys Leu Pro Gly Ser Ser
                645                 650                 655

Lys Ile Phe Ser Val Tyr Cys Asp Gln Glu Thr Ser Leu Gly Gly Trp
            660                 665                 670

Leu Leu Ile Gln Gln Arg Met Asp Gly Ser Leu Asn Phe Asn Arg Thr
        675                 680                 685

Trp Gln Asp Tyr Lys Arg Gly Phe Gly Ser Leu Asn Asp Glu Gly Glu
    690                 695                 700

Gly Glu Phe Trp Leu Gly Asn Asp Tyr Leu His Leu Leu Thr Gln Arg
705                 710                 715                 720

Gly Ser Val Leu Arg Val Glu Leu Glu Asp Trp Ala Gly Asn Glu Ala
                725                 730                 735

Tyr Ala Glu Tyr His Phe Arg Val Gly Ser Glu Ala Glu Gly Tyr Ala
            740                 745                 750

Leu Gln Val Ser Ser Tyr Glu Gly Thr Ala Gly Asp Ala Leu Ile Glu
        755                 760                 765

Gly Ser Val Glu Glu Gly Ala Gly Tyr Thr Ser His Asn Asn Met Gln
    770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
```

```
                835                 840                 845
Ala Asp Tyr Ser Leu Arg Ala Val Arg Met Lys Ile Arg Pro Leu Val
        850                 855                 860

Thr Gln
865

<210> SEQ ID NO 2
<211> LENGTH: 488
<212> TYPE: PRT
<213> ORGANISM: Homo sapiens

<400> SEQUENCE: 2

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
    210                 215                 220

Thr Pro Cys Thr Val Ser Cys Asn Ile Pro Val Val Ser Cys Glu Glu
225                 230                 235                 240

Ile Ile Arg Lys Gly Gly Glu Thr Ser Glu Met Tyr Leu Ile Gln Pro
                245                 250                 255

Asp Ser Ser Val Lys Pro Tyr Arg Val Tyr Cys Asp Met Asn Thr Glu
            260                 265                 270

Asn Gly Gly Trp Thr Val Ile Gln Asn Arg Gln Asp Gly Ser Val Asp
        275                 280                 285

Phe Gly Arg Lys Trp Asp Pro Tyr Lys Gln Gly Phe Gly Asn Val Ala
    290                 295                 300

Thr Asn Thr Asp Gly Lys Asn Tyr Cys Gly Leu Pro Gly Glu Tyr Trp
305                 310                 315                 320

Leu Gly Asn Asp Lys Ile Ser Gln Leu Thr Arg Met Gly Pro Thr Glu
                325                 330                 335
```

```
Leu Leu Ile Glu Met Glu Asp Trp Lys Gly Asp Lys Val Lys Ala His
            340                 345                 350

Tyr Gly Gly Phe Thr Val Gln Asn Glu Ala Asn Lys Tyr Gln Ile Ser
        355                 360                 365

Val Asn Lys Tyr Arg Gly Thr Ala Gly Asn Ala Leu Met Asp Gly Ala
    370                 375                 380

Ser Gln Leu Met Gly Glu Asn Arg Thr Met Thr Ile His Asn Gly Met
385                 390                 395                 400

Phe Phe Ser Thr Tyr Asp Arg Asp Asn Asp Gly Trp Leu Thr Ser Asp
                405                 410                 415

Pro Arg Lys Gln Cys Ser Lys Glu Asp Gly Gly Gly Trp Trp Tyr Asn
                420                 425                 430

Arg Cys His Ala Ala Asn Pro Asn Gly Arg Tyr Tyr Trp Gly Gly Gln
                435                 440                 445

Tyr Thr Trp Asp Met Ala Lys His Gly Thr Asp Asp Gly Val Val Trp
        450                 455                 460

Met Asn Trp Lys Gly Ser Trp Tyr Ser Met Arg Lys Met Ser Met Lys
465                 470                 475                 480

Ile Arg Pro Phe Phe Pro Gln Gln
                485

<210> SEQ ID NO 3
<211> LENGTH: 453
<212> TYPE: PRT
<213> ORGANISM: Homo sapiens

<400> SEQUENCE: 3

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
                20                  25                  30

Asn Cys Cys Ile Leu Asp Glu Arg Phe Gly Ser Tyr Cys Pro Thr Thr
            35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
                100                 105                 110

Arg Lys Met Leu Glu Glu Ile Met Lys Tyr Glu Ala Ser Ile Leu Thr
            115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
    195                 200                 205

Glu Ile Asp Gly Ser Gly Asn Gly Trp Thr Val Phe Gln Lys Arg Leu
210                 215                 220
```

```
Asp Gly Ser Val Asp Phe Lys Asn Trp Ile Gln Tyr Lys Glu Gly
225                 230                 235                 240

Phe Gly His Leu Ser Pro Thr Gly Thr Thr Glu Phe Trp Leu Gly Asn
            245                 250                 255

Glu Lys Ile His Leu Ile Ser Thr Gln Ser Ala Ile Pro Tyr Ala Leu
                260                 265                 270

Arg Val Glu Leu Glu Asp Trp Asn Gly Arg Thr Ser Thr Ala Asp Tyr
            275                 280                 285

Ala Met Phe Lys Val Gly Pro Glu Ala Asp Lys Tyr Arg Leu Thr Tyr
        290                 295                 300

Ala Tyr Phe Ala Gly Gly Asp Ala Gly Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
    370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln Gln His His Leu Gly Gly Ala Lys
            420                 425                 430

Gln Val Arg Pro Glu His Pro Ala Glu Thr Glu Tyr Asp Ser Leu Tyr
        435                 440                 445

Pro Glu Asp Asp Leu
    450

<210> SEQ ID NO 4
<211> LENGTH: 120
<212> TYPE: PRT
<213> ORGANISM: Artificial Sequence
<220> FEATURE:
<223> OTHER INFORMATION: RL0633-H heavy chain

<400> SEQUENCE: 4

Gln Val Gln Leu Glu Glu Ser Gly Pro Gly Leu Val Arg Pro Ser Glu
1               5                   10                  15

Thr Leu Ser Leu Thr Cys Ser Val Ser Gly Val Ser Leu Ser Glu Ile
            20                  25                  30

Ser Tyr Phe Trp Gly Trp Val Arg Gln Pro Pro Gly Lys Gly Leu Glu
        35                  40                  45

Trp Ile Gly Thr Ile His Tyr Ser Ala Arg Ile Tyr Tyr Thr Pro Ser
    50                  55                  60

Leu Gln Ser Arg Val Ser Met Ser Val Asp Thr Ser Lys Asn Gln Phe
65                  70                  75                  80

Ser Leu Asn Val Thr Ser Val Thr Ala Ala Asp Thr Ala Val Tyr Tyr
                85                  90                  95

Cys Ala Ile Ser Tyr Asp Tyr Gly Asp Phe Phe Asp Tyr Trp Gly Gln
            100                 105                 110

Gly Ile Leu Val Thr Val Ser Ser
        115                 120
```

<210> SEQ ID NO 5
<211> LENGTH: 111
<212> TYPE: PRT
<213> ORGANISM: Artificial Sequence
<220> FEATURE:
<223> OTHER INFORMATION: RL0633-H light chain

<400> SEQUENCE: 5

```
Ile Phe Ile Leu Ala Gln Pro His Ser Val Ser Glu Ser Ala Gly Lys
1               5                   10                  15

Thr Val Thr Ile Ser Cys Thr Arg Ser Gly Ser Ile Ala Ser Thr
            20                  25                  30

Tyr Val Gln Trp Tyr Gln Gln Arg Pro Gly Ser Ser Pro Ser Thr Val
        35                  40                  45

Val Phe Gln Asn Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Thr
                85                  90                  95

Ala Asn His Val Leu Phe Gly Gly Gly Thr Lys Leu Thr Val Leu
            100                 105                 110
```

<210> SEQ ID NO 6
<211> LENGTH: 125
<212> TYPE: PRT
<213> ORGANISM: Artificial Sequence
<220> FEATURE:
<223> OTHER INFORMATION: RL0676-B heavy chain

<400> SEQUENCE: 6

```
Gln Val Gln Leu Gln Glu Ser Gly Pro Gly Leu Val Lys Pro Ser Glu
1               5                   10                  15

Thr Leu Ser Leu Thr Cys Asn Val Ser Gly Gly Ser Leu Lys Ser Asp
            20                  25                  30

Asn Phe Tyr Trp Ser Trp Ile Arg Gln Arg Pro Gly Gln Gly Leu Glu
        35                  40                  45

Phe Ile Gly Tyr Tyr Val Tyr Ser Asp Ile Thr Tyr Phe Asn Pro Ser
    50                  55                  60

Leu Lys Ser Arg Val Asn Ile Ser Leu Asp Thr Ser Lys Arg Gln Leu
65                  70                  75                  80

Ser Leu Gln Val Arg Ser Val Thr Ala Ala Asp Thr Gly Ile Tyr Tyr
                85                  90                  95

Cys Ala Arg Gly Ile Gly Leu Gly Asp Val Ile Ile Cys Glu Gly Phe
            100                 105                 110

Asp Val Trp Gly Arg Gly Thr Thr Val Thr Val Ser Ser
            115                 120                 125
```

<210> SEQ ID NO 7
<211> LENGTH: 110
<212> TYPE: PRT
<213> ORGANISM: Artificial Sequence
<220> FEATURE:
<223> OTHER INFORMATION: RL0676-B light chain

<400> SEQUENCE: 7

```
Asn Phe Leu Leu Ala Gln Pro His Ser Val Ser Glu Ser Pro Gly Lys
1               5                   10                  15
```

-continued

```
Thr Ile Thr Leu Ser Cys Thr Arg Ser Ser Gly Asn Val Ala Ser Glu
            20                  25                  30

Ser Val Gln Trp Tyr Gln Gln Arg Pro Gly Ser Ser Pro Thr Thr Val
        35                  40                  45

Ile Leu Gln Asn Asn Arg Arg Pro Ser Gly Val Pro Asp Arg Phe Ser
50                  55                  60

Gly Ser Ile Asp Thr Ser Ser Asn Ser Ala Ser Leu Thr Ile Ser Gly
65                  70                  75                  80

Leu Arg Pro Glu Asp Glu Ala Asp Tyr Phe Cys Gln Ser Phe Asp Ser
                85                  90                  95

Ser Gly Leu Ile Phe Gly Gly Gly Thr Lys Leu Thr Val Leu
            100                 105                 110
```

<210> SEQ ID NO 8
<211> LENGTH: 123
<212> TYPE: PRT
<213> ORGANISM: Artificial Sequence
<220> FEATURE:
<223> OTHER INFORMATION: RL0758-E heavy chain

<400> SEQUENCE: 8

```
Gln Val Gln Leu Val Glu Ser Gly Gly Gly Val Val Gln Pro Gly Lys
1               5                   10                  15

Ser Leu Arg Leu Ser Cys Val Ala Ser Gly Phe Thr Phe Lys Asn Phe
            20                  25                  30

Ala Leu His Trp Val Arg Gln Ala Pro Gly Arg Gly Leu Glu Trp Leu
        35                  40                  45

Ala Val Ile Ser Asp Asp Gly Ser Glu Ser His Tyr Ala Asp Ser Val
50                  55                  60

Gln Gly Arg Phe Leu Ile Ser Arg Asp Asn Ser Thr Asn Thr Leu Val
65                  70                  75                  80

Leu Gln Met Asn His Leu Arg Ser Asp Thr Ala His Tyr Tyr Cys
                85                  90                  95

Ala Arg Asp Leu Ser Lys Ile Phe Pro Leu Tyr Tyr Gly Met Asp Val
            100                 105                 110

Trp Gly Gln Gly Thr Thr Val Ile Val Ser Ala
            115                 120
```

<210> SEQ ID NO 9
<211> LENGTH: 108
<212> TYPE: PRT
<213> ORGANISM: Artificial Sequence
<220> FEATURE:
<223> OTHER INFORMATION: RL0758-E light chain

<400> SEQUENCE: 9

```
Glu Val Val Leu Thr Gln Ser Pro Gly Thr Leu Ser Leu Ser Pro Gly
1               5                   10                  15

Glu Arg Ala Thr Leu Ser Cys Arg Ala Ser Arg His Val Ser Ser Thr
            20                  25                  30

Tyr Leu Val Trp Tyr Gln His Lys Pro Gly Gln Pro Pro Arg Leu Leu
        35                  40                  45

Ile Ser Gly Ala Ser Arg Arg Ala Thr Gly Ile Pro Asp Arg Phe Asn
50                  55                  60

Gly Ser Gly Ser Gly Thr Asp Phe Thr Leu Thr Ile Ala Ser Leu Glu
65                  70                  75                  80

Pro Glu Asp Phe Ala Val Tyr Tyr Cys His His Tyr Gly Phe Ser Pro
                85                  90                  95
```

Cys Ser Phe Gly Gln Gly Thr Lys Leu Glu Ile Lys
                100                 105

<210> SEQ ID NO 10
<211> LENGTH: 609
<212> TYPE: PRT
<213> ORGANISM: Homo sapiens

<400> SEQUENCE: 10

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Gly Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Gly Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val

```
                355                 360                 365
Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Cys Leu Ser Val Phe
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Gly Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 11
<211> LENGTH: 418
<212> TYPE: PRT
<213> ORGANISM: Homo sapiens

<400> SEQUENCE: 11

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
```

-continued

```
            115                 120                 125
Gln Pro Asp Ser Gln Leu Gln Leu Thr Thr Gly Asn Gly Leu Phe Leu
        130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
                180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
        210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
        290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
        370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys
```